United States Patent
Seno et al.

(10) Patent No.: US 7,662,826 B2
(45) Date of Patent: Feb. 16, 2010

(54) PYRAZOLO [1,5-A] PYRIMIDINE DERIVATIVE AND NAD (P) H OXIDASE INHIBITOR CONTAINING THE SAME

(75) Inventors: Kaoru Seno, Osaka (JP); Koichi Nishi, Osaka (JP); Yoshiyuki Matsuo, Toyonaka (JP); Toshio Fujishita, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 554 days.

(21) Appl. No.: 10/511,840

(22) PCT Filed: Apr. 18, 2003

(86) PCT No.: PCT/JP03/05024

§ 371 (c)(1),
(2), (4) Date: Sep. 23, 2005

(87) PCT Pub. No.: WO03/091256

PCT Pub. Date: Nov. 6, 2003

(65) Prior Publication Data

US 2006/0089362 A1    Apr. 27, 2006

(30) Foreign Application Priority Data

Apr. 23, 2002 (JP) .............................. 2002-121519

(51) Int. Cl.
| | |
|---|---|
| C07D 487/04 | (2006.01) |
| A61K 31/519 | (2006.01) |
| A61K 31/5377 | (2006.01) |
| A61P 9/00 | (2006.01) |
| A61P 9/10 | (2006.01) |
| A61P 9/12 | (2006.01) |
| A61P 11/00 | (2006.01) |
| A61P 27/02 | (2006.01) |
| A61P 29/00 | (2006.01) |
| A61P 43/00 | (2006.01) |

(52) U.S. Cl. .................................. 514/259.3; 544/281
(58) Field of Classification Search ................. 544/281; 514/259.3

See application file for complete search history.

(56) References Cited

U.S. PATENT DOCUMENTS

| 4,081,545 A | 3/1978 | Clayton | |
|---|---|---|---|
| 4,166,817 A | 9/1979 | Ferres et al. | |
| 4,918,074 A | 4/1990 | Tsuda et al. | 514/258 |
| 4,992,442 A | 2/1991 | Tsujitani et al. | 514/267 |
| 5,420,128 A * | 5/1995 | Kiyokawa et al. | 514/246 |
| 5,478,838 A | 12/1995 | Arita et al. | 514/300 |
| 5,888,941 A | 3/1999 | Bartroli et al. | 504/262 |
| 6,229,011 B1 | 5/2001 | Chen et al. | 544/171 |
| 2001/0025047 A1 | 9/2001 | Levin et al. | 514/310 |
| 2001/0046989 A1 | 11/2001 | Levin et al. | 514/228.8 |
| 2002/0132826 A1 | 9/2002 | Levin et al. | 514/311 |

FOREIGN PATENT DOCUMENTS

| GB | 1 568 962 | 6/1980 |
|---|---|---|
| GB | 1 579 362 | 11/1980 |
| JP | 06-009638 | 1/1994 |
| JP | 07-242670 | 9/1995 |
| JP | 07-267960 | 10/1995 |
| JP | 10-120683 | 5/1998 |
| JP | 2001-302666 | 10/2001 |
| WO | WO 99/10313 | 3/1999 |
| WO | WO 99/18076 | 4/1999 |
| WO | WO 99/59526 | 11/1999 |
| WO | WO 01/90101 | 11/2001 |
| WO | WO 02/24613 | 3/2002 |
| WO | WO 02/28820 | 4/2002 |

OTHER PUBLICATIONS

Bartroli et al., "New Azole Antifungals. 2. Synthesis and Antifungal Activity of Heterocyclecarboxamide Derivatives of 3-Amino-2-aryl-1-azolyl-2-butanol," *J. Med. Chem.*, 41:1855-1868 (1998).
Checchi et al., "5-Aminopyrazole derivatives. III. Acids of pyrazopyrimidine, pyrazopyridone, pyrazopyridine, and some derivatives," *Gazzetta Chimica Italiana*, 86:631-645 (1956) (with attached English-language abstract).
Checchi et al., "Derivaties of 5-aminopyrazole. IV. Synthesis of heterocyclic derivatives," *Gazzetta Chimica Italiana*, 87:597-614 (1957) (with attached English-language abstract).
Elworthy et al., "N-Arylpiperazinyl-N'-propylamino Derivatives of Heteroaryl Amides as Functional Uroselective $\alpha_1$-Adrenoceptor Antagonists," *J. Med. Chem.*, 40:2674-2687 (1997).
Mustazza et al., "Synthesis of Pyrazolo[1,5-a]-1,2,4-Triazolo[1,5-a]- and Imidazo[1,2-a]pyrimidines Related to Zaleplon, a New Drug for the Treatment of Insomnia," *J. Heterocyclic Chem.*, 38:1119-1129 (2001).
Novinson et al., "Synthesis and Antifungal Properties of Certain 7-Alkylaminopyrazolo[1,5-a]pyrimidines," *Journal of Medicinal Chemistry*, 20(2):296-299 (1977).
Takamizawa et al., "Studies on Pyrimidine Derivatives and Related Compounds, LIX. Syntheses of 2,3- Dihydro-1H-pyrazolo[5,1-b]purin-2-ones," *Chem. Pharm. Bull.*, 16(11):2195-2199 (1968).

* cited by examiner

*Primary Examiner*—Bruck Kifle
(74) *Attorney, Agent, or Firm*—Ropes & Gray LLP; James F. Haley, Jr.; Brian M. Gummow

(57) ABSTRACT

A compound represented by the formula (Ia) (wherein R1a, R2a, and R3 to R5 are the same as defined in the description), a prodrug thereof, a pharmaceutically acceptable salt thereof, or solvate thereof. The compounds are useful in the prevention of or treatment for diseases relating to NAD(P)H.

12 Claims, No Drawings

PYRAZOLO [1,5-A] PYRIMIDINE DERIVATIVE AND NAD (P) H OXIDASE INHIBITOR CONTAINING THE SAME

This application is a National Stage application (35 U.S.C. §371) of copending International Application PCT/JP03/05024, filed Apr. 18, 2003, which designates the United States and which claims priority to Japanese Application No. 2002-121519, filed Apr. 23, 2002.

TECHNICAL FIELD

The present invention relates to the fields of medicaments, animal drugs (livestock drugs, veterinary drugs, fishery drugs, and the like). More particularly, it relates to pyrazolo-[1,5-a]-pyrimidine derivatives and analogues, and NAD(P)H oxydase inhibitors containing the same for the prevention of and treatment for NAD(P)H-related diseases.

BACKGROUND ART

It is considered that reactive oxygen species (ROS) derived from immunocytes such as neutrophils and phagocytes not only biophylactically acts on the invaded pathogen (Babior, B. M., N. Engl. J. Med., 298, 659-668, 721-725, 1978), but also destructively on tissue in inflammation or circulation disorders (Weiss, S. J., N. Engl. J. Med., 320, 365-376, 1989). The main source of ROS production by neutrophils is NAD (P)H oxidase (Hallett, M. B. et al., Immunology Today, 16, 264-2681 1995), and it has been indicated that inhibition of neutrophil NAD(P)H oxidase can decrease organopathy in diseases involving neutrophils, such as inflammatory disease and circulation disorders (Schmid-Schonbein, G. W. et al., Physiology and pathology of leukocyte adherence, New York, Oxford University Press, 1995).

On the other hand, it has been previously reported that non-phagocytes such as smooth muscle cells, fibroblasts and vascular endothelial cells also can produce superoxide anion ($O_2^-$) dependant on NADPH or NADH and the potential association with cell functions, such as cell proliferation, hyperpermeability, and contraction and relaxation has been suggested (Griendling, K. K. et al., Circ.Res., 86, 494-501, 2000). Oxygen itself was first considered to be almost the same as neutrophil NAD(P)H oxidase. In recent years, the genes of the isozyme of gp91-phox, as a membrane-constituent factor of neutrophil NAD(P)H oxidase, was successively cloned. At present, Duox (dual oxidase) is known as an isozyme having five kinds of Nox from Nox 1 to Nox 5, peroxidase activity and clearly forms the Nox-Duox family, suggesting its potential involvement in various tissue and cell functions and the onset of diseases (Lambeth, J. D., Curr. Opin. Hematol., 9, 11-17, 2002).

The NAD(P)H oxidase of vascular smooth muscle cells and vascular endothelial cells is activated by many stimulations such as blood pressure regulatory hormones including angiotensin II (Ang II), cytokine, thrombin, PDGF, insulin, mechanical stimulation, hyperglycemia and hyperlipemia etc., predicting its involvement in various cardiovascular diseases. The spontaneous hypertensive rat model or the hypertensive rat model by the continuous administration of Ang II, has been reported to result in an increase in $O_2^-$ production in blood vessel walls via NAD(P)H oxidase and the suppression of the blood pressure increase by the inhibition of NAD(P)H oxidase (Chen, X. et al., Hypertension, 38, 606-611, 2001; Rey, F. E. et al., Circ. Res., 89., 408-414, 2001), suggesting the potential involvement of NAD(P)H oxidase in blood pressure regulation.

Arteriosclerosis lesions are a chronic inflammatory multiplicative change in blood vessels and ROS produced in blood vessel walls plays an important role in its onset and development. In the p47phox knockout mouse, which fails to express a cytoplasmic component of NAD(P)H oxidase, the development of arteriosclerosis lesions has been reported to be inhibited when the mice are subjected to a high cholesterol load (Stokes, K. Y. et al. Circ. Res., 88, 499-505, 2001; Barry-Lane, P. A. et al., J. Clin. Invest., 108, 1513-1522, 2001). ROS is involved in the neointima growth after balloon injury and induces vascular restenosis. In recent years, the increase in NAD(P)H oxidase activity in vascular wall after balloon injury was reported (Shi, Y. et al., Arterioscler. Thromb. Vasc. Biol., 21, 739-745, 2001; Szocs, K. et al., Arterioscler. Thromb. Vasc. Biol., 22, 21-27, 2002). It was also reported that the NAD(P)H oxidase hypoactivity by C242T genetic variation of p22phox, as a cell membrane component, correlated with a decrease in the incidence rate of coronary artery disease (Inoue, N. et al., Circulation, 97, 135-137, 1998; Cai, H. et al., Eur. J. Clin. Invest., 29, 744-748, 1999; Cahilly, C. et al., Circ. Res., 86, 391-395, 2000). These reports indicate the potential involvement of NAD(P)H oxidase in the onset and development of arteriosclerosis and coronary artery diseases.

The potential involvement of ROS in the onset and development of diabetic complications has been indicated. It has been reported that the stimulation by hyperglycemia or glycated protein enhances oxidative stress via NAD(P)H oxidase in vascular endothelial cells, smooth muscle cells, etc. (Inoguchi, T. et al. Diabetes, 49, 1939-1945, 2000; Hink, U. et al. Circ. Res., 88, E14-E22, 2001; Wautier, M. et al., Am. J. Physiol., 280, E685-E694, 2001). The correlation between the increase in NAD(P)H oxidase activity and the injury of retinal vascular endothelial cells was also reported in retinal vessels of a diabetic model rat (Ellis, E. A. et al., Free Radic. Biol. Med., 24, 111-120, 1998).

For cerebral circulation disorders like stroke, it has been reported that leukocytes are involved in tissue injury (Hartl, R. et al., J. Cereb. Blood Flow Metab., 16, 1108-1119, 1996). The reduction of cerebral ischemia lesions has been reported in mice defective in neutrophil NAD(P)H oxidase activity (Walder, C. E. et al., Stroke, 28, 2252-2258, 1997). It also has been reported that stimulation by ischemia, inflammation, β-Amyloid, etc. could induce neuronotoxicity by activating NAD(P)H oxidase of microglia cells (Spranger, M. et al. J. Cereb. Blood Flow Metab., 18, 674-678, 1998; Vianca, V. D. et al., J. Biol. Chem., 274, 15493-15499, 1999; Green, S. P. et al., J. Cereb. Blood Flow Metab., 21, 374-384, 2001). These results suggest the potential involvement of NAD(P)H oxidase in stroke and neurodegenerative diseases.

ROS produced from NAD(P)H oxidase is involved in cell proliferation and vascularization, suggesting an association with tumor hyperplasia (Arnold, R. S. et al., Proc. Natl. Acad. Sci. USA, 98, 5550-5555, 2001; Arbiser, J. L. et al., Proc. Natl. Acad. Sci. USA, 99, 715-720, 2002).

Besides the aforesaid, NAD(P)H oxidase activity has been reported in the kidney cells, gastric cells, fat cells, chondrocytes, etc., raising the association with cell function. As stated above, NAD(P)H oxidase is widely associated with the onset and development of the diseases based on inflammation, circulation disorders and enhancement of proliferation activity, etc., i.e. hypertension, diabetic complications, arteriosclerosis, coronary artery disease, stroke, ischemic disease, neurodegenerative diseases, pulmonary circulation disorders, nephritis, arthritis, inflammatory diseases, cancer, etc. There is a possibility that NAD(P)H oxidase inhibitors can restrain these diseases.

The following compounds having a pyrazolo-[1,5-a]-pyrimidine backbone are known in the art.

Japanese Laid-open Patent Publication No. 5-112571 discloses the following compound:

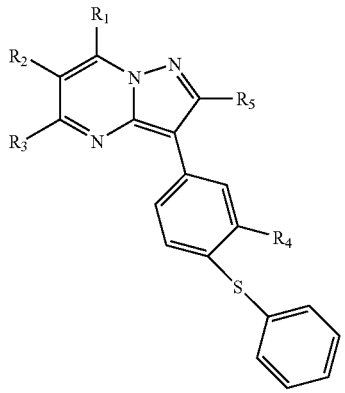

wherein, $R_1$ is hydrogen, or OH;
$R_2$ is hydrogen, lower alkoxycarbonyl, lower alkoxy, halogen, lower alkyl, —CONHR$_6$ (R$_6$ is hydrogen, phenyl that may have a halogen atom, lower alkyl), or the like;
$R_3$ is hydrogen, OH, lower alkyl, or the like;
$R_5$ is hydrogen, lower alkyl, lower alkoxy lower alkyl, or halogenated lower alkyl; and
$R_4$ is hydrogen, lower alkyl, or lower alkoxy. This publication discloses that this compound inhibits the expression of androgen functions, and may be used for the treatment of enlarged prostate, female hirsutism, male baldness, acne, and the like.

WO 00/59908 discloses the following compound:

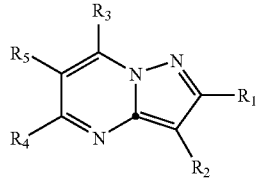

wherein, $R_3$ is (substituted) aryl, or (substituted) heteroaryl; and
$R_4$ and $R_5$ are hydrogen, halogen, CN, alkyl, alkenyl, alkynyl, cycloalkyl, alkoxy, alkylthio, alkylsulfinyl, alkylsulfonyl, amino, alkylamino, or (substituted) phenyl. This compound has corticotropin releasing factor receptor antagonizing functions, and its uses include mental diseases, nervous diseases, anxiety, trauma stress, eating disorders, circulatory diseases, and the like.

Japanese Laid-open Patent Publication No. 10-101672 discloses the following compound:

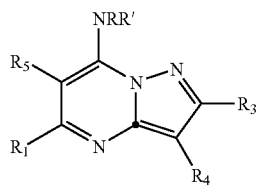

wherein, $R_1$ is hydrogen, (substituted) lower alkyl, cycloalkyl, thienyl, furyl, lower alkenyl, or (substituted) phenyl; and $R_5$ is hydrogen, or lower alkyl. This compound is used as an adenosine enhancer. Its uses includes the treatment of cardiac infarction, and brain infarction.

Japanese Laid-open Patent Publication No. 7-157485 discloses the following compound:

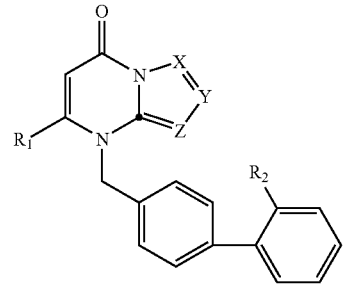

wherein, $R_1$ is hydrogen, lower alkyl, lower alkenyl, lower alkynyl, lower alkoxy, or lower alkylthio; and
X, Y, Z are N or CR$_3$. This compound is an angiotensin II antagonist. Its uses include the treatment of circulatory diseases such as stroke.

EP 0328700A1 discloses the following compound:

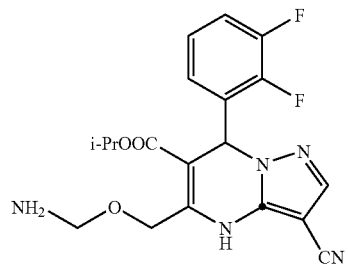

The uses of this compound include the treatment of cerebral circulatory diseases.

WO 00/53605 discloses the following compound:

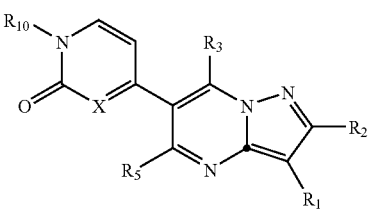

wherein, X is CH or N;
$R_1$ and $R_3$ are hydrogen, alkyl, alkenyl, alkynyl, aryl, halo, OH, or heterocyclyl; and
$R_5$ is hydrogen, alkyl, OH, O-alkyl, halo, amino, or nitro. This compound has tyrosine kinase inhibitory action. Its uses include the treatment of cancers, vascularization, diabetic complications, inflammation, and the like.

WO98/54093 discloses the following compound:

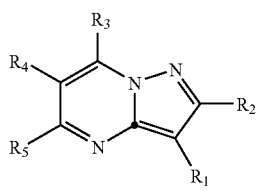

wherein, $R_1$ is hydrogen, (substituted) alkyl, cycloalkyl, aryl, (substituted) heterocyclyl, halo, OH, or (substituted) heteroaryl;

$R_2$ and $R_3$ are hydrogen, alkyl, aryl, cycloalkyl, OH, halo, amino, or nitro;

$R_4$ is hydrogen, (substituted) alkyl, cycloalkyl, alkoxy, (substituted) alkenyl, (substituted) alkynyl, (substituted) aryl, (substituted) heterocyclyl, alkoxy-NRR, $NO_2$, OH, $NH_2$, or (substituted) heteroaryl; and $R_5$ is hydrogen, alkyl, alkoxy, OH, halo, $NO_2$, or $NH_2$.

This compound has tyrosine kinase inhibitory action. Its uses include the treatment of cancers, vascularization, diabetic complications, inflammation, and the like.

Japanese Laid-open Patent Publication No. 4-270285 discloses the following compound:

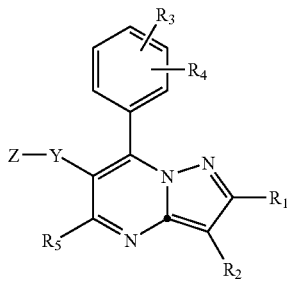

wherein, Y is a lower alkylene, or lower alkenylene; and

Z is substituted acetyl, heterocyclic, or the like. This compound inhibits HMGCOA reducing enzyme. Its uses include the treatment of hyperlipemia.

WO00/44754 discloses the following compound:

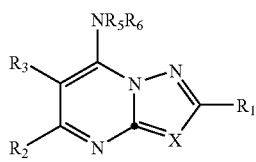

wherein, $R_2$ and $R_3$ are hydrogen, halogen, (substituted) alkyl, (substituted) alkenyl, (substituted) aryl, (substituted) aralkyl, or (substituted) heterocyclic group, or together form an alkylene group.

X is N or $CR_4$. This compound inhibits fat accumulation. Its uses include the treatment of obesity, diabetes, and hypertension.

Japanese Patent Publication No. 2000-38350 discloses the following compound:

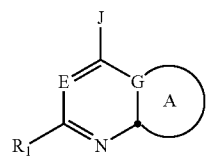

wherein, E is N, or $CR_9$ ($R_9$ is hydrogen, alkyl, halogen, cyano, hydroxy, or alkoxy);

$R_1$ is hydrogen, alkyl, cycloalkyl, alkoxy, (alkyl)amino, aryl, or heteroaryl;

J is $NR_2R_3$, or $OR_{10}$; and

G is C or N. The heterocycles of the A ring include

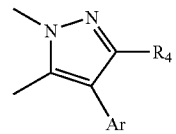

This compound has corticotropin releasing factor (CRF) receptor antagonizing functions. Its uses include the treatment of diabetes.

Japanese Laid-open Patent Publication No. 9-169762 discloses the following compound:

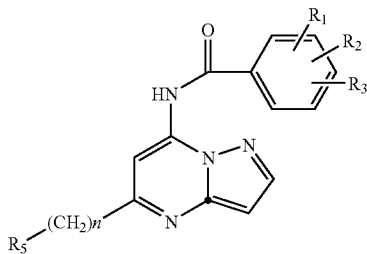

wherein, $R_5$ is carboxy, or lower alkoxycarboxy, (substituted) carbamoyl (the substituent is lower alkyl, or phenyl lower alkyl); and n is 1-5. The functions of this compound are unknown. Its uses include pain relief, lowering blood sugar level, and the treatment of inflammation, bacterial infection, cancers, and the like.

Khim.-Farm. Zh (1995), 29 (4), 37-38 discloses (2,5-dimethyl pyrazolo-[1,5-a]-pyrimidin-7-yl) succinic acid. Its uses include the treatment of diabetes.

The purpose of the present invention is to provide novel compounds that inhibit NAD(P)H oxydase, and compositions comprising the compound. Another purpose of the present invention is to provide pharmaceutical compositions (including quasi-drugs), animal drug (livestock drugs, veterinary drugs, fishery drugs, and the like) compositions, as well as diagnostic drugs that are used to diagnose NAD(P)H-related diseases.

A further purpose of the present invention is to treat or prevent diseases due to inflammation, circulatory disorders, enhanced proliferation activities, and the like, i.e., hypertension, diabetic complications, arteriosclerosis, coronary artery disorders, strokes, ischemic heart disease, neurodegenerative diseases, pulmonary circulation disorders, nephritis, arthritis, inflammatory diseases, cancers and the like.

SUMMARY OF THE INVENTION

The present inventors have found that the following pyrazolo-[1,5-a]-pyrimidine derivatives and analogues have a NAD(P)H oxydase inhibitory function in heterophilic leukocytes and blood vessels. The inhibition of NAD(P)H oxydase provides the reduced production of active enzymes (ROS, superoxide), and effects on various circulatory diseases (such as diseases due to inflammation, circulatory disorders, enhanced proliferation activities, and the like, i.e., hypertension, diabetes, diabetic complications, arteriosclerosis, coronary artery disorders, strokes, ischemic heart disease, neurodegenerative diseases, pulmonary circulation disorders, cerebral circulation disorders, nephritis, arthritis, inflammatory diseases, cancers), and gastric mucosa disorders (such as gastric ulcer).

According to the present invention, the following items 1)-26) are provided to accomplish the above-described purposes.

1) A compound represented by the formula:

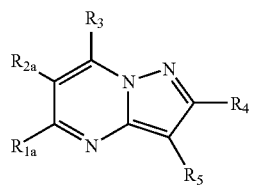

(Ia)

or a prodrug, pharmaceutically acceptable salt or solvate thereof, wherein, in the formula (1a), $R_{1a}$, $R_{2a}$, $R_3$-$R_5$ represent, each independently, hydrogen, halogen, lower alkyl that may be substituted, lower alkenyl that may be substituted, lower alkynyl that may be substituted, cycloalkyl that may be substituted, cycloalkenyl that may be substituted, cycloalkynyl that may be substituted, aryl that may be substituted, heterocyclic group that may be substituted, hydroxy, alkoxy that may be substituted, aryloxy that may be substituted, heterocyclic oxy that may be substituted, acyl that may be substituted, monosubstituted carbonyloxy that may be substituted, carbamoyl that may be substituted, diazo, amidino that may be substituted, azido, nitroso, nitro, amino that may be substituted, imino that may be substituted, cyano, mercapto, monosubstituted thio that may be substituted, monosubstituted thioxy that may be substituted, monosubstituted sulfinyl that may be substituted, monosubstituted sulfonyl that may be substituted, sulfo, or trisubstituted silyl, and any combinations of $R_{1a}$, $R_{2a}$, $R_3$-$R_5$ may together form a ring structure; provided that the following (i)-(x) are excluded:

(i) a compound, wherein $R_{1a}$ is hydrogen, OH, lower alkyl, cycloalkyl having a carbon number of 3-8, halogenated lower alkyl, or phenyl;

$R_{2a}$ is hydrogen, lower alkoxycarbonyl, lower alkoxy, halogen, lower alkyl, cycloalkyl having a carbon number of 3-8, lower alkoxycarbonyl lower alkyl, carboxyl, carboxy lower alkyl, —$CONHR_6$ ($R_6$: hydrogen; phenyl that may have a halogen atom, or lower alkyl), cyano; phenyl that may have a substituent selected from the group consisting of a hydroxyl group, halogen atom, lower alkyl group, lower alkoxy and phenylthio group; phenyl lower alkyl group that may have a substituent selected from the group consisting of hydroxyl group and lower alkoxy group on the phenyl ring; lower alkanoyloxy lower alkyl; benzoyl group; lower alkanoyl group that may have halogen atom; or hydroxy lower alkyl group that may have a substituent selected from the group consisting of a phenyl group and halogen atom;

$R_3$ is hydrogen, or OH;

$R_4$ is hydrogen, lower alkyl, lower alkoxy lower alkyl, or halogenated lower alkyl;

$R_5$ is

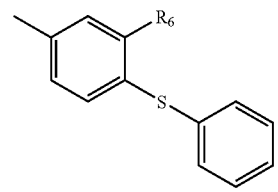

and $R_6$ is hydrogen, lower alkyl, or lower alkoxy;

(ii) a compound, wherein $R_{1a}$ and $R_{2a}$ are, each independently, hydrogen, halogen, CN, alkyl, alkenyl, alkynyl, cycloalkyl, alkoxy, alkylthio, alkylsulfinyl, alkylsulfonyl, amino, alkylamino, or (substituted) phenyl; and $R_3$ is (substituted) aryl, or (substituted) heteroaryl;

(iii) a compound, wherein $R_{1a}$ is hydrogen, (substituted) lower alkyl, cycloalkyl, thienyl, furyl, lower alkenyl, or (substituted) phenyl;

$R_{2a}$ is hydrogen or lower alkyl; and $R_3$ is amino that may be substituted;

(iv) a compound, wherein $R_{1a}$ is hydrogen, alkyl, OH, O-alkyl, halo, amino, or nitro;

$R_{2a}$ is

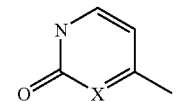

wherein X is CH or N, and the nitrogen atom on the $R_{2a}$ ring may be substituted; and $R_3$ and $R_5$ are, each independently, hydrogen, alkyl, alkenyl, alkynyl, aryl, halo, OH, or heterocyclyl;

(v) a compound, wherein $R_{1a}$ is hydrogen, alkyl, alkoxy, OH, halo, $NO_2$, or $NH_2$;

$R_{2a}$ is hydrogen, (substituted) alkyl, cycloalkyl, alkoxy, (substituted) alkenyl, (substituted) alkynyl, (substituted) aryl, (substituted) heterocyclyl, alkoxy-NRR, $NO_2$, OH, $NH_2$, or (substituted) heteroaryl;

$R_3$ and $R_4$ are, each independently, hydrogen, alkyl, aryl, cycloalkyl, OH, halo, amino, or nitro; and $R_5$ is hydrogen, (substituted) alkyl, cycloalkyl, aryl, (substituted) heterocyclyl, halo, OH, or (substituted) heteroaryl;

(vi) a compound, wherein $R_{2a}$ is substituted acetyl, or heterocyclic-substituted lower alkylene or lower alkenylene; and
$R_3$ is phenyl that may be substituted;
(vii) a compound, wherein $R_{1a}$ and $R_{2a}$ are each independently, hydrogen, halogen, (substituted) alkyl, (substituted) alkenyl, (substituted) aryl, (substituted) aralkyl, (substituted) heterocyclic group, or together form an alkylene group; and
$R_3$ is amino that may be substituted;
(viii) a compound, wherein $R_{1a}$ is hydrogen, alkyl, cycloalkyl, alkoxy, (alkyl)amino, aryl, or heteroaryl;
$R_{2a}$ is hydrogen, alkyl, halogen, cyano, hydroxy, or alkoxy;
$R_3$ is amino that may be substituted, or alkoxy that may be substituted; and
$R_5$ is aryl;
(ix) $R_{1a}$ is lower alkyl that is substituted with a substituent selected from the group consisting of carboxy, lower alkoxycarboxy, and substituted carbamoyl;
$R_{2a}$ is hydrogen;
$R_3$ is phenylcarbonylamino, wherein said phenyl group may be substituted; and
$R_4$ and $R_5$ are hydrogen;
(x) (2,5-dimethyl-pyrazolo-[1,5-a]-pyrimidine-7-yl) succinic acid;
wherein the undefined substituents in the compounds (i)-(x) represent any substituents.

2) The compound of item 1, wherein either one of $R_{1a}$ and $R_{2a}$ is hydrogen, and the other one is carbamoyl that may be substituted.

3) The compound of item 1, represented by the formula:

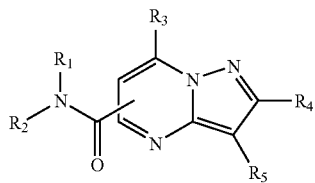

(I)

or a prodrug, pharmaceutically acceptable salt or solvate thereof,
wherein, in the formula (I),
$R_1$ is hydrogen, lower alkyl, amino that may be substituted, or aryl lower alkyl that may be substituted; and
$R_2$ is hydrogen, lower alkyl that may be substituted, cycloalkyl that may be substituted, cycloalkyl lower alkyl that may be substituted, lower alkoxy that may be substituted, aryl that may be substituted, aryl lower alkyl that may be substituted, aryloxy lower alkyl that may be substituted, lower alkylsulfonyl that may be substituted, arylsulfonyl that may be substituted, heteroaryl lower alkyl that may be substituted, heterocyclic group lower alkyl that may be substituted, or amino that may be substituted; or
$R_1$ and $R_2$ together with the adjacent N atom may form a heterocycle that may be substituted;
$R_3$ is hydrogen, hydroxy, lower alkoxy, halogen, or amino that may be substituted;
$R_4$ is hydrogen, lower alkyl, or aryl that may be substituted; and
$R_5$ is hydroxy, lower alkyl that may be substituted, aryl that may be substituted, aryl lower alkyl that may be substituted, cycloalkyl lower alkyl that may be substituted, aryl lower alkenyl that may be substituted, cycloalkyl lower alkenyl that may be substituted, aryl lower alkynyl that may be substituted, cycloalkyl lower alkynyl that may be substituted, aryl carbonyl that may be substituted, aryl lower alkyl carbonyl that may be substituted, heterocyclic group that may be substituted, halogen, CHO, amino that may be substituted, or imino that may be substituted; provided that a compound represented by the following formula is excluded:

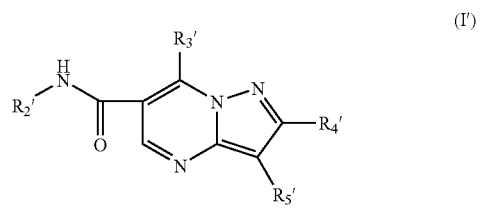

(I')

wherein, in the formula (I'),
$R_2'$ is hydrogen, phenyl that may be substituted with lower alkyl or halogen; $R_3'$ is hydrogen or hydroxy; $R_4'$ is hydrogen or lower alkyl; and $R_5'$ is phenyl having phenylthio group that may further be substituted with lower alkyl or lower alkoxy.

4) The compound of item 3 represented by the formula:

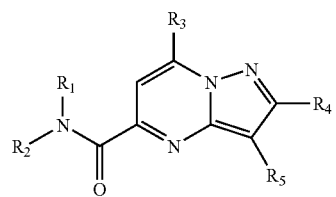

(I-1)

or a prodrug, pharmaceutically acceptable salt or solvate thereof,
wherein, in the formula (I-1), each substituent is as defined above.

5) The compound of item 3 or 4, or a prodrug, pharmaceutically acceptable salt or solvate thereof, wherein $R_1$ is hydrogen; and $R_2$ is aryl that may be substituted.

6) The compound of item 3 or 4, or a prodrug, pharmaceutically acceptable salt or solvate thereof, wherein $R_3$ is hydrogen, or amino that may be substituted.

7) The compound of item 3 or 4, or a prodrug, pharmaceutically acceptable salt or solvate thereof, wherein $R_4$ is hydrogen.

8) The compound of item 3 or 4, or a prodrug, pharmaceutically acceptable salt or solvate thereof, wherein $R_5$ is aryl that may be substituted.

9) The compound of item 3 or 4, or a prodrug, pharmaceutically acceptable salt or solvate thereof, wherein $R_1$ is hydrogen; $R_2$ is phenyl that may be substituted; $R_3$ is hydrogen, or amino that may be substituted; $R_4$ is hydrogen; and $R_5$ is phenyl that may be substituted.

10) The compound of item 9, or a prodrug, pharmaceutically acceptable salt or solvate thereof, wherein the substituent on the phenyl in $R_2$ that may be substituted is one or more selected from the group consisting of heterocyclic group that may be substituted, lower alkyl carbonyl, cycloalkyl, lower alkyl, amino that may be substituted, halogen, halogenated lower alkyl, lower alkoxy, carboxy lower alkyloxy, heterocyclic group lower alkyloxy, amino lower alkyl, hydroxy, cyano, carbamoyl-heterocyclic group-oxy, cyano lower alkyl, and phenyl.

11) The compound of item 10, or a prodrug, pharmaceutically acceptable salt or solvate thereof, wherein $R_2$ is heterocyclic group phenyl that may be substituted.

12) The compound of item 10, or a prodrug, pharmaceutically acceptable salt or solvate thereof, wherein $R_2$ is piperazino phenyl that may be substituted, piperizino phenyl that may be substituted, or pyrrolidino phenyl that may be substituted.

13) The compound of item 9, or a prodrug, pharmaceutically acceptable salt or solvate thereof, wherein the substituent on the phenyl in $R_5$ that may be substituted is one or more selected from the group consisting of halogen, halogenated lower alkyl, aryl lower alkyloxy, lower alkyl, lower alkoxy, hydroxy, lower alkylthio, phenyl, phenyloxy, phenyl lower alkyl, phenyl lower alkylamino, phenyl lower alkylthio, phenyl lower alkenyl, phenyl carbamoyl, amino, cycloalkyl lower alkyloxy, and heteroaryl lower alkyloxy.

14) A pharmaceutical composition, comprising the compound of any of items 1-13.

15) A NAD(P)H oxydase inhibitor, comprising the compound of any of items 1-13.

16) A prophylactic or therapeutic agent for NAD(P)H-related diseases, comprising the compound of any of items 1-13.

17) The prophylactic or therapeutic agent of item 16, wherein the above-described disease is selected from the group consisting of inflammation, pulmonary circulation disorders, ischemic heart disease, cerebral circulation disorders, arteriosclerosis, diabetic complications, hypertension, and proliferative disorders.

18) The prophylactic or therapeutic agent of item 16, wherein the above-described disease is brain infarction or diabetic retinal disorder.

19) A NAD(P)H oxydase inhibitor, comprising a compound represented by the formula (1a):

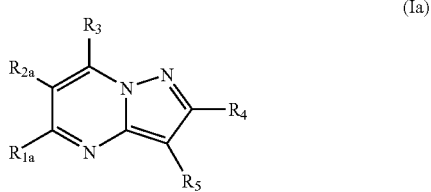

or a prodrug, pharmaceutically acceptable salt or solvate thereof,
wherein, in the formula, $R_{1a}$, $R_{2a}$, $R_3$-$R_5$ represent, each independently, hydrogen, halogen, lower alkyl that may be substituted, lower alkenyl that may be substituted, lower alkynyl that may be substituted, cycloalkyl that may be substituted, cycloalkenyl that may be substituted, cycloalkynyl that may be substituted, aryl that may be substituted, heterocyclic group that may be substituted, hydroxy, alkoxy that may be substituted, aryloxy that may be substituted, heterocyclic oxy that may be substituted, acyl that may be substituted, monosubstituted carbonyloxy that may be substituted, carbamoyl that may be substituted, diazo, amidino that may be substituted, azido, nitroso, nitro, amino that may be substituted, imino that may be substituted, cyano, mercapto, monosubstituted thio that may be substituted, monosubstituted thioxy that may be substituted, monosubstituted sulfinyl that may be substituted, monosubstituted sulfonyl that may be substituted, sulfo, or trisubstituted silyl, and any combinations of $R_{1a}$, $R_{2a}$, $R_3$-$R_5$ may together form a ring structure.

20) A NAD(P)H oxydase inhibitor, comprising a compound represented by the formula (I):

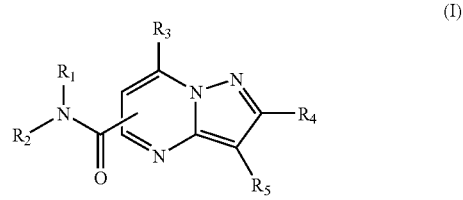

or a prodrug, pharmaceutically acceptable salt or solvate thereof,
wherein, in the formula,
$R_1$ is hydrogen, lower alkyl, amino that may be substituted, or aryl lower alkyl that may be substituted; and
$R_2$ is hydrogen, lower alkyl that may be substituted, cycloalkyl that may be substituted, cycloalkyl lower alkyl that may be substituted, lower alkoxy that may be substituted, aryl that may be substituted, aryl lower alkyl that may be substituted, aryloxy lower alkyl that may be substituted, lower alkylsulfonyl that may be substituted, arylsulfonyl that may be substituted, heteroaryl lower alkyl that may be substituted, heterocyclic group lower alkyl that may be substituted, or amino that may be substituted; or
$R_1$ and $R_2$ together with adjacent N atom may form a heterocycle that may be substituted;
$R_3$ is hydrogen, hydroxy, lower alkoxy, halogen, or amino that may be substituted;
$R_4$ is hydrogen, lower alkyl, or aryl that may be substituted; and
$R_5$ is hydroxy, lower alkyl that may be substituted, aryl that may be substituted, aryl lower alkyl that may be substituted, cycloalkyl lower alkyl that may be substituted, aryl lower alkenyl that may be substituted, cycloalkyl lower alkenyl that may be substituted, aryl lower alkynyl that may be substituted, cycloalkyl lower alkynyl that may be substituted, aryl carbonyl that may be substituted, aryl lower alkyl carbonyl that may be substituted, heterocyclic group that may be substituted, halogen, CHO, amino that may be substituted, or imino that may be substituted.

21) A method of preventing or treating NAD(P)H-related diseases, comprising administering the compound of any of items 1-20 to an animal including human.

22) The method of item 21, wherein the above-described disease is selected from the group consisting of inflammation, pulmonary circulation disorders, ischemic heart disease, cerebral circulation disorders, arteriosclerosis, diabetic complications, hypertension, and proliferative disorders.

23) The method of item 21, wherein the above-described disease is brain infarction or diabetic retinal disorder.

24) A use of the compound of any of items 1-20 for the manufacture of pharmaceuticals employed for preventing or treating NAD(P)H-related diseases.

25) The use of item 24, wherein the above-described disease is selected from the group consisting of inflammation, 26) The use of item 24, wherein the above-described disease is brain infarction or diabetic retinal disorder.

DETAILED DESCRIPTION OF THE INVENTION

The present inventors have continuously devoted considerable efforts, and have found a compound having the above-described backbone that provides a NAD(P)H oxydase inhibitory function. The terms used herein have definitions as those commonly used in the art, unless otherwise indicated.

As used herein, the term, "alkyl", when used alone or in combination with other terms, comprises a straight chain or branched C1-C20 alkyl. For example, these include methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl. Preferably, these include C1-C9 alkyl, more preferably C1-C6 alkyl, especially preferably C1-C4 alkyl.

Preferred specific examples of the substituent in "alkyl that may be substituted" include halogen, hydroxy, lower alkoxy that may be substituted, aryloxy that may be substituted, monosubstituted carbonyloxy that may be substituted, carbamoyl that may be substituted, diazo, cyano, amino that may be substituted, imino that may be substituted, amidino that may be substituted, azido, nitro, nitroso, mercapto, monosubstituted thio that may be substituted, monosubstituted thioxy, monosubstituted sulfinyl that may be substituted, monosubstituted sulfonyl that may be substituted, sulfo, saturated or unsaturated alicyclic hydrocarbon groups that may be substituted, aryl that may be substituted, heterocyclic groups that may be substituted, heterocyclic oxy that may be substituted, acyl that may be substituted, and trisubstituted silyl, and the like.

Additionally, as used herein, the term, "lower" in various groups refers to a carbon number of 1-10, preferably 1-8, more preferably 1-6, especially preferably 1-4 in the group.

As used herein, the number of the substituents that replace the hydrogens in the alkyl group of "the alkyl that may be substituted" is 1-5, preferably 1-3. The position of the substituent is not specifically limited.

As used herein, the term, "alkenyl that may be substituted" comprises a straight chain or branched C2-C12 alkenyl. It may have any available number of double bonds in any available positions, and the configuration of the double bond may be the (E) or (Z) configuration. These include, for example, vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3, 7, 11, 15-tetramethyl-1-hexadecenyl, and the like. Preferably, these include C2-C8 alkenyl, more preferably C2-C6 alkenyl. Among others, especially preferred are vinyl, allyl, isopropenyl, 1-propenyl, 2-methyl-1-propenyl, 1-butenyl, 2-butenyl, and 3-methyl-2-butenyl. As used herein, the term, "that may be substituted" is defined as for the above-discussed "that may be substituted" for "alkyl".

As used herein, the number of the substituents on "the alkenyl that may be substituted" is 1-5, preferably 1-3. The position of the substituent is not specifically limited.

As used herein, the term, "alkynyl that may be substituted" comprises a straight chain or branched C2-C12 alkynyl. It may have any available number of triple bonds in any available positions. These include, for example, alkynyl groups that may have a carbon number of 2-20, and a double bond, such as ethynyl, 1-propynyl, 2-propynyl (propargyl), 2-butynyl, 2-pentene-4-ynyl, and the like. As used herein, the term, "that may be substituted" is defined as for the above-discussed "that may be substituted" for "alkyl".

As used herein, the number of the substituents on "the alkynyl that may be substituted" is 1-5, preferably 1-3. The position of the substituent is not specifically limited. Among the above-described substituents, especially preferred are halogen, hydroxy, lower alkoxy, lower alkenyloxy, and acyl groups.

As used herein, the term, "acyl that may be substituted" includes those acyl groups derived from carboxylic acids that may be substituted, oxycarboxylic acids that may be substituted, and the like. Specifically, these include groups represented by the formulae $R_6C(O)$—, and $R_7OC(O)$— (wherein, in the formulae, $R_6$ and $R_7$ represent a hydrocarbon group or heterocyclic group, each of which may be substituted. Preferably, it is a group represented by the formula, $R_6C(O)$—.

As used herein, "the hydrocarbon groups" in "the hydrocarbon group or heterocyclic group that may be substituted" represented by $R_6$ and $R_7$ include, for example, acylic groups such as straight chain or branched aliphatic hydrocarbons (alkyl, alkenyl, and alkynyl groups, and the like), and cyclic groups such as saturated or unsaturated alicyclic hydrocarbons (cycloalkyl, cycloalkenyl, cycloalkadienyl groups, and the like), aryl groups, and the like.

As used herein, specific examples of preferred "acyl" include, for example, alkanoyls having a carbon number of 1-6 such as formyl, acetyl, propionyl, butyryl, isobutyryl, valeryl, isovaleryl, pivaloyl, hexanoyl, and the like, benzoyl, 2,4-dihydroxyphenyl carbonyl, 2,4-dihydroxy-3-(3-methyl-2-butenyl)phenyl carbonyl, and the like. The term, "that may be substituted" is defined as for the above-discussed "that may be substituted" for "alkyl".

As used herein, the number of the substituents that replace the hydrogens in the acyl group of "the acyl that may be substituted" is 1-5, preferably 1-3. The position of the substituent is not specifically limited. Further, preferred examples of "the acyl that may be substituted" include acetyl that may be substituted, and benzoyl group that may be substituted, wherein the substituents and substitution positions that replace the benzene ring hydrogens in the benzoyl group include, for example, 2-, 3-, or 4-fluoro; 2-, 3-, or 4-chloro; 2-, 3-, or 4-bromo; 2-, 3-, or 4-iodo; 2-, 3-, or 4-methyl; 2, 3-, 2, 4-, or 2,5-dimethyl; 2,6-, 3,4-, or 3,5-dimethyl; 2,3,4-, 2,3,5-, 2,3,6-, 2,4,5-, 2,4,6-, or 3,4,5-trimethyl; 2-, 3-, or 4-ethyl; 2-, 3-, or 4-propyl; 2-, 3-, or 4-trifluoromethyl; 2-, 3-, or 4-methoxy; 2,3-, 2,4-, 2,5-, 2,6-, 3,4-, or 3,5-dimethoxy; 2,3,4-, 2,3,5-, 2,3,6-, 2,4,5-, 2,4,6-, or 3,4,5-trimethoxy; 2-, 3-, or 4-ethoxy; 2-, 3-, or 4-propoxy; 2-, 3-, or 4-trifluoromethoxy; 2-, 3-, or 4-cyano; 2-, 3-, or 4-nitro; or any available combinations of these substituents and substitution positions.

As used herein, the term, "trisubstituted silyl" refers to a group having three hydrogens of silyl (—$SiH_3$) replaced. Trisubstituted silyl is preferably trialkyl silyl, dialkyl monoaryl silyl, or monoalkyl diaryl silyl, that may be substituted. Specific examples of the trialkyl silyl include trimethyl silyl, triethyl silyl, and t-butyl dimethyl silyl. Examples of the monoalkyl diaryl silyl include t-butyl diphenyl silyl, and the like.

As used herein, the term, "aliphatic hydrocarbon group that may be substituted" refers to a straight chain or branched aliphatic hydrocarbon groups (alkyl, alkenyl, and alkynyl groups, and the like).

As used herein, the term, "halogen" includes, for example, fluorine, chlorine, bromine, and iodine. The term, "that may be substituted" is defined as for the above-discussed "that may be substituted" for "alkyl".

As used herein, "alkoxy that may be substituted" includes, for example, "lower alkoxy", "lower alkenyloxy", and the like.

As used herein, the term, "lower alkoxy", of which the lower alkyl has the same meaning as the aforementioned definition, includes, for example, alkoxy groups having a carbon number of 1-6, such as methoxy, ethoxy, propoxy, isopropoxy, butoxy, isobutoxy, neobutoxy, t-butoxy, pentoxy, isopentoxy, and the like. The term, "that may be substituted" is defined as for the above-discussed "that may be substituted" for "alkyl".

As used herein, the term, "lower alkenyloxy", of which the lower alkenyl has the same meaning as the aforementioned definition, includes, for example, alkenyloxy groups having a carbon number of 2-7, such as vinyloxy, allyloxy, 1-propenyloxy, 2-methyl-1-propenyloxy, 1-butenyloxy, 2-butenyloxy, 3-butenyloxy, 2-ethyl-1-butenyloxy, 3-methyl-2-butenyloxy, 1-pentenyloxy, 2-pentenyloxy, 3-pentenyloxy, 4-pentenyloxy, 4-methyl-3-pentenyloxy, and the like. The term, "that may be substituted" is defined as for the above-discussed "that may be substituted" for "alkyl".

As used herein, the term, "aryloxy" includes specifically groups represented by the formula $R_8O$— (wherein, in the formula, $R_8$ is defined as for "the aryl that may be substituted"), such as phenoxy, and the like.

As used herein, the term, "monosubstituted carbonyloxy that may be substituted" includes specifically groups represented by the formulae $R_9C(O)O$— and $R_{10}C(O)O$— (wherein, in the formula, $R_9$ and $R_{10}$ are defined as for "the acyl that may be substituted"), such as alkyl carbonyloxy, cycloalkyl carbonyloxy, aryl carbonyloxy, and heterocyclic carbonyloxy, and the like.

As used herein, the term, "alkyl carbonyloxy" includes, for example, alkyl carbonyloxy groups having a carbon number of 2-7, such as methyl carbonyloxy, ethyl carbonyloxy, propyl carbonyloxy, isopropyl carbonyloxy, butyl carbonyloxy, isobutyl carbonyloxy, t-butyl carbonyloxy, pentyl carbonyloxy, isopentyl carbonyloxy, neopentyl carbonyloxy, t-pentyl carbonyloxy, hexyl carbonyloxy, and the like. The term, "that may be substituted" is defined as for the above-discussed "that may be substituted" for "alkyl".

As used herein, the term, "carbamoyl that may be substituted" includes groups represented by the formula $R_{11}R_{12}NC(=O)$— (wherein, in the formula, $R_{11}$ and $R_{12}$ are hydrogen, lower alkyl that may be substituted, cycloalkyl that may be substituted, cycloalkyl lower alkyl that may be substituted, lower alkoxy that may be substituted, aryl that may be substituted, aryl lower alkyl that may be substituted, aryloxy lower alkyl that may be substituted, lower alkyl sulfonyl that may be substituted, aryl sulfonyl that may be substituted, heteroaryl lower alkyl that may be substituted, heterocyclic group lower alkyl that may be substituted, amino that may be substituted; or $R_{11}$ and $R_{12}$ may together with the adjacent N atom form a heterocycle that may be substituted), and the like. Specifically, "the carbamoyl that may be substituted" includes, for example, carbamoyl, N-mono-lower alkyl carbamoyl, N,N-di-loweralkyl carbamoyl, N-hydroxy carbamoyl, N-lower alkoxy carbamoyl, N-hydroxy-N-lower alkyl carbamoyl, N-lower alkoxy-N-lower alkyl carbamoyl, N-phenyl carbamoyl, and N-substituted phenyl carbamoyl groups, and the like. The term, "that may be substituted" is defined as for the above-discussed "that may be substituted" for "alkyl".

The above-described "N-mono lower alkyl carbamoyl", of which the lower alkyl has the same meaning as the aforementioned definition, includes, for example, N-methyl carbamoyl, N-ethyl carbamoyl, N-propyl carbamoyl, N-isopropyl carbamoyl, N-pentyl carbamoyl, N-isopentyl carbamoyl, N-neopentyl carbamoyl, N-t-pentyl carbamoyl, N-1-ethylpropyl carbamoyl, and N-hexyl carbamoyl, and the like.

The above-described "N, N-di-lower alkyl carbamoyl", of which the lower alkyl has the same meaning as the aforementioned definition, includes, for example, N,N-dimethyl carbamoyl, N-ethyl-N-methyl carbamoyl, N,N-diethyl carbamoyl, N-methyl-N-propyl carbamoyl, N-butyl-N-methyl carbamoyl, N-butyl-N-ethyl carbamoyl, N-butyl-N-prop yl carbamoyl, N-butyl-N-isopropyl carbamoyl, N, N-dibutyl carbamoyl, N-ethyl-N-propyl carbamoyl, N, N-dipropyl carbamoyl, N-isopropyl-N-n-propyl carbamoyl, and N-isopropyl-N-methyl carbamoyl, and the like.

The above-described "N-hydroxy-N-lower alkyl carbamoyl", of which the lower alkyl has the same meaning as the aforementioned definition, includes, for example, N-hydroxy-N-lower alkyl carbamoyl groups having a carbon number of 2-7, such as N-hydroxy-N-methyl carbamoyl, N-hydroxy-N-ethyl carbamoyl, N-hydroxy-N-propyl carbamoyl, N-hydroxy-N-butyl carbamoyl, N-hydroxy-N-isopropyl carbamoyl, N-hydroxy-N-isobutyl carbamoyl, N-hydroxy-N-sec-butyl carbamoyl, N-hydroxy-N-t-butyl carbamoyl, N-hydroxy-N-pentyl carbamoyl, N-hydroxy-N-isopentyl carbamoyl, N-hydroxy-N-neopentyl carbamoyl, and the like.

The above-described "N-lower alkoxy-N— lower alkyl carbamoyl", of which the lower alkyl has the same meaning as the aforementioned definition, includes, for example, N-lower alkoxy-N-lower alkyl carbamoyl groups having a total carbon number of 3-13, such as, N-methoxy-N-methyl carbamoyl, N-methoxy-N-ethyl carbamoyl, N-methoxy-N-propyl carbamoyl, N-methoxy-N-butyl carbamoyl, N-methoxy-N-isopropyl carbamoyl, N-methoxy-N-isobutyl carbamoyl, N-methoxy-N-sec-butyl carbamoyl, N-methoxy-N-t-butyl carbamoyl, N-methoxy-N-pentyl carbamoyl, N-methoxy-N-isopentyl carbamoyl, and N-methoxy-N-neopentyl carbamoyl, and the like.

The substituents for the above-described "N-substituted-phenyl carbamoyl" include lower alkyl, lower alkoxy, and hydroxy, and the like, which have the same meaning as the aforementioned definitions. Preferred specific examples of "N-substituted phenyl carbamoyl" include, for example, (4-methylphenyl)carbamoyl, (4-ethylphenyl)carbamoyl, (4-hydroxyphenyl)carbamoyl, (4-methoxyphenyl)carbamoyl, (2,3-dihydroxy phenyl)carbamoyl, (2,3-methoxyphenyl) carbamoyl, (2,4-dihydroxyphenyl)carbamoyl, (2,4-methoxyphenyl)carbamoyl, (2,6-dihydroxyphenyl)carbamoyl, (2,6-methoxyphenyl)carbamoyl, (2,4,6-trihydroxyphenyl) carbamoyl, (2,4,6-trimethoxyphenyl)carbamoyl, (2,4-dimethoxy-6-hydroxyphenyl)carbamoyl, (2,6-dimethoxy-4-hydroxyphenyl)carbamoyl, (4,6-dihydroxy-2-methoxyphenyl)carbamoyl, (2,6-dihydroxy-4-methoxyphenyl)carbamoyl, (2,3,4-trimethoxyphenyl) carbamoyl, (2,3-dimethoxy-4-hydroxyphenyl)carbamoyl, (2,4-dimethoxy-3-hydroxyphenyl)carbamoyl, (2,3-dihydroxy-4-methoxyphenyl)carbamoyl, (3,4-dimethoxy-2-hydroxyphenyl)carbamoyl, (2,4-dihydroxy-3-methoxyphenyl)

carbamoyl, (2,4-dimethoxy-6-methylphenyl)carbamoyl, and (2,6-dimethoxy-4-methylphenyl)carbamoyl, and the like.

As used herein, the term, "amino that may be substituted" includes, for example, amino, mono-lower alkyl amino, di-lower alkyl amino, lower alkyl carbonyl amino, lower alkoxy carbonyl lower alkyl amino, hydroxy lower alkyl amino, carbamoyl amino, lower alkoxy lower alkyl amino, lower alkyl sulfonyl amino, and cycloalkyl amino, and the like. The term, "that may be substituted" is defined as for the above-discussed "that may be substituted" for "alkyl". Said substituent may together with the N-atom of the amino form a heterocycle.

The above-described "mono-lower alkylamino", of which the lower alkyl has the same meaning as the aforementioned definition, includes, for example, mono-lower alkylamino groups having a carbon number of 2-20, such as methylamino, ethylamino, propylamino, isopropylamino, butylamino, isobutylamino, sec-butylamino, t-butylamino, pentylamino, isopentylamino, and hexylamino, and the like.

The above-described "di-lower alkylamino", of which the lower alkyl has the same meaning as the aforementioned definition, includes, for example, di-lower alkylamino groups having a total carbon number of 2-20, such as di-methylamino, ethylmethylamino, di-ethylamino, methylpropylamino, ethylpropylamino, isopropylmethylamino, isopropylethylamino, butylmethylamino, butylethylamino, isobutylmethylamino, and isobutylethylamino, and the like.

The above-described "lower alkyl carbonylamino", of which the lower alkyl has the same meaning as the aforementioned definition, includes, for example, alkyl carbonylamino groups having a carbon number of 2-7, such as methyl carbonylamino, ethyl carbonylamino, propyl carbonylamino, isopropyl carbonylamino, butyl carbonylamino, isobutyl carbonylamino, sec-butyl carbonylamino, t-butyl carbonylamino, pentyl carbonylamino, and isopentyl carbonylamino, and the like.

As used herein, the term, "imino" refers to a $CR_{13}$—NH—$CR_{14}$ group or $CR_{15}$=NH group, wherein $R_{13}$-$R_{15}$ refer to hydrogen, the aforementioned "alkyl", "aralkyl", "acyl", aryl sulfonyl that may be substituted (such as alkoxyphenyl sulfonyl), alkyl sulfonyl, carbamoyl, and the like.

As used herein, examples of the substituents on "imino that may be substituted" include hydroxy, alkoxy, "alkyl", "aralkyl", "acyl", aryl sulfonyl that may be substituted (such as alkoxyphenyl sulfonyl), alkyl sulfonyl, and carbamoyl, and the like. The "imino that may be substituted" includes, for example, imino, hydroxyimino (oxime), methylimino, ethylimino, dimethylimino, benzylimino, benzoyloxyimino, benzoylimino, acetylimino, propionylimino, tert-butoxy carbonylimino, methyl sulfonylimino, and 4-methoxyphenyl sulfonylimino, and the like. Especially preferred are imino, methylimino, dimethylimino, diethylimino, and acetylimino.

As used herein, the term, "amidino that may be substituted" refers to —C(=NH)NH$_2$ group, and the substituent on the "amidino that may be substituted" is as defined for the above-discussed "that may be substituted" for "alkyl", and any nitrogen atoms may be substituted.

As used herein, the term, "saturated or unsaturated alicyclic hydrocarbon groups that may be substituted" includes, for example, cycloalkyl, cycloalkenyl, cycloalkynyl, cycloalkadienyl, and the like. These include, for example, cycloalkyl groups having a carbon number of 3-20, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1] nonyl, and bicyclo[4.2.1]nonyl, bicyclo[4.3.1]decyl, adamantyl, and the like. Examples of the above-described cycloalkenyl groups include, for example, cycloalkenyl groups having a carbon number of 4-20, such as 2-cyclopentyl-1-yl, 3-cyclopentene-1-yl, 2-cyclohexene-1-yl, and 3-cyclohexene-1-yl, and the like. Examples of the above-described cycloalkadienyl groups include, for example, cycloalkadienyl groups having a carbon number of 4-20, such as 2,4-cyclopentadiene-1-yl, 2,4-cyclohexadiene-1-yl, and 2,5-cyclohexadiene-1-yl, and the like.

As used herein, the term, "aryl that may be substituted" includes, for example, aryl groups having a carbon number of 6-20, such as phenyl, indenyl, naphthyl, (1-naphthyl, and 2-naphthyl, etc.), anthryl, phenanthryl, acenaphthylenyl, and fluorenyl (9-fluorenyl, and 1-fluorenyl, etc.), and the like. The (substituted) aryl comprises both non-substituted aryl and substituted aryl.

As used herein, the term, the substituents and substitution positions on the benzene ring of the "phenyl that may be substituted" includes, for example, 2-, 3-, or 4-fluoro; 2-, 3-, or 4-chloro; 2-, 3-, or 4-bromo; 2-, 3-, or 4-iodo; 2-, 3-, or 4-methyl; 2,3-, 2,4-, or 2,5-dimethyl; 2,6-, 3,4-, or 3,5-dimethyl; 2,3,4-, 2,3,5-, 2,3,6-, 2,4,5-, 2,4,6-, or 3,4,5-trimethyl; 2-, 3-, or 4-ethyl; 2-, 3-, or 4-propyl; 2-, 3-, or 4-trifluoromethyl; 2-, 3-, or 4-methoxy; 2,3-, 2,4-, 2,5-, 2,6-, 3,4-, or 3,5-dimethoxy; 2,3,4-, 2,3,5-, 2,3,6-, 2,4,5-, 2,4,6-, or 3,4,5-trimethoxy; 2-, 3-, or 4-ethoxy; 2-, 3-, or 4-propoxy; 2-, 3-, or 4-trifluoromethoxy; 2-, 3-, or 4-cyano; 2-, 3-, or 4-nitro; and any available combinations of these substituents and substitution positions.

As used herein, the heterocyclic group in the term, "heterocyclic group that may be substituted" refers to a heterocyclic group containing at least one heteroatom of oxygen, sulfur, or nitrogen as an atom constituting the ring system, and includes, for example, aromatic monocyclic heterocyclic groups, and bicyclic or tricyclic, aromatic fused heterocyclic groups, and non-aromatic monocyclic heterocyclic groups, and the like. Specific examples of the monocyclic heterocyclic groups include, for example, furyl, thienyl, pyrronyl, oxazolyl, isooxazolyl, thiazolyl, isothiazolyl, imidazolyl, pyrazolyl, 1,2,3-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, quinolyl, piperazinyl, piperidinyl, and pyrrolidinyl, and the like. Specific examples of the bicyclic or tricyclic aromatic fused heterocyclic groups include, for example, benzofuranyl, isobenzofuranyl, benzo [b]thienyl, indolyl, isoindolyl, 1H-indazolyl, benzoimidazolyl, benzooxazolyl, 1,2-benzoisooxazolyl, benzothiazolyl, 1,2-benzoisothiazolyl, 1H-benzotriazolyl, quinolyl, iso quinolyl, cinnonyl, quinazolinyl, quinoxalinyl, phthalazinyl, naphthyridinyl, purinyl, pteridinyl, carbazolyl, α-carbolynyl, β-carbolynyl, γ-carbolynyl, acridinyl, phenoxazinyl, phenothiazinyl, phenazinyl, phenoxathinyl, thianthrenyl, phenanthrydinyl, phenanthrolynyl, indolizinyl, pyrrolo[1,2-b]pyridazinyl, pyrrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-a]pyridazinyl, and the like. Preferred heterocyclic groups include those having one hydrogen removed from the following:

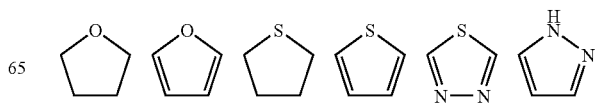

wherein the deletion position of the hydrogen may be any chemically available position, and may be on the aromatic ring or non-aromatic ring. More preferably, it is a 5-7 membered N-atom containing non-aromatic ring, for example, piperazinyl, piperidinyl, or pyrrolidinyl.

As used herein, the term, "heterocyclicoxy that may be substituted" includes specifically a group represented by the formula $R_{16}O$— (wherein, in the formula, $R_{16}$ represents a heterocyclic group that may be substituted), and the like.

Preferred specific examples of the substituent in "saturated or unsaturated alicyclic hydrocarbon group that may be substituted", "aryl that may be substituted", and "heterocyclic group that may be substituted" include, for example, lower alkyl that may be substituted, lower alkenyl that may be substituted, lower alkynyl that may be substituted, halogen, hydroxy, lower alkoxy that may be substituted, aryloxy that may be substituted, monosubstituted carbonyloxy that may be substituted, carbamoyl that may be substituted, diazo, cyano, amino that may be substituted, imino that may be substituted, amidino that may be substituted, azido, nitro, nitroso, mercapto, monosubstituted thio that may be substituted, monosubstituted thioxy, monosubstituted sulfinyl that may be substituted, monosubstituted sulfonyl that may be substituted, sulfo, saturated or unsaturated alicyclic hydrocarbon groups that may be substituted, aryl that may be substituted, heterocyclic groups that may be substituted, heterocyclic oxy that may be substituted, acyl that may be substituted, and trisubstituted silyl, and the like. The number of the substituents, if any, is one to three, preferably one. The position of the substituent is not specifically limited. Among the above-described substituents, preferred are hydroxy, lower alkyl, lower alkoxy, lower alkenyloxy, lower alkyl carbonyloxy, or lower alkyl substituted with hydroxy, lower alkoxy or lower alkyl carbonyl group.

Preferred examples of the above-described "lower alkyl carbonyl", of which the lower alkyl has the same meaning as the aforementioned definition, include, for example, alkanoyl groups having a carbon number of 2-6, such as acetyl, propionyl, butyryl, isobutyryl, valeryl, isovaleryl, pivaloyl, and hexanoyl, and the like.

Preferred examples of the above-described "lower alkoxy carbonyl", of which the lower alkoxy has the same meaning as the aforementioned definition, include, for example, alkoxy carbonyl groups having a carbon number of 2-7, such as methoxy carbonyl, ethoxy carbonyl, n-propoxy carbonyl, and n-butoxy carbonyl, and the like.

Other substituents are defined as for the substituents of the "aliphatic hydrocarbon that may be substituted".

As used herein, the term, "mono-substituted thio that may be substituted" includes specifically a group represented by the formula $R_{17}S$— (wherein, in the formula, $R_{17}$ represents a hydrocarbon group or heterocyclic group that may be substituted), and the like. The "mono-substituted thio" includes, for example, mono-substituted thio groups having a carbon number of 1-6, such as methylthio, ethylthio, propylthio, isopropylthio, butylthio, isobutylthio, neobutylthio, t-butylthio, pentylthio, and hexylthio, and the like.

As used herein, the term, "mono-substituted thioxy that may be substituted" includes specifically a group represented by the formula $R_{18}SO$— (wherein, in the formula, $R_{18}$ represents a hydrocarbon group or heterocyclic group that may be substituted), and the like.

As used herein, the term, "mono-substituted sulfonic acid that may be substituted" includes specifically a group represented by the formula $R_{19}S(O)_2$— (wherein, in the formula, $R_{19}$ represents a hydrocarbon group or heterocyclic group that may be substituted), and the like.

As used herein, the term, "mono-substituted sulfunic acid that may be substituted" includes specifically a group represented by the formula $R_{20}S(O)$— (wherein, in the formula, $R_{20}$ represents a hydrocarbon group or heterocyclic group that may be substituted), and the like.

As used herein, the "hydrocarbon groups" in the "hydrocarbon group or heterocyclic group that may be substituted" represented by $R_{17}$-$R_{20}$ include, for example, non-cyclic groups such as straight chain or branched aliphatic hydrocarbon groups (alkyl, alkenyl, and alkynyl groups, etc.), and cyclic groups such as saturated and unsaturated alicyclic hydrocarbon groups (cycloalkyl, cycloalkenyl, and cycloalkadienyl groups, etc.), and aryl groups, and the like.

Examples of the alkyl, alkenyl, and alkynyl groups in the above-described "hydrocarbon group" include the same groups as those illustrated for the "aliphatic hydrocarbon group that may be substituted".

Examples of the cycloalkyl, cycloalkenyl, and cycloalkadienyl groups in the above-described "hydrocarbon group" include the same groups as those illustrated for the "aliphatic hydrocarbon group that may be substituted".

Examples of the aryl groups in the above-described "hydrocarbon group" include, for example, aryl groups having a carbon number of 6-20, such as phenyl, indenyl, naphthyl (1-naphthyl, and 2-naphthyl, etc.), anthryl, phenanthryl, acenaphthylenyl, and fluorenyl (9-fluorenyl, and 1-fluorenyl, etc.), and the like.

The "heterocyclic group" in the above-described "hydrocarbon group or heterocyclic group that may be substituted" refers to a heterocyclic group containing at least one heteroatom of oxygen, sulfur, or nitrogen as an atom constituting the ring system, preferably, an aromatic heterocyclic group, and includes, for example, aromatic monocyclic heterocyclic groups, and bicyclic or tricyclic aromatic fused heterocyclic groups, and the like. Specific examples of the monocyclic heterocyclic groups include, for example, furyl, thienyl, pyrronyl, oxazolyl, isooxazolyl, thiazolyl, isothiazolyl, imidazolyl, pyrazolyl, 1,2,3-oxadiazolyl, 1, 3, 4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, and quinolyl, and the like. Specific examples of the bicyclic or tricyclic aromatic fused heterocyclic groups include, for example, benzofuranyl, isobenzofuranyl, benzo☐b☐thienyl, indolyl, isoindolyl, 1H-indazolyl, benzoimidazolyl, benzooxazolyl, 1,2-benzoisooxazolyl, benzothiazolyl, 1,2-benzoisothiazolyl, 1H-benzotriazolyl, quinolyl, iso quinolyl, cinnonyl, quinazolinyl, quinoxalinyl, phthalazinyl, naphthyridinyl, purinyl, pteridinyl, carbazolyl, α-carbolynyl, β-carbolynyl, γ-carbolynyl, acridinyl, phenoxazinyl, phenothiazinyl, phenazinyl, phenoxathinyl, thianthrenyl, phenanthrydinyl, phenanthrolynyl, indolizinyl, pyrrolo[1,2-b]pyridazinyl, pyrrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-a]pyridazinyl, and the like. Among others, more preferred are heterocyclic groups containing only an oxygen atom as a cyclic atom, such as furyl, benzo[b]furyl, 2H-pyran-3-yl, isobenzofuran, 2H-cromene-3-yl, xanthenyl, chromanyl, isochromanyl, 2H-furo[3,2-b]pyran, cyclopenta[b]pyran, and 2H-benzopyranyl, and the like.

The substituents on the above-described "hydrocarbon group or heterocyclic group that may be substituted" include the same groups as the substituents on the "saturated and unsaturated alicyclic hydrocarbon groups", "aryl that may be substituted" and "heterocyclic group that may be substituted" that are the substituents on the "aliphatic hydrocarbon group that may be substituted".

Preferred specific examples of the "aliphatic hydrocarbon group that may be substituted" include, in addition to the especially preferred specific examples as described below, for example, isopentenyl, 2-hydroxy-3-methyl-butyl, 3-hydroxy-2-phenylpropyl, 3-(2,4-dihydroxyphenyl carbonyl)butyl, 2-methoxy-3-methyl-butyl, 3-methoxy-2-phenylpropyl, 2-(2-butenyloxy)-3-methyl-butyl, 3-(2,4-dihydroxyphenyl)propyl, 3-(2,4-dimethoxyphenyl carbonyl)butyl, 2-hydroxy-butyl, 2-hydroxy-3-methyl-pentyl, 2-methoxy-butyl, and 2-methoxy-3-methyl-pentyl, and the like.

Especially preferred examples of the "aliphatic hydrocarbon group that may be substituted" include, for example, methyl, ethyl, n-propyl, i-propyl, n-butyl, i-butyl, n-pentyl, 3-methylbutyl, 2,2-dimethylpropyl, n-hexyl, 3-methylbutyl, 4-methylpentyl, n-heptyl, n-octyl, n-nonyl, tetrahydrogeranyl, n-decyl, n-pentadecyl, trifluoromethyl, 2-propenyl, 2-butenyl, 3-butenyl, 2-ethyl-1-butenyl, 3-methyl-2-butenyl, 1-pentenyl, 2-pentenyl, 4-pentenyl, geranyl, 2-propynyl(propargyl), and 2-butynyl, and the like.

As used herein, the symbol "*" refers to the presence of an asymmetric carbon, and to either R or S stereoisomers, or the mixtures thereof. The compound of the present invention comprises various stereoisomers, all of which are included in the compound of the present invention. Also, its geometric isomers, if any, may be either cis- or trans-isomers.

As used herein, H represents hydrogen, OH represents hydroxy, Me represents methyl, Et represents ethyl, i-Pr represents isopropyl, TBS represents tert-butyldimethylsilyl, nd SEM represents 2-(trimethylsilyl)ethoxymethyl. Bzl represents benzyl, Me represents methyl, Ph represents phenyl, MOM represents methoxymethyl, TMS represents trimethylsilyl, prenyl represents prenyl group (i.e., 3-methyl-2-butenyl group), "prenyloxy" represents prenyloxy, "OC$_6$H$_{11}$-c" represents cyclohexyloxy, "OC$_6$H$_{11}$-n" represents a straight chain hexyloxy, Ts represents p-toluenesulfonyl, TBDPS represents tert-butyldiphenylsilyl, Bu$^t$ represents tert-butyl, $^i$Pr represents isopropyl, and "picolyloxy" represents picolyloxy. Also, "( )$_2$" represents di-substitution. The term (substituted) in (substituted) alkyl, or (substituted)aryl, or the like is used to represent both the substituted and unsubstituted functional group.

The compound of the present invention having an i-hydrogen on the substituent includes the following tautomers:

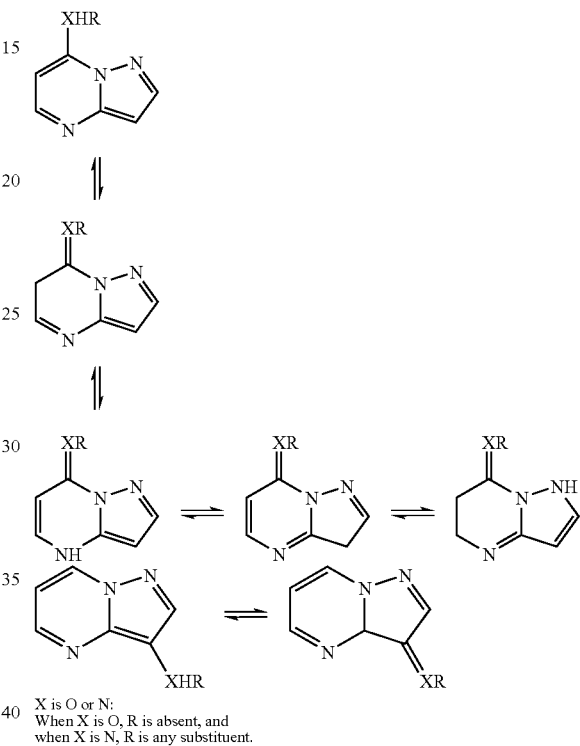

X is O or N;
When X is O, R is absent, and
when X is N, R is any substituent.

These tautomers are within the scope of the present invention.

The present compound (Ia) is preferably compound (I), and more preferably compound (I-1). In compound (Ia), $R_{1a}$ is preferably carbamoyl that may be substituted, and more preferably —CONR$_1$R$_2$, wherein $R_{2a}$ is preferably hydrogen.

When any combination of $R_{1a}$, $R_{2a}$, and $R_3$-$R_5$ together forms a ring structure in compound (Ia), said ring comprises the aforementioned heterocyclic ring that may be substituted, and hydrocarbon ring that may be substituted, with 5-7 membered rings being preferred.

One embodiment of the present invention, when the compound is represented by the above-described formula (I), is a compound, wherein R$_1$ is hydrogen; R$_2$ is an aryl that may be substituted; R$_3$ is hydrogen, or amino that may be substituted; R$_4$ is hydrogen; R$_5$ is an aryl that may be substituted.

A preferred embodiment of the present invention, when the compound is represented by the above-described formula (I), is a compound, wherein R$_1$ is hydrogen; R$_2$ is an aryl that may be substituted with one or more substitutents selected from the group consisting of a heterocyclic group that may be substituted, lower alkylcarbonyl, cycloalkyl, lower alkyl, amino that may be substituted, and phenyl; R$_3$ is hydrogen, or amino that may be substituted; R$_4$ is hydrogen; R$_5$ is an aryl that may be substituted with one or more substitutents selected from the group consisting of halogen, halogenated lower alkyl, aryl lower alkyloxy, lower alkyl, lower alkoxy, hydroxy, lower alkylthio, phenyl, phenyloxy, phenyl lower alkyl, phenyl lower alkyloxy, phenyl lower alkylamino, phenyl lower alkylthio, phenyl lower alkenyl, phenyl carbamoyl, amino, cycloalkyl lower alkyloxy, and heteroaryl lower alkyloxy.

A more preferred embodiment of the present invention, when the compound is represented by the above-described formula (I), is a compound, wherein $R_1$ is hydrogen; $R_2$ is a phenyl substituted with one or more substitutents selected from the group consisting of a heterocyclic group that may be substituted, lower alkylcarbonyl, cycloalkyl, lower alkyl, amino that may be substituted, and phenyl; $R_3$ is hydrogen, or amino that may be substituted; $R_4$ is hydrogen; $R_5$ is a phenyl substituted with one or more substitutents selected from the group consisting of halogen, halogenated lower alkyl, aryl lower alkyloxy, lower alkyl, lower alkoxy, hydroxy, lower alkylthio, phenyl, phenyloxy, phenyl lower alkyl, phenyl lower alkylamino, phenyl lower alkylthio, phenyl lower alkenyl, phenyl carbamoyl, amino, cycloalkyl lower alkyloxy, and heteroaryl lower alkyloxy.

In the above-described embodiments, $R_2$ is preferably a phenyl substituted with a heterocyclic group that may be substituted, more preferably, 5-7 membered N-atom containing non-aromatic heterocyclic group that may be substituted (for example, piperazino, piperizino, and pyrrolizino). In this case, the substituent "that may be substituted" may be present in any position on the heterocycle and/or phenyl. The substituent on the amino that may be substituted in $R_3$ may be a lower alkylene (for example, —$CH_2$—$CH_2$—$CH_2$—$CH_2$—, —$CH_2$—$CH_2$—O—$CH_2$—$CH_2$—) that may be intervened with a heteroatom, mono- or di-lower alkyl, phenyl (substituent: halogen, etc.) that may be substituted, and the like.

A further preferred embodiment of the present invention, when the compound is represented by the above-described formula (I), is a compound, wherein $R_1$ is hydrogen; $R_2$ is selected from the group consisting of 2-, 3- and 4-piperadinophenyl that may be substituted, 2-, 3-, and 4-pyrrolizinophenyl that may be substituted, and 2-, 3- and 4-piperidinophenyl that may be substituted; $R_3$ is hydrogen; $R_4$ is hydrogen; $R_5$ is a phenyl substituted with one or more substitutents selected from the group consisting of halogen, halogenated lower alkyl, lower alkyl, lower alkoxy, hydroxy, lower alkylthio, phenyl, phenyloxy, phenyl lower alkyl, phenyl lower alkyloxy, phenyl lower alkylamino, phenyl lower alkylthio, phenyl lower alkenyl, phenyl carbamoyl, amino, cycloalkyl lower alkyloxy, and heteroaryl lower alkyloxy.

The "salt" for the intended compound of the present invention is preferably a pharmaceutically acceptable salt, and includes, for example, inorganic base salts, organic base salts, inorganic acid salts, organic acid salts, and basic or acidic amino acid salts, and the like. The inorganic base salts include alkali metal salts such as sodium salts, potassium salts, and the like; alkaline earth metal salts such as calcium salts, magnesium salts, barium salts, and the like; and aluminum salts, ammonium salts, and the like. The organic base salts include salts with trimethylamine, triethylamine, pyridine, picoline, ethanolamine, diethanolamine, triethanolamine, dicyclohexylamine, N,N'-dibenzylethylenediamine, and the like. The inorganic acid salts include salts with hydrochloric acid, hydrofluoric acid, hydrobromic acid, nitric acid, sulfuric acid, phosphoric acid, perchloric acid, hydroiodic acid, and the like. The organic acid salts include salts with formic acid, acetic acid, trifluoroacetic acid, fumaric acid, oxalic acid, tartaric acid, maleic acid, citric acid, succinic acid, malic acid, mandelic acid, ascorbic acid, lactic acid, gluconic acid, methanesulfonic acid, p-tolunesulfonic acid, benzenesulfonic acid, and the like. The basic amino acid salts include salts with arginine, lysine, ornithine, and the like. The acidic amino acid salts include salts with aspartic acid, glutamic acid, and the like.

When the compound of the present invention has one or more chiral centers, it may be present as an optically active substance. Similarly, when said compound has an alkenyl or alkenylene, there may be cis- or trans-isomers. Its R- and S-isomers, mixtures of the cis- or trans-isomers, and mixtures of the R- and S-isomers including racemic mixtures are within the scope of the present invention. An asymmetric carbon atom may be present in a substituent such as alkyl group. Such isomers and their mixtures are within the scope of the present invention. When a specific stereoisomer is desirable, the pre-divided starting material having an asymmetrical center may be subjected to a stereospecific reaction using a technique known to those skilled in the art, or a mixture of the stereoisomers may be prepared, and then divided by a known technique.

The prodrug is a derivative of the compound with NAD(P)H oxydase inhibiting activity that has a chemically or metabolically decomposable group, and a compound that may be converted into a pharmaceutically active compound in vivo by solvolysis under physiological conditions. Although both the acid and base derivatives of said compound may be active, the acid derivative is advantageous in terms of the solubility, tissue affinity, and controlled release in mammals (Bungard, H., Design of Prodrugs, pp.7-9, 21-24, Elsevier, Amsterdam 1985). For example, prodrugs comprising esters prepared by reacting the original acidic compounds with suitable alcohols, or acid derivatives such as amides prepared by reacting the original acidic compounds with suitable amines are known to those skilled in the art. Simple aliphatic or aromatic esters that are derived from the acidic groups present in said compounds are preferred prodrugs. More preferred are C1-C6 alkyl esters (such as methyl esters, ethyl esters, n-propyl esters, isopropyl esters, n-butyl esters, isobutyl esters, tert-butyl esters), morpholinoethyl esters, and N,N-dirthylglycolamide esters of the acidic groups. For example, a prodrug that is the methyl ester may be prepared by reacting the sodium salt of the compound represented by the general formula (Ia) with methyl iodide (Aldrich Chemical Co., Milwaukee, Wis. USA; available as lot No. 28, 956-6) in a solvent such as dimethylformamide. For example, a prodrug that is the ethyl ester may be prepared by reacting the sodium salt of the compound represented by the general formula (Ia) with ethyl iodide (Aldrich Chemical Co., Milwaukee, Wis. USA; available as lot No. I-778-0) in a solvent such as dimethylformamide. A prodrug that is the N,N-dirthylglycolamide ester may be prepared by reacting the sodium salt of the compound represented by the general formula (Ia) with 2-chloro-N,N-diethyl-acetamide (Aldrich Chemical Co., Milwaukee, Wis. USA; available as lot No. 25, 099-6) in a solvent such as dimethylformamide. A prodrug that is the morpholinoethyl ester may be prepared by reacting the sodium salt of the compound represented by the general formula (Ia) with 4-(2-chloroethyl)-morpholine hydrochloride (Aldrich Chemical Co., Milwaukee, Wis. USA; available as lot No. C4, 220-3) in a solvent such as dimethylformamide. In some cases, double ester-type prodrugs such as the (acyloxy) alkyl esters or ((alkoxycarbonyl)oxy) alkyl esters may be prepared.

By "pharmaceutically acceptable" it is meant that the so defined substance be compatible with the other ingredients of the formulation, and not deleterious to the recipient thereof.

Illustrative examples of the "solvate" of the intended compound of the present invention include the hydrates and alcoholates with the hydrates being preferred including hydrated salts, and specifically include monohydrates, dihydrates, hexahydrates, and the like.

The compositions include pharmaceutical compositions (including quasi-drugs), animal drug compositions (livestock drugs, veterinary drugs, fishery drugs, and the like), and the like. In other words, they are useful as NAD(P)H inhibitors in human and animal, and diagnotic drugs that are used to diagnose NAD(P)H-related diseases.

The diseases to be treated using the composition of the present invention include inflammation, pulmonary circulation disorders, ischemic heart disease, (such as coronary artery diseases), cerebral circulation disorders (such as brain edema, brain infarction), arteriosclerosis (such as atherosclerosis), diabetic complications, hypertension, proliferative diseases, and the like.

The following illustrate a general process for preparing the pharmaceutical composition of the present invention.

The compound of the present invention may be combined with a physiologically acceptable carrier, and orally or parenterally administered as solid preparations such as tablets, capsules, granules, powders, suppositories, or liquid preparations such as syrups, injectables, suspensions, solutions, sprays, and the like. The physiologically acceptable carriers include excipients, lubricants, binders, disintegrants, disintegration inhibitors, absorption accelerators, adsorbents, wetting agents, and dissolution aids, stabilizers for solid preparations; and solvents, dissolution aids, suspending agents, isotonic agents, buffers, analgesic agents, and the like for liquid preparations. Also, preparation additives such as preservatives, antioxidants, coloring agents, sweeteners, and the like may optionally be used. Also, other substances that inhibit NAD(P)H may be combined with the composition of the present invention. The routes for parenteral administration includes intravenous injection, intramuscular injection, nasal, rectal, vaginal, transdermal, and the like.

The excipients for the solid preparations include, for example, glucose, lactose, sucrose, D-mannitol, crystallized cellulose, starch, calcium carbonate, light anhydrous silicic acid, sodium chloride, kaolin, and urea, and the like.

The lubricants for the solid preparations include, for example, magnesium stearate, calcium stearate, powdered boric acid, colloidal silicic acid, talc, and polyethylene glycol, and the like.

The binders for the solid preparations include, for example, water, ethanol, propanol, saccharose, D-mannitol, crystallized cellulose, dextrin, methyl cellulose, hydroxypropyl cellulose, hydroxypropyl methyl cellulose, carboxymethyl cellulose, starch solutions, gelatin solutions, polyvinyl pyrrolidone, calcium phosphate, potassium phosphate, and shellac, and the like.

The disintegrants for the solid preparations include, for example, starch, carboxymethyl cellulose, carboxymethyl cellulose calcium, agar powder, laminaran, croscarmellose sodium, carboxymethyl starch sodium, sodium alginate, sodium bicarbonate, calcium carbonate, polyoxyethylene sorbitan fatty acid esters, sodium laurylsulfate, starch, monoglyceride stearate, lactose, and fibrin calcium glycolate, and the like.

Preferred examples of the disintegration inhibitors for the solid preparations include, hydrogenated oils, saccharose, stearin, cocoa butter, and hardened oils, and the like.

The absorption accelerators for the solid preparations include, for example, quaternary ammonium base, and sodium laurylsulfate, and the like.

The adsorbents for the solid preparations include, for example, starch, lactose, kaolin, bentonite, and colloidal silicic acid, and the like.

The wetting agents for the solid preparations include, for example, glycerin, starch, and the like.

The dissolution aids for the solid preparations include, for example, arginine, glutamic acid, aspartic acid, and the like.

The stabilizers for the solid preparations include, for example, human serum albumin, lactose, and the like.

When a tablet or pill is used as the solid preparation, it may optionally be coated with a film of gastric or enteric substance (such as saccharose, gelatin, hydroxypropyl cellulose, hydroxypropyl methylcellulose phthalate, and the like). The tablets include those having optionally an ordinary tablet skin, for example, dragees, gelatin-coated tablets, enterically coated tablets, film coated tablets, double coated tablets, and multi-layered tablets. The capsules include hard capsules and soft capsules. In order to shape a suppository, for example, a higher alcohol, a higher alcohol ester, a semisynthetic glyceride, and the like may be added, in addition to those additives listed above.

Preferred examples of the solvents for the liquid preparations include injection water, alcohol, propylene glycol, macrogol, sesame oil, and corn oil, and the like.

Preferred examples of the dissolution aids for the liquid preparations include, for example, polyethylene glycol, propylene glycol, D-mannitol, benzyl benzoate, ethanol, trisaminomethane, cholesterol, triethanolamine, sodium carbonate, and sodium citrate, and the like.

Preferred examples of the suspensions for the liquid preparations include, for example, surfactants such as stearyl triethanolamine, sodium laurylsulfate, lauryl aminopropionic acid, lecithin, benzalkonium chloride, benzethonium chloride, and glycerin monostearate, and the like; and hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, and the like.

Preferred examples of the isotonic agents for the liquid preparations include, for example, sodium chloride, glycerin, D-mannitol, and the like.

Preferred examples of the buffers for the liquid preparations include, for example, phosphates, acetates, carbonates, and citrates, and the like.

Preferred examples of the analgesic agents for the liquid preparations include, for example, benzyl alcohol, benzalkonium chloride, and procain hydrochloride, and the like.

Preferred examples of the preservatives for the liquid preparations include, for example, p-oxybenzoic acid esters, chlorobutanol, benzyl alcohol, 2-phenylethyl alcohol, dehydroacetic acid, sorbic acid, and the like.

Preferred examples of the antioxidants for the liquid preparations include, for example, sulfites, ascorbic acid, α-tocopherol, and cysteine, and the like.

When the liquid preparation is prepared as an injectable, the liquid formulation and suspension are preferably sterilized, and isotonic with blood. Ordinarily, it is sterilized by filtration with filter having a pore size which excludes bacteria, etc., blending with a bactericide, or irradiation. Further, after such a treatment, it may be made solid by freeze-drying, and immediately before use sterile water or sterile injectable diluent (such as an aqueous lidocaine hydrochloride solution, physiological saline, an aqueous dextrose solution, ethanol, or mixtures thereof) may be added.

Additionally, the pharmaceutical composition may optionally contain coloring agents, preservatives, flavoring agents, corrigents/odor improvers, etc., or other agents.

As used herein, "administrating" means administrating a compound of the present invention or a medical composition comprising the compound alone or in combination with other therapeutic agents. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as separate intravenous lines into the same individual. Administration "in combination" further includes the separate administration of one of the compounds or agents given first, followed by the second.

As used herein, "administering NAD(P)H oxidase inhibitor before indication of diseases related to NAD(P)H are observed" means that NAD(P)H oxidase inhibitor is administered, for example, before a condition or an indication of a disease related to NAD(P)H is confirmed, according to a diagnosis of a medical doctor as discussed above, or that NAD(P)H oxidase inhibitor is administered before each patient recognizes the condition or the indication.

As used herein, "hypertension" means accelerated hypertension, adrenal hypertension, benign hypertension, borderline hypertension, essential hypertension, gold blood hypertension, idiopathic hypertension, labile hypertension, malignant hypertension, pale hypertension, portal hypertension, postpartum hypertension, primary hypertension, pulmonary hypertension, renal hypertension, renovascular hypertension, secondary hypertension or systemic hypertension, or the related diseases which require the administration to a mammal in a therapeutic effective dose of a compound expressed by the general formula (Ia) in a sufficient dose to inhibit NAD(P)H oxidase.

As used herein, "diabetic complication" means diabetic nephropathy, diabetic neuropathy or diabetic retinopathy, or the related diseases which require the administration to a mammal in a therapeutic effective dose of a compound expressed by the general formula (Ia) in a sufficient dose to inhibit NAD(P)H oxidase.

As used herein, "arteriosclerosis" means coronary arteriosclerosis, hyperplastic arteriosclerosis, hypertensive arteriosclerosis, medial arteriosclerosis, Monckeberg arteriosclerosis, tuberous arteriosclerosis, arteriosclerosis obliterans, peripheral arteriosclerosis or senile arteriosclerosis, or the related diseases which require the administration to a mammal in a therapeutic effective dose of a compound expressed by the general formula (Ia) in a sufficient dose to inhibit NAD(P)H oxidase.

As used herein, "coronary artery disease" means angina pectoris, coronary artery aneurysm, coronary arteriosclerosis, coronary thrombosis, coronary vasospasm, myocardial infarction or stunned myocardium, or the related diseases which require the administration to a mammal in a therapeutic effective dose of a compound expressed by the general formula (Ia) in a sufficient dose to inhibit NAD(P)H oxidase.

As used herein, "stroke" means hypertensive intracerebral hemorrhage, cerebral infarction, transient ischemic attack or subarachnoid hemorrhage, or the related diseases which require the administration to a mammal in a therapeutic effective dose of a compound expressed by the general formula (Ia) in a sufficient dose to inhibit NAD(P)H oxidase.

As used herein, "ischemic disease" means myocardial infarction or attack, or the related diseases which require the administration to a mammal in a therapeutic effective dose of a compound expressed by the general formula (Ia) in a sufficient dose to inhibit NAD(P)H oxidase.

As used herein, "neurodegenerative disorders" means Alzheimer disease, Parkinson disease, amyotrophic lateral sclerosis, retinitis pigmentosa, cerebellar degeneration, brain tumor or previously related diseases, or the related diseases which require the administration to a mammal in a therapeutic effective dose of a compound expressed by the general formula (Ia) in a sufficient dose to inhibit NAD(P)H oxidase.

As used herein, "pulmonary circulation disorders" means pulmonary artery thrombosis, embolism, pulmonary edema, pulmonary hypertension or chronic cor pulmonale, or the related diseases which require the administration to a mammal in a therapeutic effective dose of a compound expressed by the general formula (Ia) in a sufficient dose to inhibit NAD(P)H oxidase.

As used herein, "nephritis" means immune complex glomerulonephritis, glomerulonephritis, immune-related glomerulonephritis (e.g., proliferative glomerulonephritis), chronic glomerulonephritis or proliferative glomerulonephritis, or the relatedi diseases which require the administration to a mammal in a therapeutic effective dose of a compound expressed by the general formula (Ia) in a sufficient dose to inhibit NAD(P)H oxidase.

As used herein, "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by the general formula (Ia) in a sufficient dose to inhibit NAD(P)H oxidase.

As used herein, "inflammatory disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, tuberculous arthritis, viral arthritis, arthritis by bacteria, syphilitic arthritis, Lyme disease, arthritis induced by "angiitis syndrome", polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Behat disease, systemic autoimmune disease erythematosus or diseases like relapsing polychondritis, or the related diseases which require the administration to a mammal in a therapeutic effective dose of a compound expressed by the general formula (Ia) in a sufficient dose to inhibit NAD(P)H oxidase.

As used herein, "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, bladder cancer or epithelial cancer) or the related diseases which require the administration to a mammal in a therapeutic effective dose of a compound expressed by the general formula (Ia) in a sufficient dose to inhibit NAD(P)H oxidase.

Various delivery systems are known and can be used to administer the compounds in the present invention (e.g., liposomes, particles, microcapsules, etc.). Intracutaneous, intramuscular, intraperitoneal, intravenous, subcutaneous, intranasal, intradural and oral routes are given as introduction methods, but not limited to those routes. Compounds or compositions can be administered by optional favorable routes (e.g., absorption through epithelium or mucosal lining (e.g., oral mucosa, rectal mucosa, intestinal mucosa, etc.) by infusion or bolus injection) and together with other biologically active agents. The administration can be systemically or locally. Furthermore, it is desirable that pharmaceutical compounds or compositions in the present invention are introduced to central nervous system by optional appropriate routes (including intraventricular and intraspinal injections; intraventricular injection can be easily conducted with a ventricular catheter fitted to a reserver such as Ommaya reserver). For example, pulmonary administration is also available by the prescription using an inhaler or atomizer and aerosolized agents.

The dose of the compound of the present invention may be varied depending on the age, weight and condition of the subject, or the administration procedure, and is not specifically limited, but for an adult, it may ordinarily be oral administration of from 0.1 mg-1 g, 1 mg-100 mg, 0.1 mg-10 mg, etc., and parenteral administration of 0.01 mg-1 g, preferably 0.01 mg-100 mg, 0.1 mg-100 mg, 1 mg-100 mg, 0.1 mg-10 mg, etc.

BEST MODES FOR CARRYING OUT THE INVENTION

The compounds used in the present invention, or salts or solvates thereof may be prepared by known techniques. Specific examples of said techniques include the following manufacturing process or similar processes. A process for the manufacture of the compound (I) is illustrated as a process for the manufacture of the compound (Ia).

The compound of the present invention represented by the formula (I) may be synthesized from the following compound A and any suitable amine:

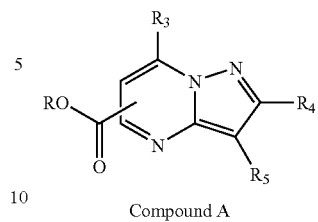

Compound A

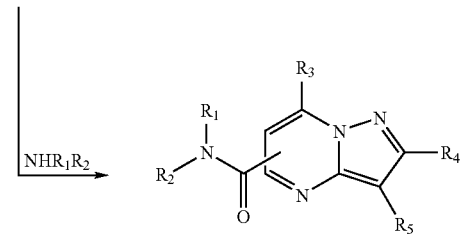

Said reaction may be carried out according to amidation conditions well known to those skilled in the art.

The substituents $R_3$-$R_5$ in compound A may preferably be derived from halogen substituents, and the like. For example, the halogen substituents may be replaced by hydrogen atoms under a reaction condition using Pd/C and $H_2$, etc., as illustrated the following reaction scheme (I):

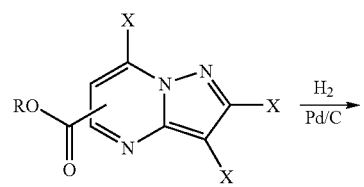

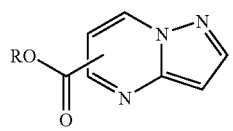

The halogen substituent may be replaced by an aryl using a Pd complex and an aryl boric acid compound according to the so-called Suzuki reaction, as illustrated in the following reaction scheme (II):

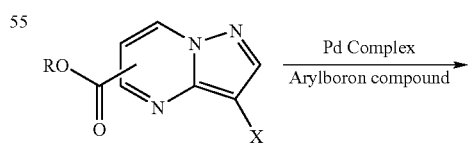

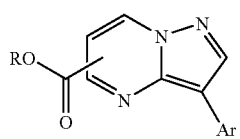

Also, for example, the introduction of an alkynyl group such as the compound No. A-253 may be made using a Pd complex and an acetylene compound, according to the so-called Sonogashira reaction.

Also, a process for substituting the halogen on an aromatic ring is well known in the art. For example, the hydrogen atom on an aromatic ring may readily be halogenated using bromide or iodine monochloride.

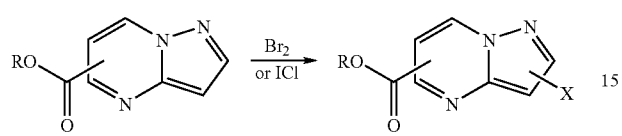

The ketone on the ring structure may be halogenated, according to techniques well known to those skilled in the art.

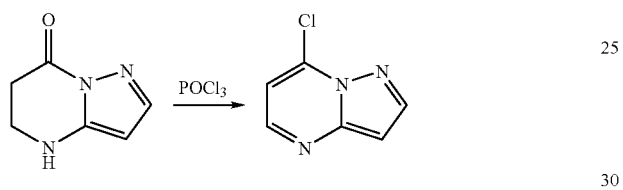

A process for synthesizing the pyrazolo-[1,5-a]-pyrimidine ring structure on the compound (I) of the present invention is known in the art. For example, see Novinson, T.; Robins, R. K.; Matthews, T. R., J. Med. Chem. 1977, 20(2), 298-299, and Ann. Chim. (Rome), 1970, 60, 225, Ann. Chim. (Rome), 1970, 60, 227.

The pyrazolo-[1,5-a]-pyrimidine ring structure may also synthesized by the reaction of the pyrazol ring with ethylene methylene malonate, and the further halogenation of the resulting ketone, as illustrated in the following reaction scheme (IV):

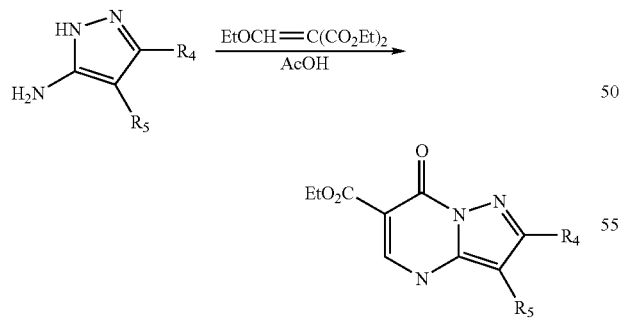

As mentioned above, the details of the present invention are described in various embodiments, but it is to be understood that specific embodiments and examples in the specification are illustrative only, and the scope of the present invention is not limited to these illustrative specific embodiments and examples in any way.

EXAMPLES

Example 1

Synthesis of 7-chloro-pyrazolo-[1,5-a]-pyrimidine-5-carboxylic acid ethyl ester

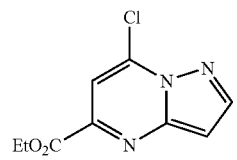

The above ester was synthesized according to Novinson, T.; Robins, R. K.; Matthews, T. R., J. Med. Chem. 1977, 20(2), 298-299.

Example 2

Synthesis of pyrazolo-[1,5-a]-pyrimidine-5-carboxylic acid ethyl ester)

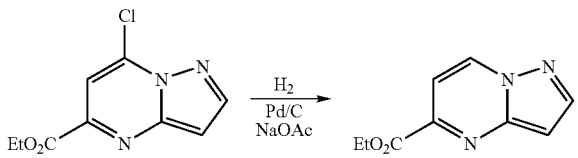

A suspension of 7-chloro-pyrazolo-[1,5-a]-pyrimidine-5-carboxylic acid ethyl ester (15.0 g), sodium acetate (6.54 g), and 10% palladium on carbon (665 mg) in ethyl acetate-ethanol (1-1.50 mL) was stirred under a hydrogen atmosphere. After the completion of the reaction, the reactant was filtered, and concentrated in vacuo. The residue was dissolved in ethyl acetate, washed with water, aqueous baking soda, and brine, dried with sodium sulfate, and concentrated in vacuo. The yellow residue was recrystallized to yield a light yellow needle crystal (9.9 g, 78%). mp:114-115° C.

Example 3

Synthesis of 3-bromo-pyrazolo-[1,5-a]-pyrimidine-5-carboxylic acid ethyl ester and 3-iodo-pyrazolo-[1,5-a]-pyrimidine-5-carboxylic acid ethyl ester

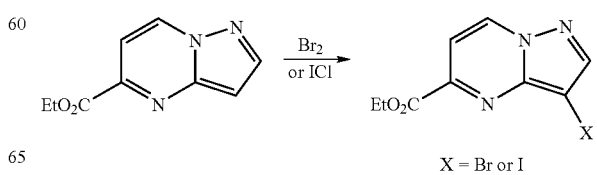

X = Br or I

To a solution of pyrazolo-[1,5-a]-pyrimidine-5-carboxylic acid ethyl ester (6.00 g) in chloroform (60 mL), a solution of bromine (1.61 mL) in chloroform (3 mL) was added dropwise under a ice-cooled condition. It was stirred at the same temperature over 15 minutes, followed by the addition of water (100 mL), and neutralization with baking soda. The reaction mixture was extracted with chloroform, and the extracted layer was washed with brine, and thereafter dried with magnesium sulfate, and concentrated in vacuo. The residue was recrystallized from ethyl acetate to yield a yellow columnar crystal (8.03 g, 95%). Mp:113-114° C.

To a solution of pyrazolo-[1,5-a]-pyrimidine-5-carboxylic acid ethyl ester (1.53 g) and iodine pentoxide (23 mg) in chloroform (60 mL), iodine monochloride (0.70 mL) was added dropwise at 40° C. The resulting reaction suspension was stirred at the same temperature over 30 minutes, and thereafter diluted with chloroform, and neutralized with baking soda. It was extracted from chloroform, and the extracted layer was washed with brine, and thereafter dried with sodium sulfate, and concentrated in vacuo. The residue was recrystallized from ethyl acetate-hexane to yield a yellow needle crystal (2.13 g, 98%). mp: 145-146° C.

Example 4

Synthesis of 3-bromo-pyrazolo-[1,5-a]-pyrimidine-5-carboxylic acid and 3-iodo-pyrazolo-[1,5-a]-pyrimidine-5-carboxylic acid

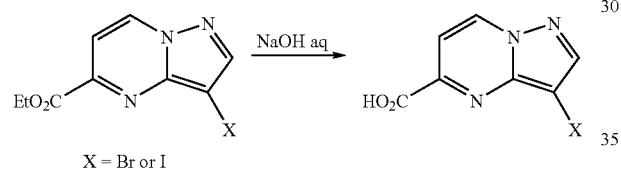

X = Br or I

To a solution of 3-bromo-pyrazolo-[1,5-a]-pyrimidine-5-carboxylic acid ethyl ester (3.00 g) in methanol (200 mL), a 2N aqueous sodium hydroxide solution (11 mL) was added, and the resulting suspension was stirred at room temperature over 30 minutes, and thereafter neutralized with a 1N hydrochloric acid (22 mL) under a ice-cooled condition. A precipitate that was obtained by the reduced-pressure distillation of methanol was filtered, washed with water, and dried to yield a yellow solid (2.60 g, 97%). Mp: about 200° C. (sublimated).

In the same manner, a yellow solid (1.82 g, 95%) was yielded from 3-iodo-pyrazolo-[1,5-a]-pyrimidine-5-carboxylic acid ethyl ester (2.10 g). Mp: about 215° C. (sublimated at about 200° C.)

Example 5

Synthesis of 3-(3-chlorophenyl)-pyrazolo-[1,5-a]-pyrimidine-5-carboxylic acid ethyl ester

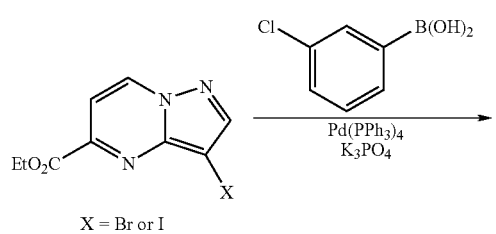

X = Br or I

-continued

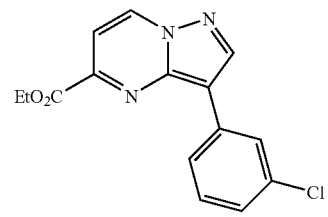

A mixture of 3-bromo-pyrazolo-[1,5-a]-pyrimidine-5-carboxylic acid ethyl ester (18.00 g), 3-chlorophenyl boric acid (12.50 g), calcium phosphate (31.12 g), and 200 ml of dioxane was stirred under a nitrogen atmosphere, added with tetrakis(triphenylphosphine) palladium (0) (1.50 g), and heated at reflux over 3 hours. The reactant was cooled to room temperature, and thereafter poured into 150 ml of water, and extracted with 300 ml of toluene. The extract was washed with saturated saline solution, dried with magnesium sulfate, and concentrated in vacuo. The resulting residue was purified by silica gel column chromatography (ethyl acetate:toluene=8:2) to yield 3-(3-chlorophenyl)-pyrazolo-[1,5-a]-pyrimidine-5-carboxylic acid ethyl ester (18.05 g, 89%) as a brown columnar crystal. mp: 126-129° C.

Example 6

Synthesis of 3-(3-chlorophenyl)-pyrazolo-[1,5-a]-pyrimidine-5-carboxylic acid

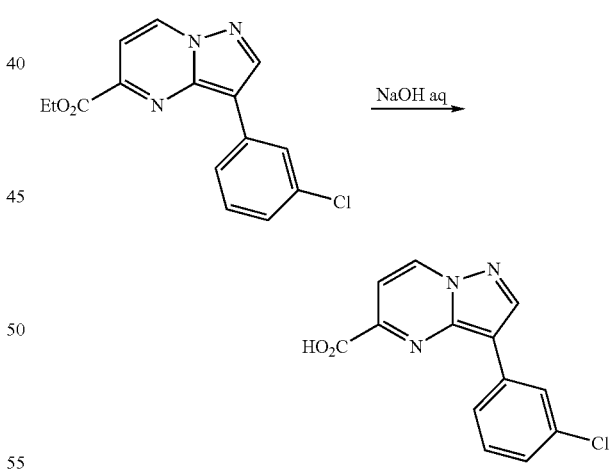

To a mixture of 3-(3-chlorophenyl)-pyrazolo-[1,5-a]-pyrimidine-5-carboxylic acid ethyl ester (18.00 g), 120 ml of methanol, and 120 ml of tetrahydrofuran, 60 ml of a 2N aqueous sodium hydroxide solution was added, and stirred at room temperature over 2 hours. To the reactant, 60 ml of 2N hydrochloride was added dropwise, and the precipitated crystal was filtered to yield 3-(3-chlorophenyl)-pyrazolo-[1,5-a]-pyrimidine-5-carboxylic acid (14.02 g, 86%) as a yellow crystal.

Example 7

Synthesis of N-2-cyclohexylphenyl-3-(3-chlorophenyl)-pyrazolo-[1,5-a]-pyrimidine-5-amide

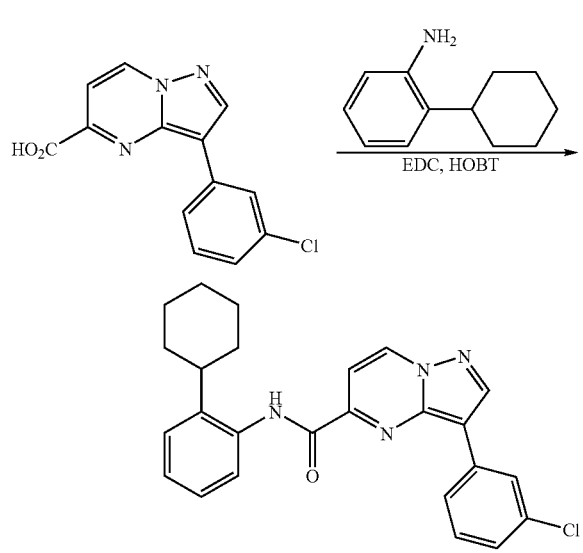

To a mixture of 3-(3-chlorophenyl)-pyrazolo-[1,5-a]-pyrimidine-5-carboxylic acid (0.08 g), 2-cyclohexylaniline (0.06 g), and 2 ml of N,N-dimethylformamide, 1-hyhdroxy benzotriazol (0.05 g) and 1-ethyl-3-(3-dimethylaminopropyl)carbodiimide hydrochloride (0.07 g) were added, and stirred at room temperature over 2 hours. The reactant was poured into 20 ml of water, and extracted with 80 ml of ethyl acetate. The extract was washed saturated saline solution, dried with magnesium sulfate, and concentrated in vacuo. The resulting residue was purified by silica gel column chromatography (ethyl acetate:toluene=1:1), and recrystallized with ethyl acetate to yield N-2-cyclohexylphenyl-3-(3-chlorophenyl)-pyrazolo-[1,5-a]-pyrimidine-5-amide (0.08 g, 64%) as a yellow needle crystal. mp: 160.2-161.4° C.

Example 8

Synthesis of 7-oxo-2-phenyl-4,7-dihydro-pyrazolo-[1,5-a]-pyrimidine-5-carboxylic acid ethyl ester

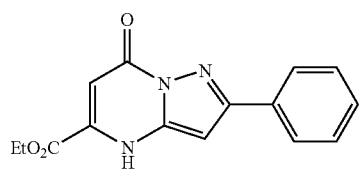

This compound was synthesized according to Ann. Chim. (Rome), 1970, 60, 225, Ann. Chim. (Rome), 1970, 60, 227. mp: 256-257° C.

Example 9

Synthesis of 2-phenyl-7-chloro-pyrazolo-[1,5-a]-pyrimidine-5-carboxylic acid ethyl ester

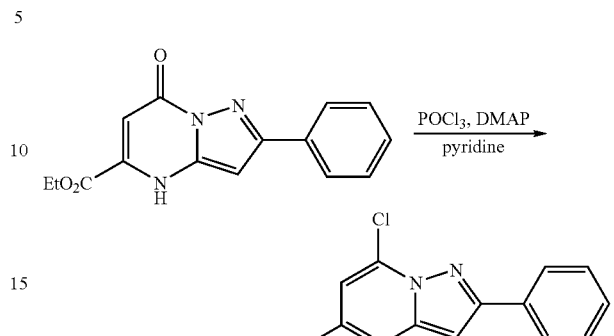

This compound was synthesized from 7-oxo-2-phenyl-4,7-dihydro-pyrazolo-[1,5-a]-pyrimidine-5-carboxylic acid ethyl ester, according to the process for synthesizing 7-chloropyrazolo-[1,5-a]-pyrimidine-5-carboxylic acid ethyl ester. mp: 135-137° C.

Example 10

Synthesis of 2-phenyl-pyrazolo-[1,5-a]-pyrimidine-5-carboxylic acid ethyl ester

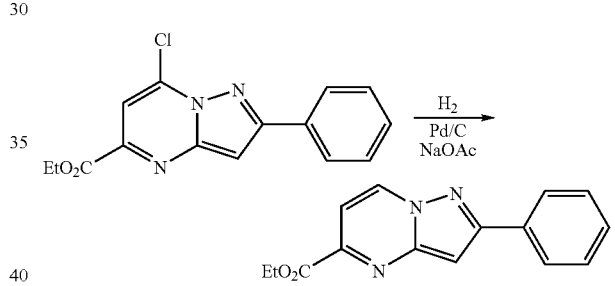

This compound was synthesized from 2-phenyl-7-chloro-pyrazolo-[1,5-a]-pyrimidine-5-carboxylic acid ethyl ester, according to the process for synthesizing the foregoing pyrazolo-[1,5-a]-pyrimidine-5-carboxylic acid ethyl ester. mp: 180-181° C.

Example 11

Synthesis of 2-phenyl-pyrazolo-[1,5-a]-pyrimidine-5-carboxylic acid

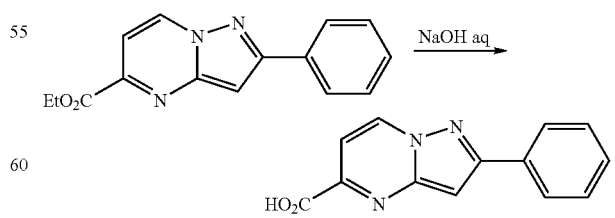

This compound was synthesized from 2-phenyl-7-chloro-pyrazolo-[1,5-a]-pyrimidine-5-carboxylic acid ethyl ester, according to the process for synthesizing the foregoing 3-(3-chlorophenyl)-pyrazolo-[1,5-a]-pyrimidine-5-carboxylic acid ethyl ester.

Example 12

Synthesis of N-(2-morpholinophenyl)methyl 2-phenyl-pyrazolo-[1,5-a]-pyrimidine-5-amide

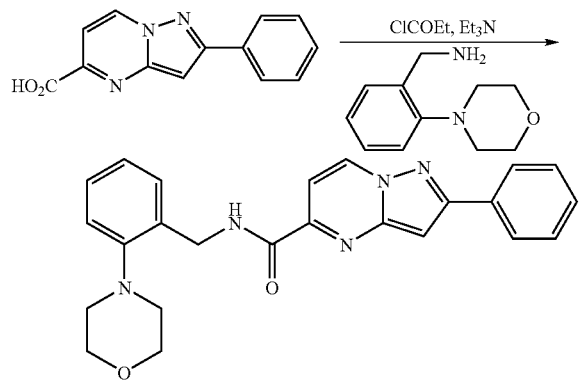

To a solution of 2-phenyl- pyrazolo-[1,5-a]-pyrimidine-5-carboxylic acid (120 mg), and triethylamine (0.091 ml) in tetrahydrofuran (10 ml), ethyl chlorocarbonate (0.053 ml) was added at −40° C. It was further added with a solution of 2-morpholinobenzylamine (115 mg) in tetrahydrofuran (2 ml), and thereafter heated to −20° C. The reaction solution was distilled under a reduced pressure, and then water was added thereto, extracted with chloroform, and the organic layer was dried with magnesium sulfate. After the reduced-pressure distillation of the solvent, the residue was purified by a silica gel column chromatography, and thereafter recrystallized from acetone-diisopropyl ether to yield N-(2-morpholinophenyl)methyl 2-phenyl-pyrazolo-[1,5-a]-pyrimidine-5-amide (142 mg, 69%). mp: 190-192° C.

Example 13

2-amino-4-(3-chlorophenyl)pyrazole

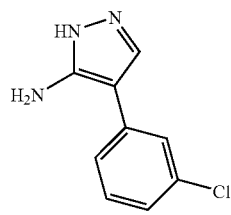

This compound was synthesized according to J. Heterocyclic. Chem., 1995, 32, 291.

Example 14

Synthesis of 7-oxo-3-(3-chlorophenyl)-4,7-dihydro-pyrazolo-[1,5-a]-pyrimidine-6-carboxylic acid ethyl ester

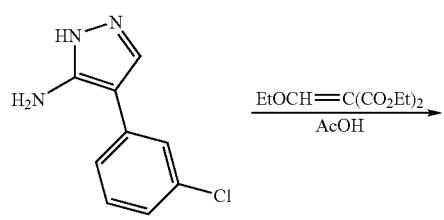

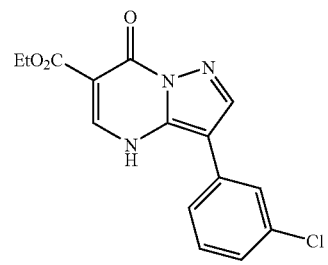

To 2-amino-4-(3-chlorophenyl)pyrazole (5.73 g) in acetic acid (57 ml), diethylethoxymethylene malonate (6.58 ml) was added, and heated at reflux over 5 hours. The acetic acid was distilled under a reduced pressure, and thereafter ethyl acetate (30 ml) was added, and the mixture was heated at reflux over 15 minutes. The reactant was cooled, and thereafter the precipitate was filtered to yield 7-oxo-3-(3-chlorophenyl)-4,7-dihydro-pyrazolo-[1,5-a]-pyrimidine-6-carboxylic acid ethyl ester (7.15 g, 76%).

Example 15

Synthesis of 3-(3-chlorophenyl)-7-chloro-pyrazolo-[1,5-a]-pyrimidine-6-carboxylic acid ethyl ester

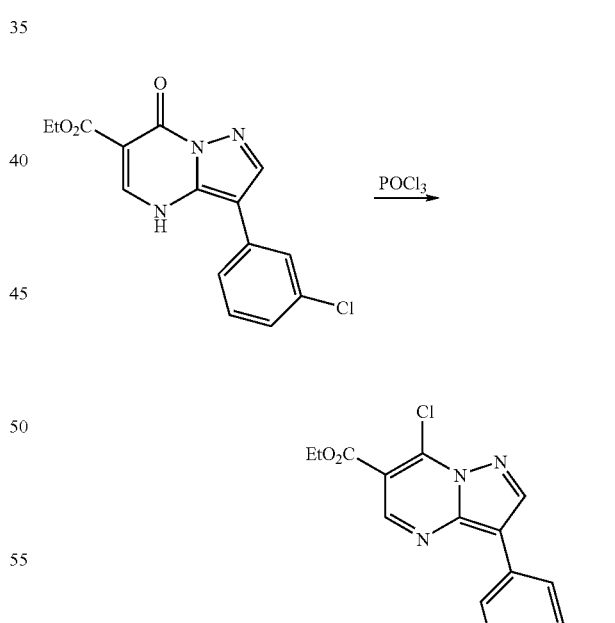

This compound was synthesized from 7-oxo-3-(3-chlorophenyl)-4,7-dihydro-pyrazolo-[1,5-a]-pyrimidine-6-carboxylic acid ethyl ester, according to the process for synthesizing the foregoing 7-chloro-pyrazolo-[1,5-a]-pyrimidine-5-carboxylic acid ethyl ester. mp: 140-141° C.

Example 16

Synthesis of 3-(3-chlorophenyl)-pyrazolo-[1,5-a]-pyrimidine-6-carboxylic acid ethyl ester

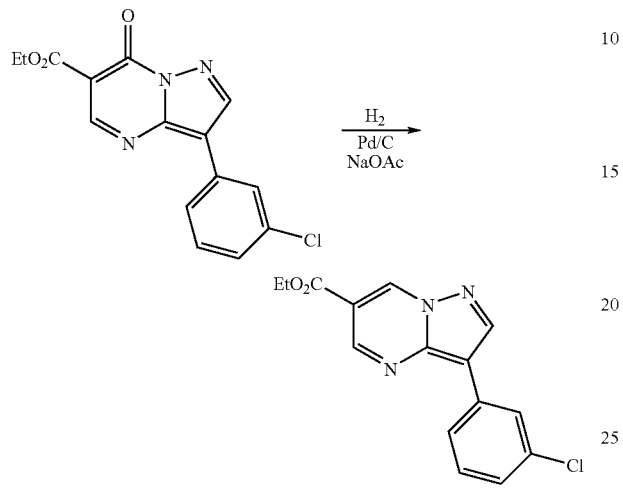

This compound was synthesized from 3-(3-chlorophenyl)-7-chloro-pyrazolo-[1,5-a]-pyrimidine-6-carboxylic acid ethyl ester, according to the process for synthesizing the foregoing pyrazolo-[1,5-a]-pyrimidine-5-carboxylic acid ethyl ester. mp: 135.5° C.

Example 17

Synthesis of 3-(3-chlorophenyl)-pyrazolo-[1,5-a]-pyrimidine-6-carboxylic acid

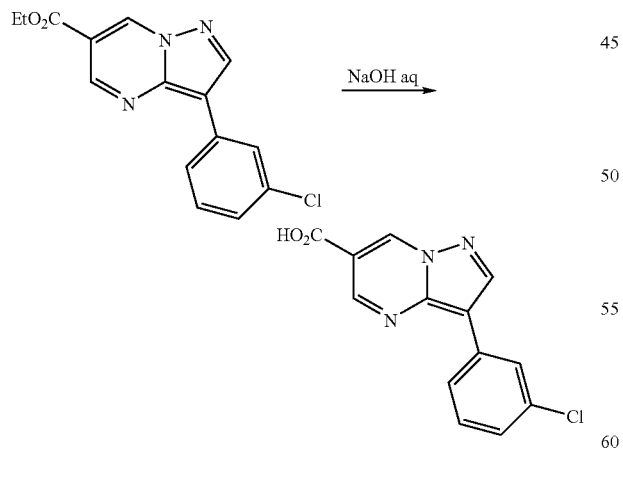

This compound was synthesized from 3-(3-chlorophenyl)-pyrazolo-[1,5-a]-pyrimidine-6-carboxylic acid ethyl ester, according to the process for synthesizing the foregoing 3-(3-chlorophenyl)-pyrazolo-[1,5-a]-pyrimidine-5-carboxylic acid. mp: 272-275° C. (decomposed).

Example 18

Synthesis of N-{2-(4-t-butoxycarbonyl piperazino)phenyl}methyl 3-(3-chlorophenyl)-pyrazolo-[1,5-a]-pyrimidine-6-amide

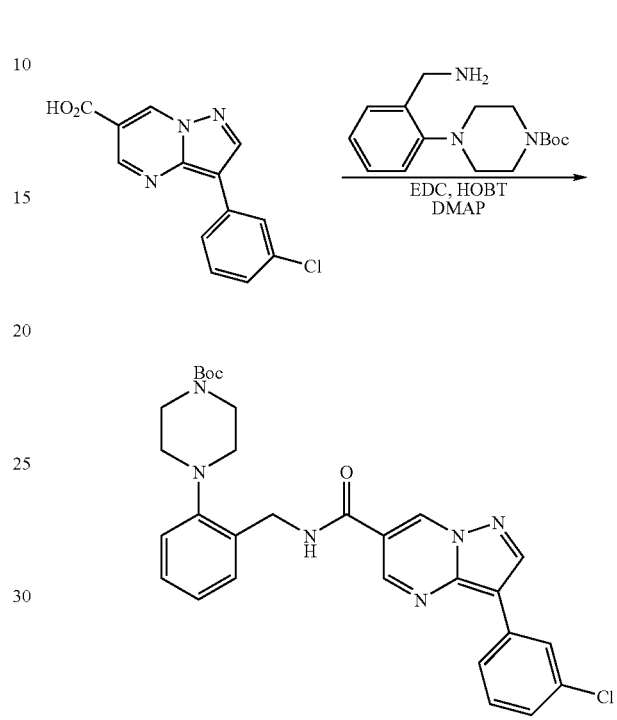

This compound was synthesized from 3-(3-chlorophenyl)-pyrazolo-[1,5-a]-pyrimidine-6-carboxylic acid, according to the process for synthesizing the foregoing N-2-cyclohexylphenyl-3-(3-chlorophenyl)-pyrazolo-[1,5-a]-pyrimidine-5-amide. mp: 201-202° C. (decomposed).

Example 19

Synthesis of N-(2- piperazinophenyl) methyl 3-(3-chlorophenyl)-pyrazolo-[1,5-a]-pyrimidine-6-amide

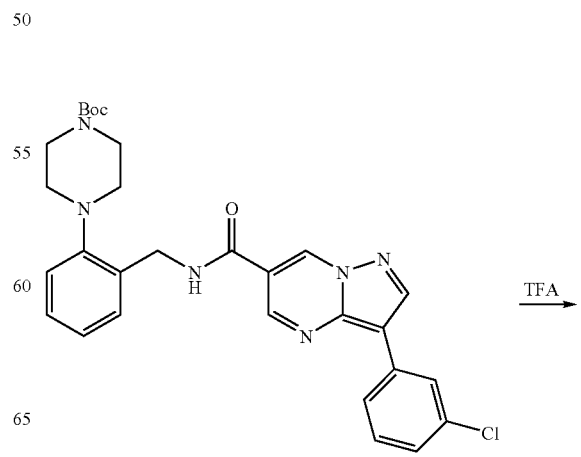

-continued

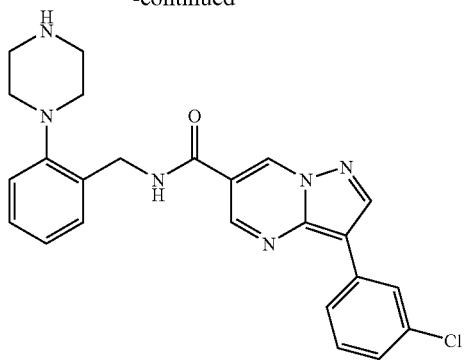

A solution of N-{2-(4-t-butoxycarbonyl piperazino)phenyl}methyl 3-(3-chlorophenyl)-pyrazolo-[1,5-a]-pyrimidine-6-amide (300 mg) and trifluoroacetic acid (0.42 ml) in chloroform (6 ml) was heated at reflux over 6 hours. The reactant was cooled, and ice and a 2N aqueous sodium hydroxide solution (3 ml) were added, and thereafter extracted with chloroform. The organic layer was dried with magnesium sulfate, and thereafter the solvent was distilled under a reduced pressure. The residue was purified by an alumina column chromatography, and thereafter recrystallized from tetrahydrofuran-diisopropyl ether to yield N-(2-piperazinophenyl)methyl 3-(3-chlorophenyl)-pyrazolo-[1,5-a]-pyrimidine-6-amide (220 mg, 90%). mp: 185-188° C.

These synthesis processes are applicable in the same manner to compounds which are similar to those specifically illustrated herein.

Example 20

Various Synthesis Examples

The compounds of the present invention were further synthesized according to the procedures described in the above examples. The melting points and $^1$H-NMR was determined for some of the synthesized compounds. NMR was carried out using the following conditions.

The $^1$H-NMR values were measured in a deuterated dimethylsulfoxide (DMSO-$d_6$), deuterated chloroform (CDCl$_3$), or deuterated pyridine (pyridin-$d_5$) solvent using tetramethylsilane as an internal standard. The δ values and binding constants (J) are described in ppm and Hz, respectively. s, d, t, q, quint, sext, m, and br refer to singlet, doublet, triplet, quartet, quintet, sextet, multiplet, and broad, respectively.

The structures of the compounds synthesized herein are listed in the following tables 1 and 2. They provide the results of the melting points (m.p.(° C.)) and NMR values (if measured) for each compound.

TABLE 1

| Chemical Formula | Compound No. | NMR | m. p. (° C.) |
|---|---|---|---|
|  | A-1 | — | — |
|  | A-2 | — | — |
|  | A-3 | — | — |

TABLE 1-continued

| Chemical Formula | Compound No. | NMR | m.p. (° C.) |
|---|---|---|---|
| [pyrazolo[1,5-a]pyrimidine with N-methylcarboxamide and 3-phenyl] | A-4 | — | — |
| [pyrazolo[1,5-a]pyrimidine with N-sec-butylcarboxamide and 3-(2-fluorophenyl)] | A-5 | — | — |
| [pyrazolo[1,5-a]pyrimidine with N-methyl-N-sec-butylcarboxamide and 3-(2-fluorophenyl)] | A-6 | — | — |
| [pyrazolo[1,5-a]pyrimidine with N-sec-butylcarboxamide and 3-(2-chlorophenyl)] | A-7 | — | — |
| [pyrazolo[1,5-a]pyrimidine with N-methyl-N-sec-butylcarboxamide and 3-(2-chlorophenyl)] | A-8 | — | — |
| [pyrazolo[1,5-a]pyrimidine with N-sec-butylcarboxamide and 3-(3-trifluoromethylphenyl)] | A-9 | — | — |

TABLE 1-continued

| Chemical Formula | Compound No. | NMR | m. p. (° C.) |
|---|---|---|---|
| (structure) | A-10 | — | — |
| (structure) | A-11 | — | — |
| (structure) | A-12 | — | — |
| (structure) | A-13 | — | — |
| (structure) | A-14 | — | — |
| (structure) | A-15 | — | — |

TABLE 1-continued

| Chemical Formula | Compound No. | NMR | m. p. (° C.) |
|---|---|---|---|
| (structure) | A-16 | — | — |
| (structure) | A-17 | — | — |
| (structure) | A-18 | — | — |
| (structure) | A-19 | — | — |
| (structure) | A-20 | — | — |
| (structure) | A-21 | — | — |
| (structure) | A-22 | — | — |

TABLE 1-continued
| Chemical Formula | Compound No. | NMR | m. p. (° C.) |
|---|---|---|---|
| 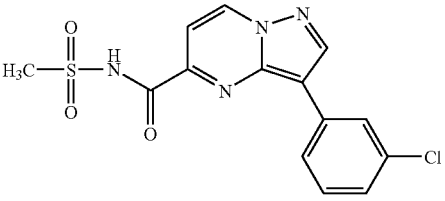 | A-23 | — | — |
| 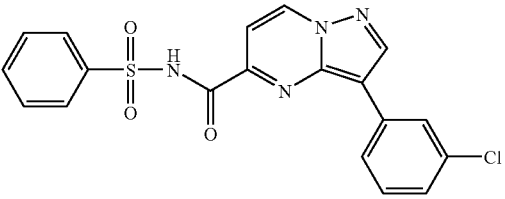 | A-24 | — | — |
| 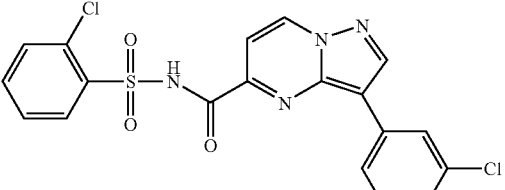 | A-25 | — | — |
| 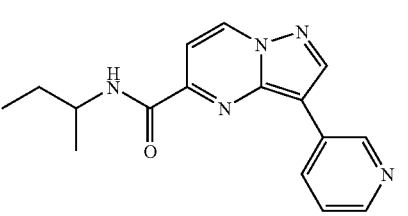 | A-26 | — | — |
| 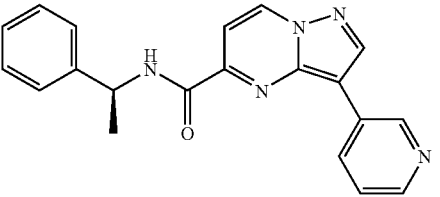 | A-27 | — | — |
| 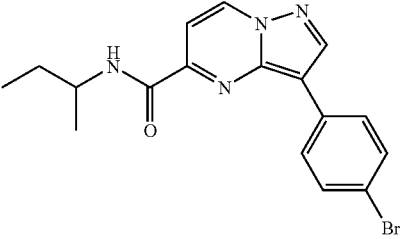 | A-28 | — | — |

TABLE 1-continued

| Chemical Formula | Compound No. | NMR | m. p. (° C.) |
|---|---|---|---|
| | A-29 | — | — |
| | A-30 | — | — |
| | A-31 | — | — |
| | A-32 | — | — |
| | A-33 | — | — |
| | A-34 | — | — |

TABLE 1-continued

| Chemical Formula | Compound No. | NMR | m. p. (° C.) |
|---|---|---|---|
| [sec-butyl-NH-C(O)-pyrazolo[1,5-a]pyrimidine-3-Cl] | A-35 | — | — |
| [sec-butyl-NH-C(O)-pyrazolo[1,5-a]pyrimidine-3-Br] | A-36 | — | — |
| [sec-butyl-NH-C(O)-pyrazolo[1,5-a]pyrimidine-3-I] | A-37 | — | — |
| [sec-butyl-NH-C(O)-pyrazolo[1,5-a]pyrimidine-3-CHO] | A-38 | — | — |
| [sec-butyl-NH-C(O)-pyrazolo[1,5-a]pyrimidine-3-NMe2] | A-39 | — | — |
| [sec-butyl-NH-C(O)-pyrazolo[1,5-a]pyrimidine-3-pyrrolidinyl] | A-40 | — | — |
| [sec-butyl-NH-C(O)-pyrazolo[1,5-a]pyrimidine-3-morpholinyl] | A-41 | — | — |
| [sec-butyl-NH-C(O)-pyrazolo[1,5-a]pyrimidine-3-(4-methylpiperazinyl)] | A-42 | — | — |
| [sec-butyl-NH-C(O)-pyrazolo[1,5-a]pyrimidine-3-(4-phenylpiperazinyl)] | A-43 | — | — |

TABLE 1-continued

| Chemical Formula | Compound No. | NMR | m. p. (° C.) |
|---|---|---|---|
| [structure with sec-butylamide, pyrazolopyrimidine, COPh] | A-44 | — | — |
| [structure with sec-butylamide, pyrazolopyrimidine, CH(OH)Ph] | A-45 | — | — |
| [structure with sec-butylamide, pyrazolopyrimidine, CH2OH] | A-46 | — | — |
| [structure with sec-butylamide, pyrazolopyrimidine, CH=NOH] | A-47 | — | — |
| [structure with N-methylpiperazinyl-phenyl amide, pyrazolopyrimidine, 3-chlorophenyl] | A-48 | 1H-NMR(CDCl3) δ : 1.86(3H, s), 2.34(4H, br), 2.91(4H, t, J=4.8 Hz), 7.16–7.33(4H, m), 7.44(1H, t, J=7.8 Hz), 7.89(2H, d, J=7.2 Hz), 7.96(1H, m), 8.44(1H, d, J=7.5 Hz), 8.50(1H, s), 8.89(1H, d, J=7.2 Hz), 10.54(1H, br, s). | 165–166 |
| [structure with Boc-piperazinyl-phenyl amide, pyrazolopyrimidine, 3-chlorophenyl] | A-49 | — | 203–205 |
| [structure with piperazinyl-phenyl amide, pyrazolopyrimidine, 3-chlorophenyl] | A-50 | 1H-NMR(CDCl3) δ : 2.80–2.90(8H, m), 7.13–7.28(3H, m), 7.34(1H, ddd, J=8.1, 2.1, 1,2 Hz), 7.42–7.49(1H, m), 7.90–7.96(2H, m), 8.48(1H, s), 8.47–8.52(1H, m), 8.89(1H, d, J=7.2 Hz), 10.52–10.59(1H, br). | 194–196 |

TABLE 1-continued

| Chemical Formula | Compound No. | NMR | m. p. (° C.) |
|---|---|---|---|
| | A-51 | — | 147–149 |
| | A-52 | — | — |
| | A-53 | 1H-NMR(CDCl3) δ : 0.99(3H, t, J=7.2 Hz), 1.30(3H, d, J=6.3 Hz), 1.66(2H, m), 4.12(1H, m), 5.36(2H, s), 7.33–7.47(5H, m), 7.63(1H, d, J=8.1 Hz), 7.84(1H, d, J=7.2 Hz), 7.92(1H, s), 8.82(1H, d, J=6.9 Hz), 8.98(1H, s). | — |
| | A-54 | 1H-NMR(CDCl3) δ : 1.03(3H, t, J=7.2 Hz), 1.34(3H, d, J=6.6 Hz), 1.69(2H, m), 4.15(1H, m), 7.26–7.71(6H, m), 7.73(1H, d, J=6.9 Hz), 8.41(1H, s), 8.74(1H, d, J=6.9 Hz). | — |
| | A-55 | — | 104–107 |
| | A-56 | — | — |

TABLE 1-continued
| Chemical Formula | Compound No. | NMR | m. p. (° C.) |
|---|---|---|---|
| 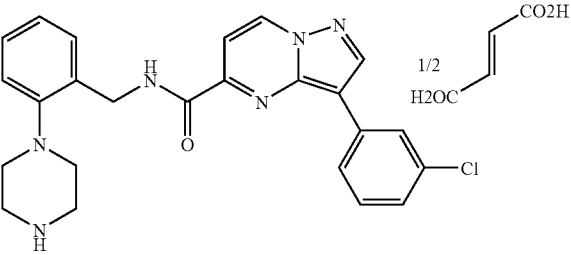 | A-57 | — | 210–211 |
| 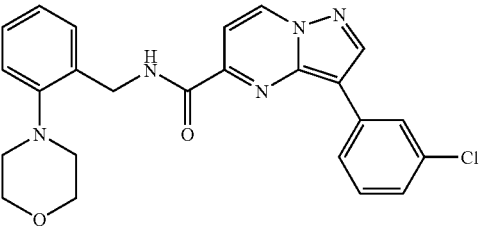 | A-58 | — | 169–171 |
| 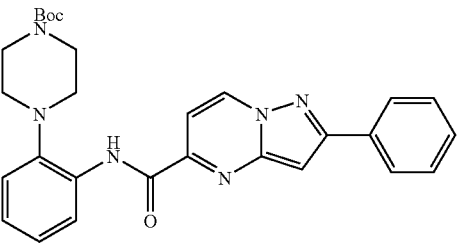 | A-59 | — | — |
| 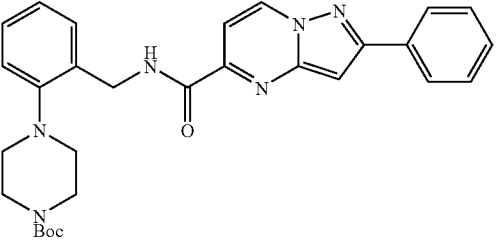 | A-60 | — | — |
| 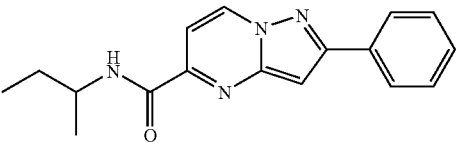 | A-61 | 1H-NMR(CDCl3) δ : 1.00(3H, t, J=7.2 Hz), 1.30(3H, d, J=6.6 Hz), 1.65(2H, m), 4.07–4.17(1H, m), 7.05(1H, d, J=0.6 Hz), 7.41–7.53(3H, m), 7.66(1H, br, s), 7.70(1H, d, J=7.2 Hz), 8.79(1H, dd, J=7.2, 0.9 Hz). | — |
| 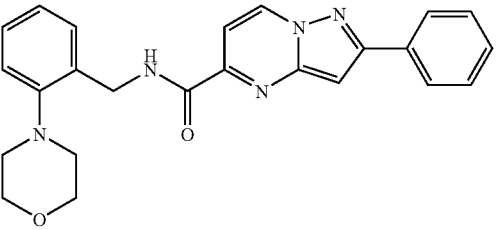 | A-62 | 1H-NMR(CDCl3) δ : 3.02(4H, t, J=4.5 Hz), 4.01(4H, t, J=4.5 Hz), 4.79(2H, d, J=6.0 Hz), 6.99(1H, d, J=0.9 Hz), 7.12–7.52(7H, m), 7.72(1H, d, J=6.9 Hz), 7.98–8.01(2H, m), 8.79(1H, dd, J=7.2, 0.6 Hz), 9.01(1H, br.t). | — |

TABLE 1-continued

| Chemical Formula | Compound No. | NMR | m. p. (° C.) |
|---|---|---|---|
| (structure) | A-63 | 1H-NMR(CDCl3) δ : 2.84(4H, br, m), 3.07(4H, t, J=4.5 Hz), 7.13–7.23(2H, m), 7.29–7.32(1H, m), 7.49–7.57(4H, m), 7.69(1H, d, J=6.9 Hz), 8.13–8.16(2H, m), 8.44(1H, dd, J=7.2, 2.1 Hz), 9.38(1H, d, J=7.2 Hz), 10.95(1H, s). | — |
| (structure) | A-64 | 1H-NMR(CDCl3) δ : 3.00(4H, t, J=4.8 Hz), 3.19(4H, t, J=4.8 Hz), 4.78(2H, d, J=4.7 Hz), 6.99(1H, d, J=0.9 Hz), 7.13(1H, td, J=7.2, 1.5 Hz), 7.21–7.52(6H, m), 7.72(1H, d, J=7.2 Hz), 7.97–8.01(2H, m), 8.79(1H, dd, J=7.2, 0.9 Hz), 9.07(1H, br, t). | — |
| (structure) | A-65 | — | — |
| (structure) | A-66 | — | — |
| (structure) | A-67 | 1H-NMR(CDCl3) δ : 1.84(1H, m), 2.43(2H, m), 2.76(2H, m), 2.98(1H, m), 3.70(2H, s), 4.67(1H, m), 7.24–7.37(6H, m), 7.43(1H, t, J=7.5 Hz), 7.75(1H, d, J=7.2 Hz), 7.88(1H, br. d, J=7.8 Hz), 8.10(1H, br. s), 8.17(1H, br), 8.51(1H, s), 8.81(1H, d, J=7.2 Hz). | — |
| (structure) | A-68 | — | — |

TABLE 1-continued

| Chemical Formula | Compound No. | NMR | m. p. (° C.) |
|---|---|---|---|
| (structure) | A-69 | — | — |
| (structure) | A-70 | 1H-NMR(CDCl3) δ : 2.91(8H, m), 7.13–7.28(3H, m), 7.45(1H, ddd, J=8.0, 5.0, 0.6 Hz), 7.96(1H, d, J=7.2 Hz), 8.25(1H, ddd, J=8.0, 2.4, 1.5 Hz), 8.54(1H, s), 8.55(1H, dd, J=8.0, 0.6 Hz), 8.62(1H, dd, J=5.0, 1.5 Hz), 8.91(1H, d, J=7.2 Hz), 9.34(1H, dd, J=1.5, 0.6 Hz | — |
| (structure) | A-71 | — | — |
| (structure) | A-72 | — | — |

TABLE 1-continued

| Chemical Formula | Compound No. | NMR | m. p. (° C.) |
|---|---|---|---|
| (structure) | A-73 | — | — |
| (structure) | A-74 | — | — |
| (structure) | A-75 | — | — |
| (structure) | A-76 | — | — |
| (structure) | A-77 | — | — |

TABLE 1-continued
| Chemical Formula | Compound No. | NMR | m. p. (° C.) |
|---|---|---|---|
| 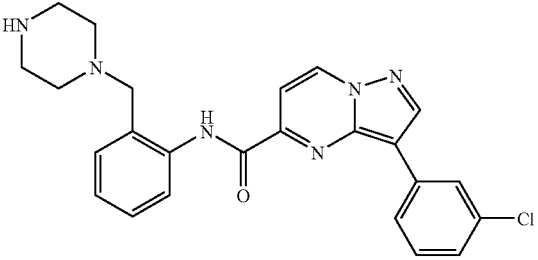 | A-78 | — | — |
| 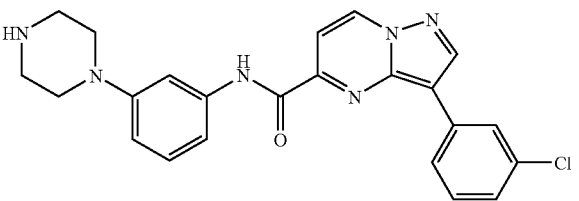 | A-79 | — | — |
| 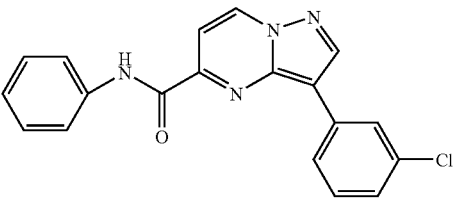 | A-80 | — | — |
| 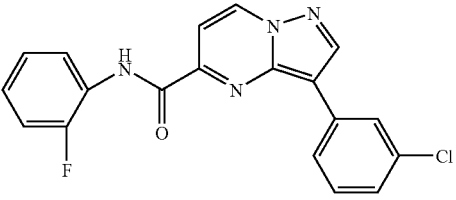 | A-81 | — | — |
| 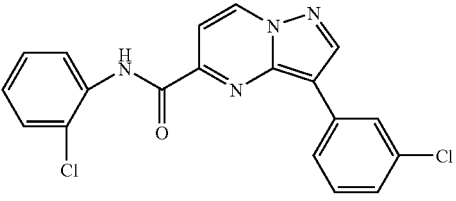 | A-82 | — | — |
| 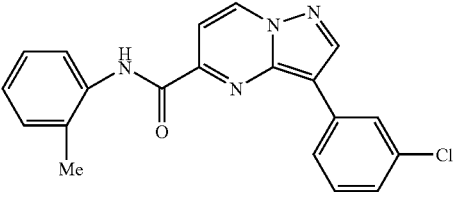 | A-83 | — | — |
| 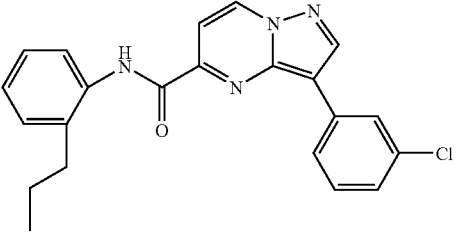 | A-84 | — | — |

TABLE 1-continued

| Chemical Formula | Compound No. | NMR | m. p. (° C.) |
|---|---|---|---|
| | A-85 | — | — |
| | A-86 | — | — |
| | A-87 | — | — |
| | A-88 | — | — |
| | A-89 | — | — |

TABLE 1-continued
| Chemical Formula | Compound No. | NMR | m. p. (° C.) |
|---|---|---|---|
| 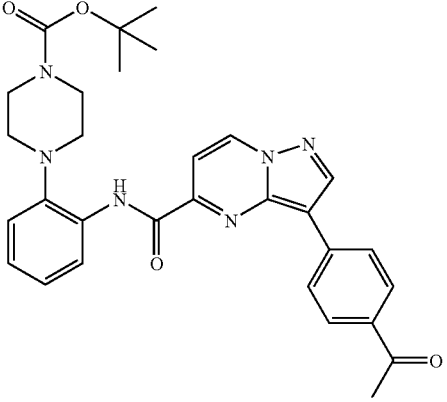 | A-90 | — | — |
| 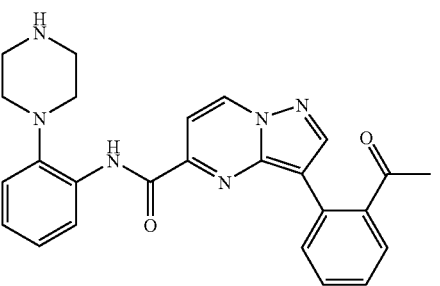 | A-91 | — | — |
| 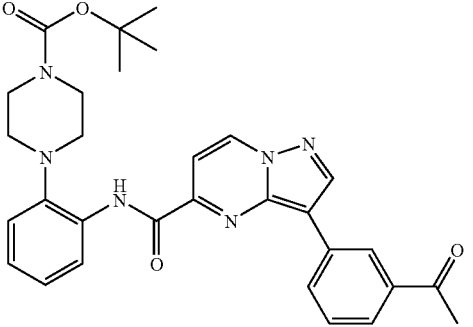 | A-92 | — | — |
| 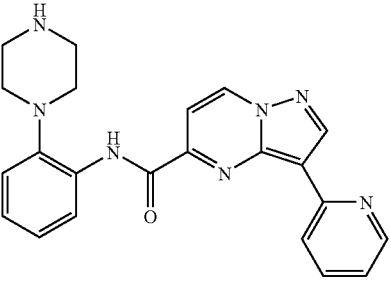 | A-93 | — | — |

TABLE 1-continued

| Chemical Formula | Compound No. | NMR | m. p. (° C.) |
|---|---|---|---|
| | A-94 | — | — |
| | A-95 | — | — |
| | A-96 | — | — |
| | A-97 | — | — |
| | A-98 | — | — |

TABLE 1-continued

| Chemical Formula | Compound No. | NMR | m. p. (° C.) |
|---|---|---|---|
| (piperidine-phenyl-NHC(O)-pyrazolo[1,5-a]pyrimidine-3-chlorophenyl) | A-99 | — | — |
| (piperazine-phenyl-NHC(O)-pyrazolo[1,5-a]pyrimidine-4-acetylphenyl) | A-100 | — | — |
| (piperazine-phenyl-NHC(O)-pyrazolo[1,5-a]pyrimidine-3-acetylphenyl) | A-101 | — | — |
| (Boc-piperazine-phenyl-NHC(O)-pyrazolo[1,5-a]pyrimidine-2-CF₃-phenyl) | A-102 | — | — |
| (piperazine-phenyl-NHC(O)-pyrazolo[1,5-a]pyrimidine-3-CF₃-phenyl) | A-103 | — | — |

TABLE 1-continued
| Chemical Formula | Compound No. | NMR | m. p. (° C.) |
|---|---|---|---|
| 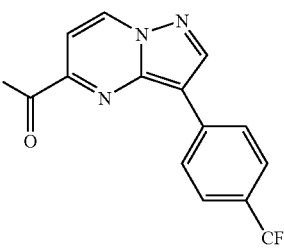 | A-104 | — | — |
| 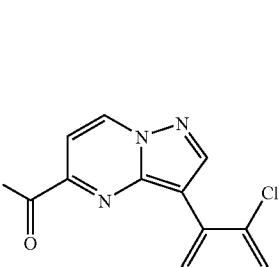 | A-105 | — | — |
| 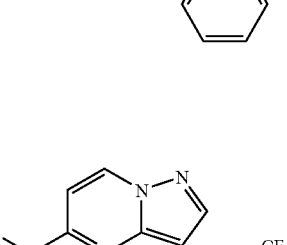 | A-106 | — | — |
| 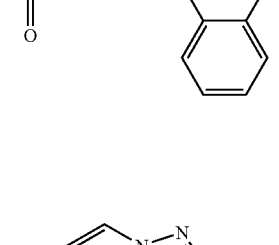 | A-107 | — | — |
| 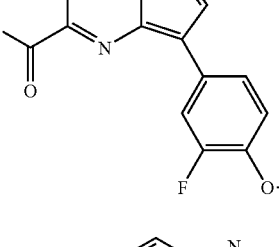 | A-108 | — | — |

TABLE 1-continued
| Chemical Formula | Compound No. | NMR | m. p. (° C.) |
|---|---|---|---|
| 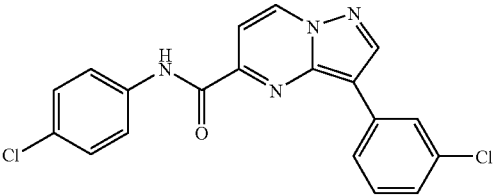 | A-109 | — | — |
| 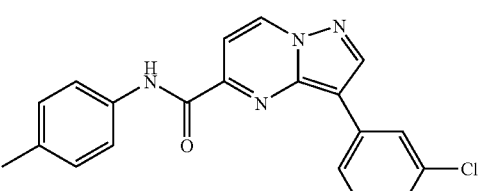 | A-110 | — | — |
| 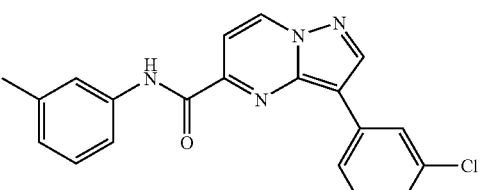 | A-111 | — | — |
| 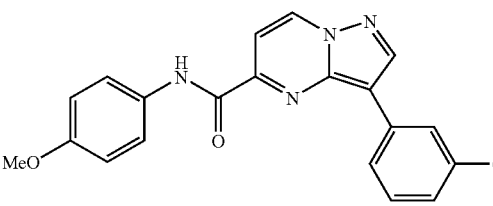 | A-112 | — | — |
| 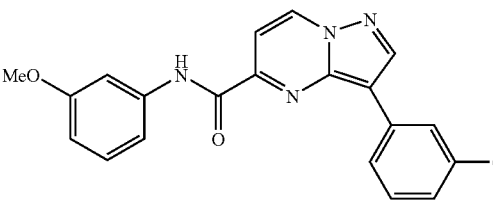 | A-113 | — | — |
| 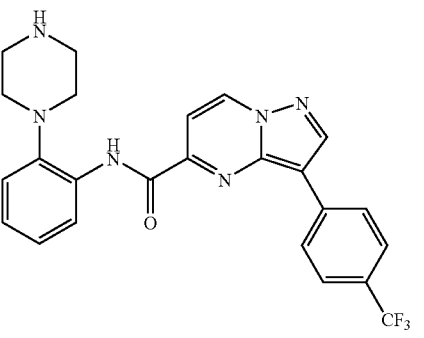 | A-114 | — | — |

TABLE 1-continued

| Chemical Formula | Compound No. | NMR | m. p. (° C.) |
|---|---|---|---|
| (structure with NHBoc pyrrolidine, phenyl, amide, pyrazolopyrimidine, 3-chlorophenyl) | A-115 | — | — |
| (structure with NHBoc pyrrolidine, phenyl, amide, pyrazolopyrimidine, 3-chlorophenyl) | A-116 | — | — |
| (structure with NH₂ pyrrolidine, phenyl, amide, pyrazolopyrimidine, 3-chlorophenyl) | A-117 | 1H-NMR(CDCl3) δ : 1.40–1.65(1H, m), 2.08–2.22(1H, m), 2.87(1H, dd, J=9.8, 4.7 Hz), 3.17–3.32(3H, m), 3.41–3.51(1H, m), 7.12–7.21(3H, m), 7.33(1H, ddd, J=8.1, 2.1, 1.2 Hz), 7.44(1H, t, J=8.0 Hz), 7.85–7.90(1H, m), 7.90(1H, d, J=7.2 Hz), 7.97(1H, t, J=2.0 Hz), 8. | — |
| (structure with NH₂ pyrrolidine, phenyl, amide, pyrazolopyrimidine, 3-chlorophenyl) | A-118 | — | — |
| (structure with piperazine, phenyl, amide, pyrazolopyrimidine, 3-fluoro-4-benzyloxyphenyl) | A-119 | — | — |

TABLE 1-continued
| Chemical Formula | Compound No. | NMR | m. p. (° C.) |
|---|---|---|---|
| 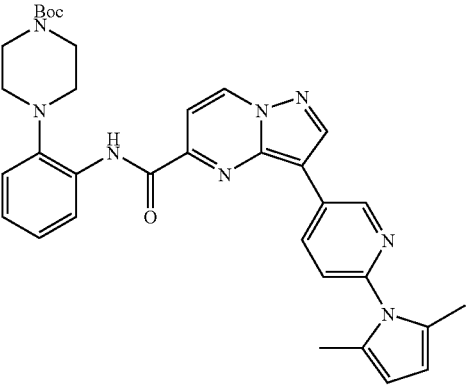 | A-120 | — | — |
| 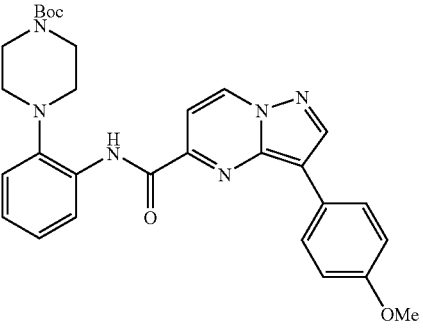 | A-121 | — | — |
| 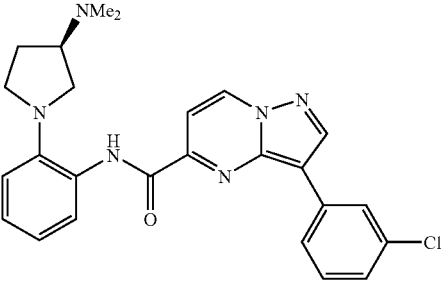 | A-123 | — | — |
| 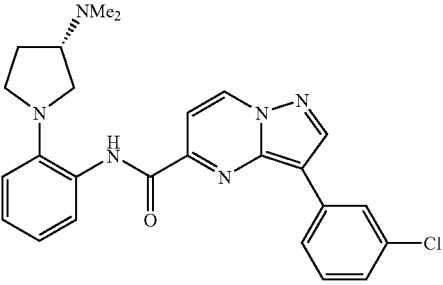 | A-124 | — | — |
| 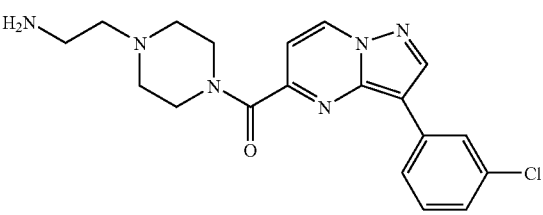 | A-125 | 1H-NMR(CDCl3) δ : 2.53(2H, t, J=6.0 Hz), 2.65(2H, t, J=5.1 Hz), 2.69(2H, t, J=5.1 Hz), 2.85(2H, t, J=6.0 Hz), 3.88(2H, t, J=5.1 Hz), 3.94(2H, t, J=5.1 Hz), 7.23–7.29(1H, m), 7.32(1H, d, J=7.2 Hz), 7.37(1H, t, J=7.8 Hz), 7.82(1H, ddd, J=7.8, 1.5, 1.2 Hz), 8.16(1H, t | — |

TABLE 1-continued

| Chemical Formula | Compound No. | NMR | m. p. (° C.) |
|---|---|---|---|
| | A-126 | — | — |
| | A-127 | — | — |
| | A-128 | — | — |
| | A-129 | — | — |
| | A-130 | — | — |

TABLE 1-continued

| Chemical Formula | Compound No. | NMR | m. p. (° C.) |
|---|---|---|---|
| | A-131 | — | — |
| | A-132 | 1H-NMR(CDCl3) δ : 7.34(1H, dd, J=7.4, 1.8 Hz), 7.40(1H, s), 7.48(1H, t, J=7.4 Hz), 7.82(1H, t, J=8.4 Hz), 7.86(1H, d, J=7.4 Hz), 8.15(1H, s), 8.35(1H, d, J=8.4 Hz), 8.40(1H, d, J=1.8 Hz), 8.56(1H, s), 8.91(1H, t, J=7.4 Hz), 9.78(1H br. s). | — |
| | A-133 | 1H-NMR(CDCl3) δ : 1.40–1.68(8H, m), 1.90–2.14(2H, m), 4.08–4.14(1H, m), 7.28(1H, dd, J=7.7, 1.8 Hz), 7.38(1H, t, J=7.7 Hz), 7.76(1H, t, J=7.7 Hz), 8.12(1H, t, J=1.8 Hz), 8.51(1H, s), 8.81(1H, d, J=7.7 Hz), 10.68(1H, br. s). | — |
| | A-134 | — | — |
| | A-135 | — | — |
| | A-136 | — | — |

TABLE 1-continued

| Chemical Formula | Compound No. | NMR | m. p. (° C.) |
|---|---|---|---|
| | A-137 | — | — |
| | A-138 | — | — |
| | A-139 | — | — |
| | A-140 | — | — |
| | A-141 | 1H-NMR(CDCl3) δ : 1.50–1.65(1H, m), 2.02–2.25(1H, m), 2.10(3H, s), 2.91–3.01(1H, m), 3.09–3.25(4H, m), 7.12–7.22(3H, m), 7.30–7.36(1H, m), 7.44(1H, t, J=7.8 Hz), 7.86–7.92(2H, m), 7.99(1H, t, J=2.0 Hz), 8.33–8.41(1H, m), 8.51(1H, s), 8.88(1H, d, J=7.2 Hz), 10 | — |
| | A-142 | 1H-NMR(CDCl3) δ : 1.51–1.65(1H, m), 2.02–2.16(1H, m), 2.10(3H, s), 2.91–3.02(1H, m), 3.09–3.25(4H, m), 7.12–7.22(3H, m), 7.30–7.36(1H, m), 7.44(1H, t, J=7.8 Hz), 7.86–7.92(2H, m), 7.99(1H, t, J=1.8 Hz), 8.33–8.41(1H, m), 8.51(1H, s), 8.88(1H, d, J=7.2 Hz), 10 | — |

TABLE 1-continued

| Chemical Formula | Compound No. | NMR | m. p. (° C.) |
|---|---|---|---|
| | A-143 | — | — |
| | A-144 | — | — |
| | A-145 | — | — |
| | A-146 | — | — |
| | A-147 | — | — |
| | A-148 | — | — |
| | A-149 | — | — |

TABLE 1-continued
| Chemical Formula | Compound No. | NMR | m. p. (° C.) |
|---|---|---|---|
| 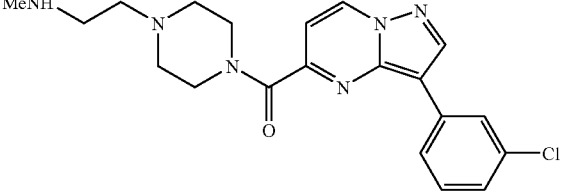 | A-150 | — | — |
| 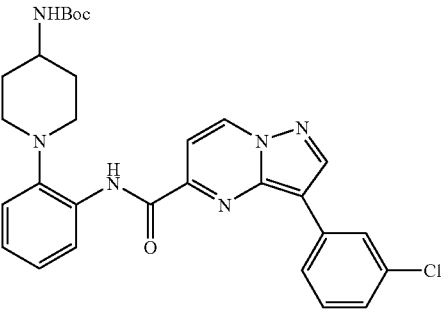 | A-151 | — | — |
| 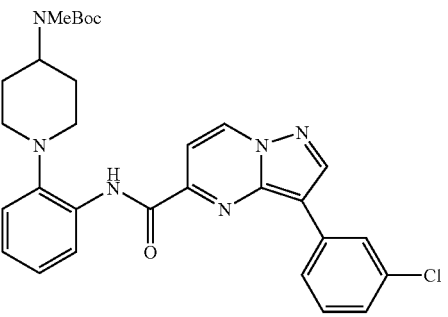 | A-152 | — | — |
| 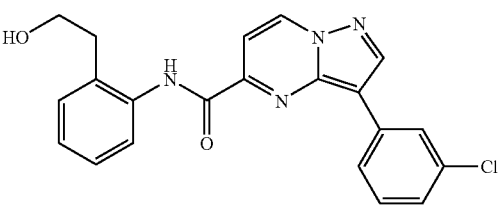 | A-153 | — | — |
| 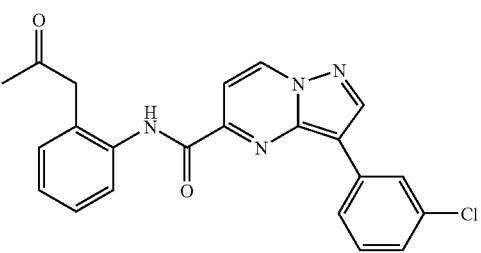 | A-154 | — | — |
| 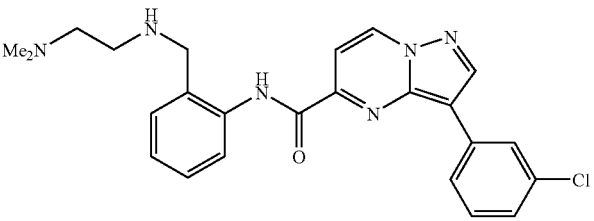 | A-155 | — | — |

TABLE 1-continued

| Chemical Formula | Compound No. | NMR | m. p. (° C.) |
|---|---|---|---|
| | A-156 | — | — |
| | A-157 | 1H-NMR(CDCl3) δ : 1.19–1.35(2H, m), 1.67–1.78(2H, m), 2.46–2.59(1H, m), 2.60–2.72(2H, m), 2.98–3.08(2H, m), 7.13–7.25(3H, m), 7.34(1H, ddd, J=7.8, 2.1, 1.2 Hz), 7.47(1H, t, J=7.8 Hz), 7.88–7.94(3H, m), 8.42–8.47(1H, m), 8.48(1H, s), 8.89(1H, d, J=z7.2 Hz), 10. | — |
| | A-158 | 1H-NMR(CDCl3) δ : 1.10–1.27(2H, m), 1.80–1.91(2H, m), 2.20–2.33(1H, m), 2.23(3H, s), 2.60–2.71(2H, m), 3.01–3.10(2H, m), 7.12–7.25(3H, m), 7.32–7.38(1H, m), 7.44–7.51(1H, m), 7.86–7.93(3H, m), 8.43–8.47(1H, m), 8.47(1H, s), 8.89(1H, d, J=7.2 Hz), 10.49–10.5 | — |
| | A-159 | 1H-NMR(CDCl3) δ : 1.41–1.57(2H, m), 1.66–1.77(2H, m), 1.92(6H,s), 2.27–2.41(1H, m), 2.62–2.74(2H, m), 3.08–3.19(2H, m), 7.12–7.32(4H, m), 7.42(1H, t, J=8.0 Hz), 7.88(1H, d, J=7.2 Hz), 7.87–7.95(1H, m), 8.03(1H, t, J=2.0 Hz), 8.37–8.43(1H, m), 8.52(1H, s), 8. | — |
| | A-160 | — | — |

TABLE 1-continued
| Chemical Formula | Compound No. | NMR | m. p. (° C.) |
|---|---|---|---|
| 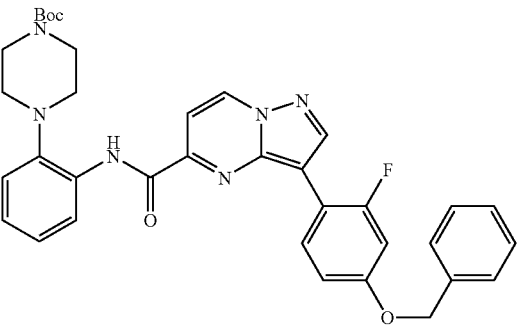 | A-161 | — | — |
| 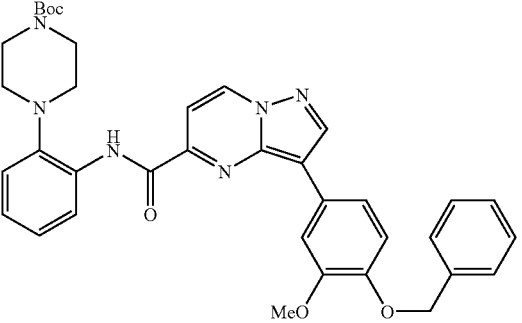 | A-162 | — | — |
| 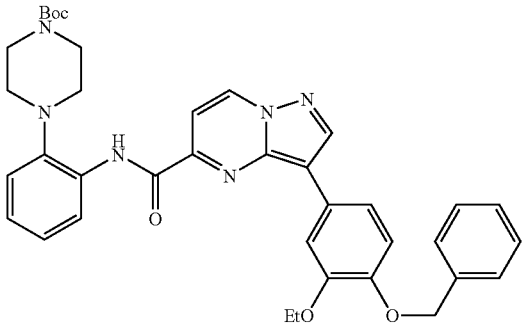 | A-163 | — | — |
| 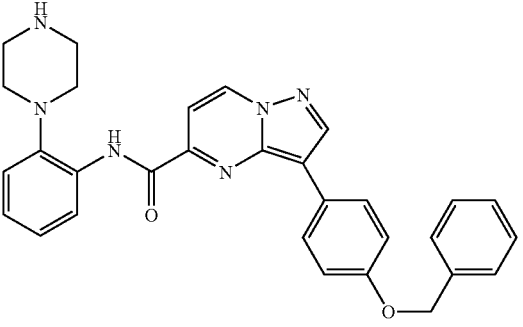 | A-164 | 1H-NMR(CDCl3) δ : 2.79–2.88(8H, m), 5.15(2H, s), 7.09–7.25(5H, m), 7.31–7.50(5H, m), 7.85(1H, d, J=7.2 Hz), 7.90(2H, d, J=8.7 Hz), 8.43(1H, s), 8.49–8.54(1H, m), 8.84(1H, d, J=7.2 Hz), 10.48–10.58(1H, br). | — |

TABLE 1-continued

| Chemical Formula | Compound No. | NMR | m. p. (° C.) |
|---|---|---|---|
| | A-165 | — | — |
| | A-166 | — | — |
| | A-167 | — | — |
| | A-168 | — | — |

TABLE 1-continued

| Chemical Formula | Compound No. | NMR | m. p. (° C.) |
|---|---|---|---|
| (structure) | A-169 | — | — |
| (structure) | A-170 | — | — |
| (structure) | A-171 | 1H-NMR(d6-DMSO) δ : 2.78(8H, s), 7.11(1H, dd, J=9.2, 9.2 Hz), 7.19(2H, m), 7.29(1H, m), 7.71(1H, d, J=7.2 Hz), 7.85–7.95(2H, m), 8.35(1H, m), 8.85(1H, s), 9.35(1H, d, J=7.2 Hz), 10.35(1H, s). | — |
| (structure) | A-172 | — | — |
| (structure) | A-173 | 1H-NMR(CDCl3) δ : 3.25(2H, t, J=8.2 Hz), 4.70(2H, t, J=8.2 Hz), 7.14(1H, t, J=7.3 Hz), 7.20–7.30(2H, m), 7.38(1H, t, J=7.3 Hz), 7.60(1H, d, J=7.3 Hz), 7.85(1H, t, J=7.3 Hz), 8.15(1H, s), 8.36(1H, d, J=7.3 Hz), 8.52(1H, 8.81(1H, d, J=7.7 Hz). | — |

TABLE 1-continued

| Chemical Formula | Compound No. | NMR | m. p. (° C.) |
|---|---|---|---|
| (structure) | A-174 | — | — |
| (structure) | A-175 | — | — |
| (structure) | A-176 | — | — |
| (structure) | A-177 | — | — |
| (structure) | A-178 | — | — |

TABLE 1-continued

| Chemical Formula | Compound No. | NMR | m. p. (° C.) |
|---|---|---|---|
| | A-179 | — | — |
| | A-180 | — | — |
| | A-181 | — | — |
| | A-182 | — | — |

TABLE 1-continued

| Chemical Formula | Compound No. | NMR | m. p. (° C.) |
|---|---|---|---|
| | A-183 | — | — |
| | A-184 | — | — |
| | A-185 | — | — |
| | A-186 | — | — |
| | A-187 | — | — |
| | A-188 | — | — |

TABLE 1-continued
| Chemical Formula | Compound No. | NMR | m. p. (° C.) |
|---|---|---|---|
| 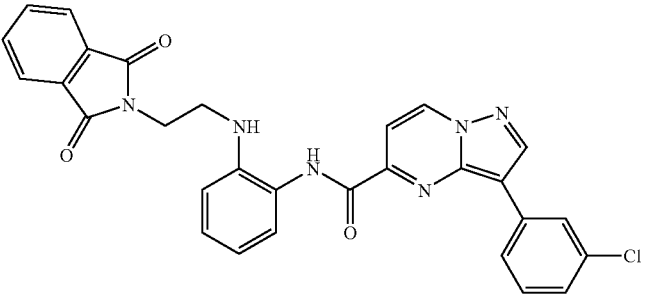 | A-189 | — | — |
| 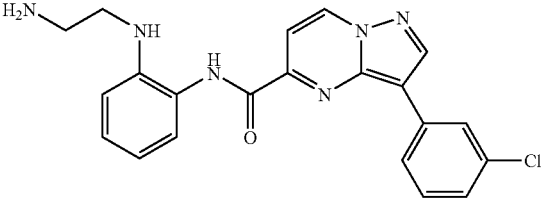 | A-190 | — | — |
| 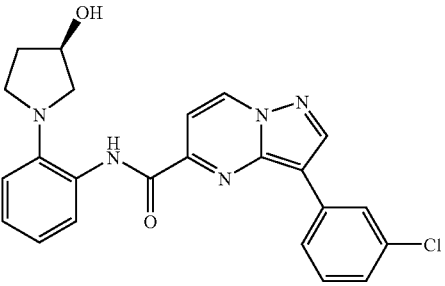 | A-191 | — | — |
| 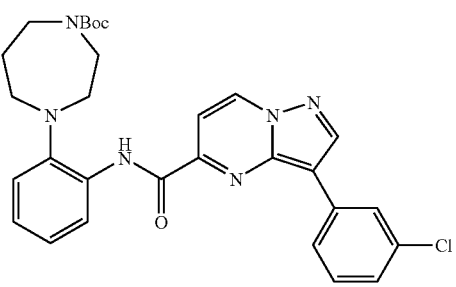 | A-192 | — | — |
| 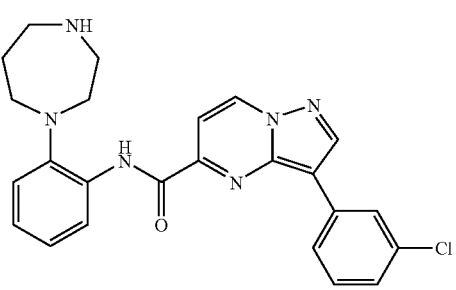 | A-193 | — | — |

TABLE 1-continued

| Chemical Formula | Compound No. | NMR | m. p. (° C.) |
|---|---|---|---|
| (structure) | A-194 | — | — |
| (structure) | A-195 | — | — |
| (structure) | A-196 | — | — |
| (structure) | A-197 | — | — |
| (structure) | A-198 | — | — |

TABLE 1-continued

| Chemical Formula | Compound No. | NMR | m. p. (° C.) |
|---|---|---|---|
| | A-199 | — | — |
| | A-200 | — | — |
| | A-201 | — | — |
| | A-202 | — | — |
| | A-203 | — | — |

TABLE 1-continued

| Chemical Formula | Compound No. | NMR | m. p. (° C.) |
|---|---|---|---|
| (structure) | A-204 | — | — |
| (structure) | A-205 | — | — |
| (structure) | A-206 | — | — |
| (structure) | A-207 | — | — |

TABLE 1-continued

| Chemical Formula | Compound No. | NMR | m. p. (° C.) |
|---|---|---|---|
| | A-208 | — | — |
| | A-209 | 1H-NMR(CDCl3) δ : 2.60(4H, m), 2.76(4H, m), 7.13–7.26(3H, m), 7.32(1H, t, J=7.7 Hz), 7.41(2H, t, J=7.7 Hz), 7.74(1H, s), 7.76(2H, d, J=7.7 Hz), 7.94(1H, d, J=7.3 Hz), 8.52(1H, m), 8.54(1H, s), 8.89(1H, d, J=7.3 Hz), 10.51(1H, s). | — |
| | A-210 | 1H-NMR(CDCl3) δ : 2.60(4H, m), 2.76(4H, m), 4.60(2H, s), 7.15–7.38(8H, m), 8.07(1H, d, J=7.2 Hz), 8.56(1H, dd, J=7.7, 2.0 Hz), 8.74(1H, s), 8.95(1H, d, J=7.2 Hz), 10.78(1H, s). | — |
| | A-211 | — | — |

TABLE 1-continued

| Chemical Formula | Compound No. | NMR | m. p. (° C.) |
|---|---|---|---|
| | A-212 | 1H-NMR(CDCl3) δ : 2.85(8H, s), 3.00(4H, s), 7.12–7.36(10H, m), 7.86(1H, d, J=7.2 Hz), 7.92(2H, d, J=8.4 Hz), 8.48(1H, s), 8.47–8.53(1H, m), 8.85(1H, d, J=7.2 Hz), 10.49–10.56(1H, br). | — |
| | A-212 | — | — |
| | A-213 | — | — |
| | A-214 | — | — |

TABLE 1-continued

| Chemical Formula | Compound No. | NMR | m. p. (° C.) |
|---|---|---|---|
| | A-215 | — | — |
| | A-216 | — | — |
| | A-217 | 1H-NMR(CDCl3) δ : 2.94(4H, m), 3.12(4H, m), 7.13–7.31(4H, m), 7.38(2H, t, J=7.5 Hz), 7.53(1H, d, J=16.2 Hz), 7.59(2H, d, J=7.5 Hz), 7.83(1H, d, J=7.2 Hz), 8.50(1H, s), 8.59(1H, d, J=7.5 Hz), 8.81(1H, d, J=7.2 Hz), 10.95(1H, s). | — |
| | A-218 | — | — |

TABLE 1-continued
| Chemical Formula | Compound No. | NMR | m. p. (° C.) |
|---|---|---|---|
| 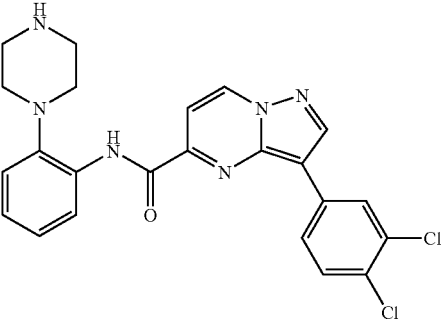 | A-219 | — | — |
| 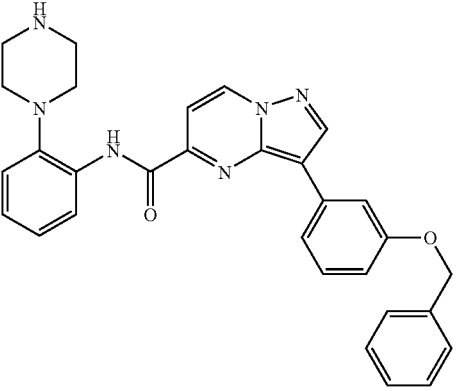 | A-220 | — | — |
| 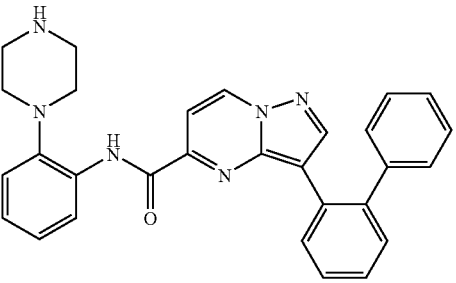 | A-221 | — | — |
| 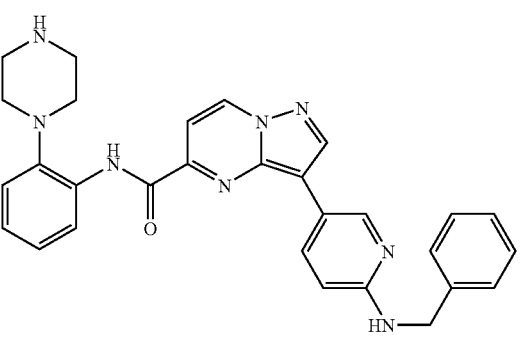 | A-222 | 1H-NMR(CDCl3) δ : 2.90–3.10(4H, m), 4.55(2H, s), 6.55(1H, d, J=7.4 Hz), 7.10–7.40(7H, m), 7.86(1H, dd, J=7.4, 2.2 Hz), 7.89(1H, d, J=7.4 Hz), 8.39(1H, s), 8.66(1H, dd, J=7.4, 2.2), 8.83(1H, d, J=7.4 Hz), 8.95(1H, d, J=2.2 Hz), 10.78(1H, br.s). | — |

TABLE 1-continued
| Chemical Formula | Compound No. | NMR | m. p. (° C.) |
|---|---|---|---|
| 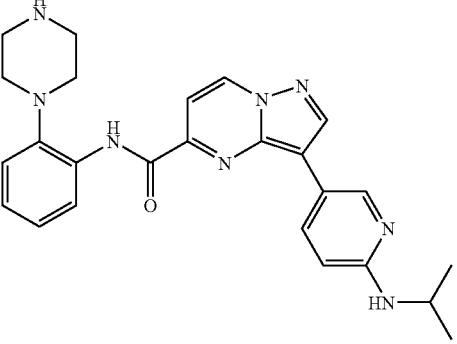 | A-223 | — | — |
| 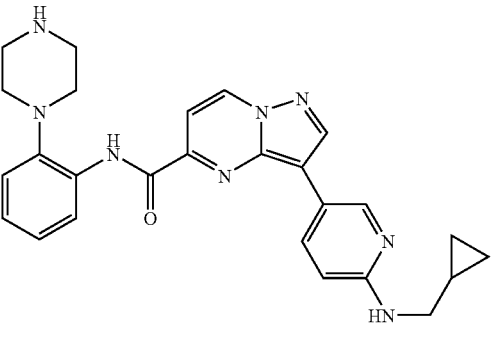 | A-224 | — | — |
| 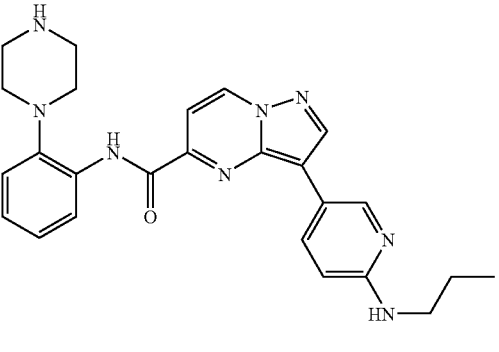 | A-225 | — | — |
| 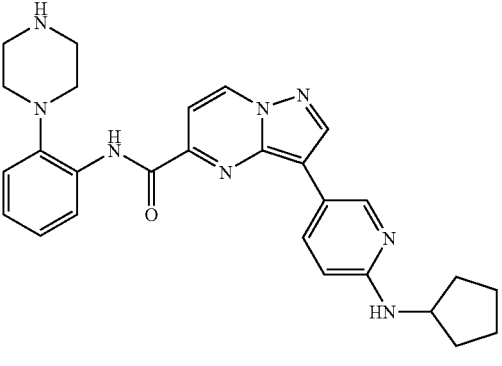 | A-226 | — | — |

TABLE 1-continued

| Chemical Formula | Compound No. | NMR | m. p. (° C.) |
|---|---|---|---|
| | A-227 | — | — |
| | A-228 | — | — |
| | A-229 | 1H-NMR(CDCl3) δ : 2.77–2.88(8H, m), 4.41(2H, s), 6.78(2H, d, J=8.1 Hz), 7.11–7.44(8H, m), 7.78(2H, d, J=8.1 Hz), 7.82(1H, d, J=7.2 Hz), 8.39(1H, s), 8.49–8.55(1H, m), 8.81(1H, d, J=7.2 Hz), 10.49–10.55(1H, br). | — |
| | A-230 | — | — |

TABLE 1-continued

| Chemical Formula | Compound No. | NMR | m. p. (° C.) |
|---|---|---|---|
| | A-231 | — | — |
| | A-232 | — | — |
| | A-233 | 1H-NMR(CDCl3) δ : 2.88–2.97(8H, m), 7.16–7.26(3H, m), 7.98–8.01(3H, m), 8.52(1H, m), 8.63(1H, s), 8.73(2H, dd, J=5.0, 1.7 Hz), 8.93(1H, d, J=6.9 Hz), 10.52(1H, s). | — |
| | A-234 | — | — |
| | A-235 | — | — |

TABLE 1-continued
| Chemical Formula | Compound No. | NMR | m. p. (° C.) |
|---|---|---|---|
| 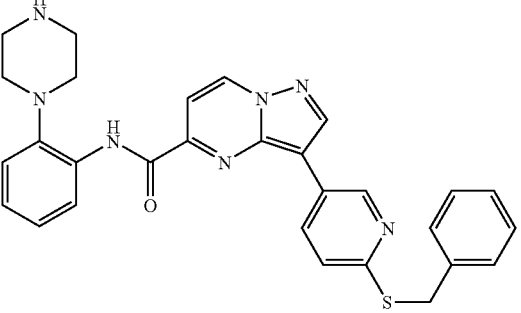 | A-236 | — | — |
| 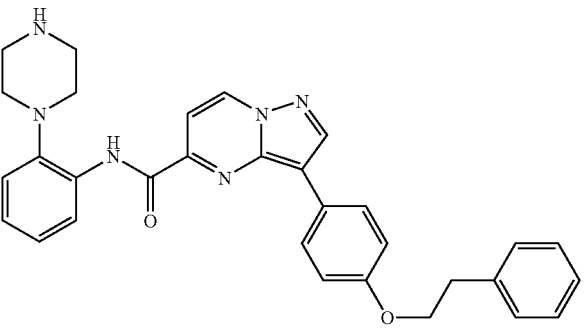 | A-237 | — | — |
| 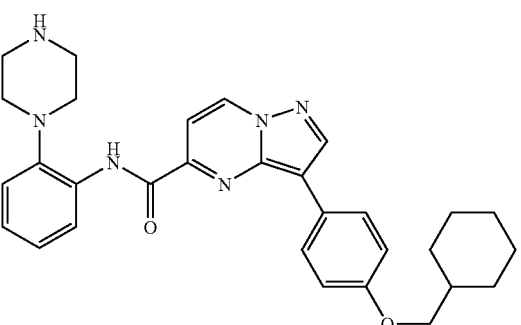 | A-238 | 1H-NMR(CDCl3) δ : 1.00–1.96(11H, m), 2.80–2.89(8H, m), 3.81(2H, d, J=6.3 Hz), 7.04(2H, d, J=8.7 Hz), 7.11–7.26(3H, m), 7.84(2H, d, J=8.7 Hz), 7.85(1H, d, J=7.2 Hz), 8.41(1H, s), 8.50–8.55(1H, m), 8.84(1H, d, J=7.2 Hz), 10.52–10.57(1H, br). | — |
| 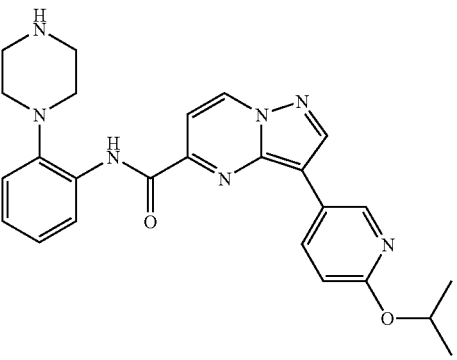 | A-239 | — | — |

TABLE 1-continued

| Chemical Formula | Compound No. | NMR | m. p. (° C.) |
|---|---|---|---|
| | A-240 | — | — |
| | A-241 | — | — |
| | A-242 | — | — |
| | A-243 | — | — |

TABLE 1-continued

| Chemical Formula | Compound No. | NMR | m. p. (° C.) |
|---|---|---|---|
| | A-244 | — | — |
| | A-245 | 1H-NMR(CDCl3) δ : 2.86(8H, s), 5.17(2H, s), 7.10–7.28(5H, m), 7.32–7.39(1H, m), 7.79–7.85(1H, 7.87(1H, d, J=7.2 Hz), 7.93(2H, d, J=8.7 Hz), 1.2 Hz), 8.71–8.74(1H, m), 8.85(1H, d, J=7.2 Hz), 10.49–10.56(1H, | — |
| | A-246 | 1H-NMR(CDCl3) δ : 2.85(8H, s), 5.16(2H,s), 7.09–7.26(6H, m), 7.35–7.40(2H, m), 7.86(1H, d, J=7.2 Hz), 7.90(2H, d, J=9.0 Hz), 8.43(1H, s), 8.49–8.54(1H, m), 8.85(1H, d, J=7.2 Hz), 10.50–10.56(1H, br). | — |
| | A-247 | — | — |

TABLE 1-continued
| Chemical Formula | Compound No. | NMR | m. p. (° C.) |
|---|---|---|---|
| 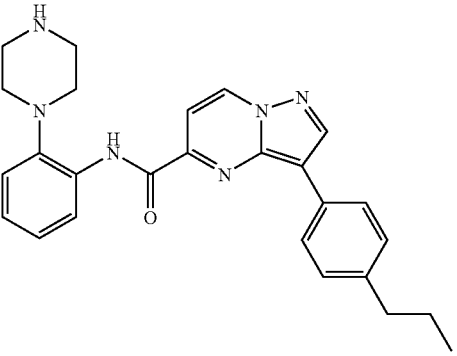 | A-248 | — | — |
| 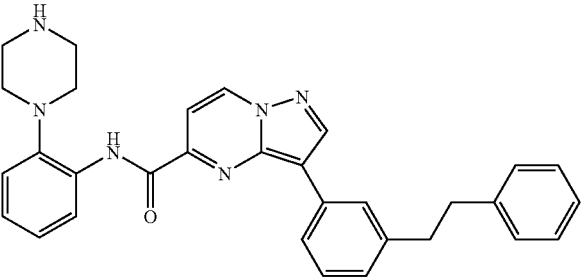 | A-249 | — | — |
| 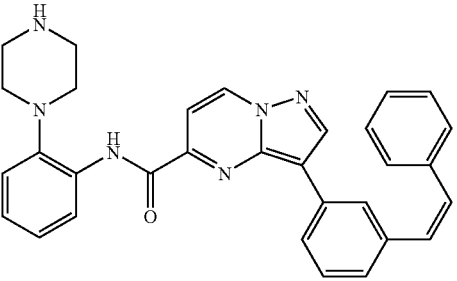 | A-250 | — | — |
| 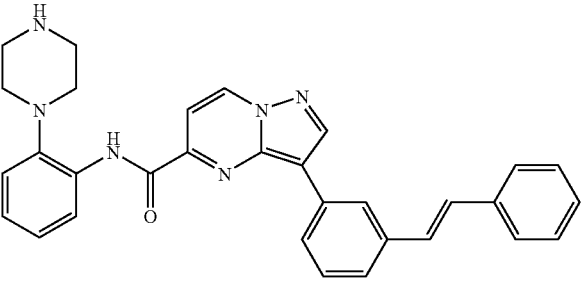 | A-251 | 1H-NMR(CDCl3) δ : 2.73–2.82(8H, m), 7.11–7.35(8H, m), 7.40–7.45(2H, m), 7.50–7.54(2H, m), 7.87–7.92(2H, m), 8.10(1H, s), 8.48–8.53(1H, m), 8.53(1H, s), 8.90(1H, d, J=7.2 Hz), 10.58–10.64(1H, br). | — |
| 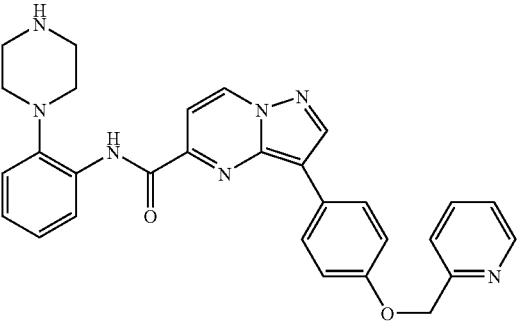 | A-252 | — | — |

TABLE 1-continued
| Chemical Formula | Compound No. | NMR | m. p. (° C.) |
|---|---|---|---|
|  | A-253 | — | — |
|  1.4 HCl | A-254 | 1H-NMR(d6-DMSO) δ : 2.88–2.95(4H, br), 3.30–3.37(4H, br), 7.17–7.37(4H, m), 7.44–7.51(4H, br), 7.53(1H, t, J=7.5 Hz), 7.79(1H, d, J=7.2 Hz), 7.99(1H, s), 8.05(1H, d, J=7.5 Hz), 8.38(1H, d, J=7.5 Hz), 8.91(1H, s), 9.43(1H, d, J=7.2 Hz), 10.40(1H, br.s). | — |
|  | A-255 | — | — |
| 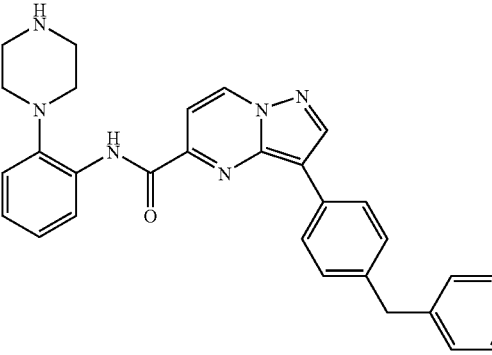 | A-256 | — | — |

TABLE 1-continued

| Chemical Formula | Compound No. | NMR | m. p. (° C.) |
|---|---|---|---|
| (structure) | A-257 | 1H-NMR(CDCl3) δ : 1.92–2.04(4H, m), 2.55(4H, t, J=4.8 Hz), 7.01–7.18(3H, m), 7.41–7.67(4H, m), 7.79–7.85(1H, m), 7.93(1H, d, J=7.2 Hz), 7.94–8.01(2H, m), 8.37(1H, s), 8.49–8.55(1H, m), 8.96(1H, d, J=7.2 Hz), 10.61–10.67(1H, br). | — |
| (structure) | A-258 | — | — |
| (structure) | A-259 | — | — |
| (structure) | A-260 | — | — |
| (structure) | A-261 | — | — |

TABLE 1-continued
| Chemical Formula | Compound No. | NMR | m. p. (° C.) |
|---|---|---|---|
| 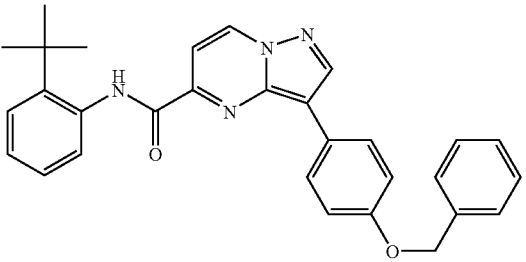 | A-262 | — | — |
| 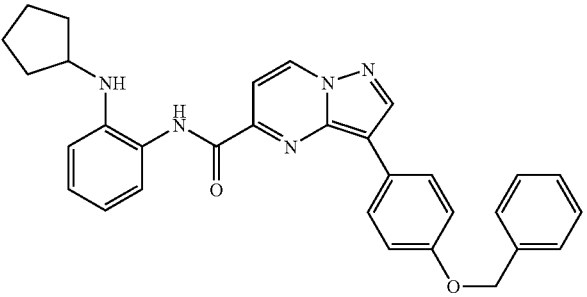 | A-263 | — | — |
| 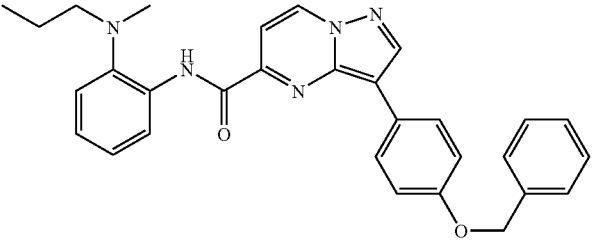 | A-264 | — | — |
| 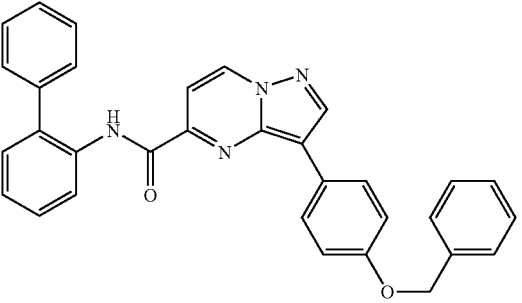 | A-265 | — | — |
| 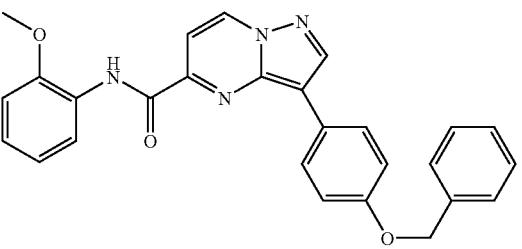 | A-266 | — | — |

TABLE 1-continued

| Chemical Formula | Compound No. | NMR | m. p. (° C.) |
|---|---|---|---|
| | A-267 | — | — |
| | A-268 | — | — |
| | A-269 | — | — |
| | A-270 | — | — |
| | A-271 | 1H-NMR(CDCl3) δ : 5.17(2H, s), 7.11(1H, d, J=3.5 Hz), 7.17(2H, d, J=8.9 Hz), 7.33–7.51(5H, m), 7.58(1H, d, J=3.5 Hz), 7.78(1H, d, J=7.1 Hz), 7.90(2H, d, J=8.9 Hz), 8.50(1H, s), 10.78(1H, s). | — |
| | A-272 | — | — |

TABLE 1-continued
| Chemical Formula | Compound No. | NMR | m. p. (° C.) |
|---|---|---|---|
| 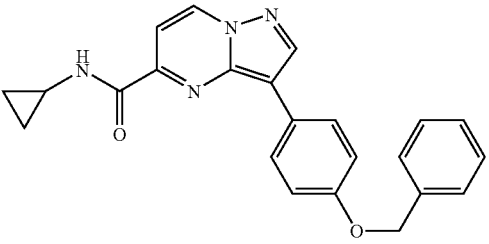 | A-273 | — | — |
| 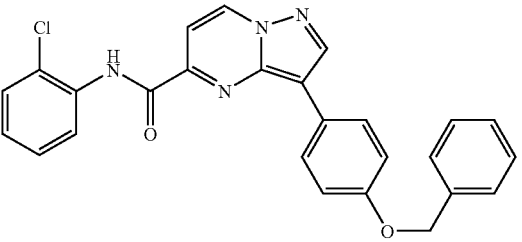 | A-274 | — | — |
| 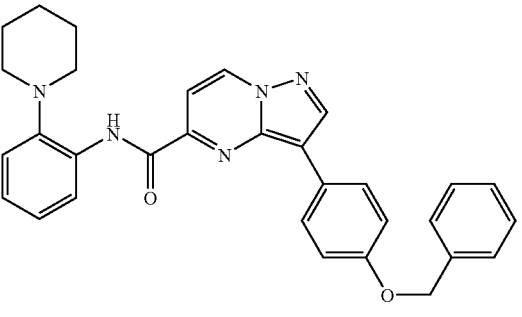 | A-275 | — | — |
| 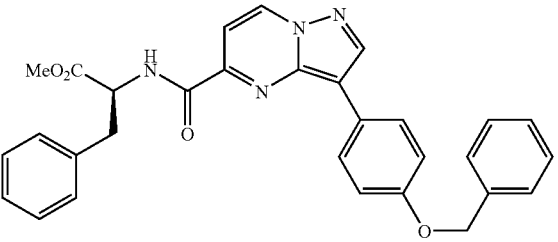 | A-276 | — | — |
| 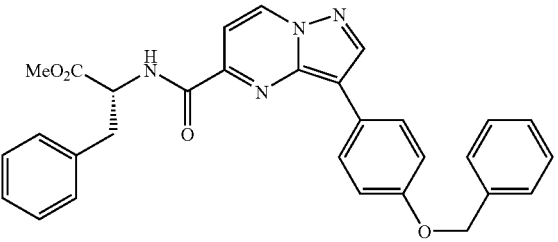 | A-277 | — | — |

TABLE 1-continued

| Chemical Formula | Compound No. | NMR | m. p. (° C.) |
|---|---|---|---|
| | A-278 | — | — |
| | A-279 | — | — |
| | A-280 | — | — |
| | A-281 | — | — |
| | A-282 | — | — |

TABLE 1-continued

| Chemical Formula | Compound No. | NMR | m. p. (° C.) |
|---|---|---|---|
| | A-283 | — | — |
| | A-284 | — | — |
| | A-285 | — | — |
| | A-286 | — | — |
| | A-287 | — | — |

TABLE 1-continued

| Chemical Formula | Compound No. | NMR | m. p. (° C.) |
|---|---|---|---|
| | A-288 | — | — |
| | A-289 | 1H-NMR(CDCl3) δ : 2.86(8H, s), 2.94–2.98(4H, m), 7.10–7.33(9H, m), 7.87(1H, d, J=7.2 Hz), 7.92(2H, d, J=8.1 Hz), 8.48(1H, s), 8.47–8.53(1H, m), 8.86(1H, d, J=7.2 Hz), 10.49–10.54(1H, br). | — |
| | A-290 | — | — |
| | A-291 | 1H-NMR(CDCl3) δ : 2.86(8H, s), 2.99(4H, s), 6.86–7.02(3H, m), 7.12–7.35(6H, m), 7.87(1H, d, J=7.2 Hz), 7.93(2H, d, J=8.4 Hz), 8.48(1H, s), 8.47–8.53(1H, m), 8.86(1H, d, J=7.2 Hz), 10.50–10.56(1H, br). | — |

TABLE 1-continued

| Chemical Formula | Compound No. | NMR | m. p. (° C.) |
|---|---|---|---|
| | A-292 | — | — |
| | A-293 | 1H-NMR(d6-DMSO) δ : 4.85(2H, br), 5.17(2H, s), 6.44–6.51(1H, m), 6.63(2H, d, J=6.6 Hz), 6.79(1H, d, J=7.2 Hz), 7.08(2H, d, J=8.9 Hz), 7.14(1H, s), 7.30–7.49(5H, m), 7.52(1H, d, J=7.2 Hz), 8.27(2H, d, J=8.9 Hz), 8.85(1H, s), 9.26(1H, d, J=7.2 Hz), 10.7(1H, br). | — |
| | A-294 | — | — |
| | A-295 | 1H-NMR(CDCl3) δ : 2.55(1H, br. t, J=6.0 Hz), 3.01(1H, dd, J=14.1, 7.2 Hz), 3.09(1H, dd, J=14.1, 7.2 Hz), 3.68–3.90(2H, m), 4.37(1H, m), 5.17(2H, s), 7.11(2H, d, J=9.0 Hz), 7.19–7.52(10H, m), 7.66(1H, d, J=7.2 Hz), 7.85(2 H, d, J=9.0 Hz), 8.04(1H, br.d, J=7.5 Hz), | — |
| | A-296 | — | — |

TABLE 1-continued

| Chemical Formula | Compound No. | NMR | m. p. (° C.) |
|---|---|---|---|
| | A-297 | — | — |
| | A-298 | — | — |
| | A-299 | — | — |
| | A-300 | — | — |
| | A-301 | 1H-NMR(CDCl3) δ : 2.87(8H, 7.37(7H, m), 7.56(2H, d, J=8.4 Hz), 7.88(1H, d, J=7.2 Hz), 7.93(2H, d, J=8.4 Hz), 8.49(1H, s), 8.48–8.54(1H, m), 8.87(1H, d, J=7.2 Hz), 10.54–10.56(1H, br). | — |

TABLE 1-continued

| Chemical Formula | Compound No. | NMR | m. p. (° C.) |
|---|---|---|---|
| | A-302 | — | — |
| | A-303 | 1H-NMR(CDCl3) δ : 1.43(1H, m), 1.83–1.94(3H, m), 2.37(2H, m), 2.73(2H, m), 3.24(2H, m), 3.63(2H, m), 4.09(2H, m), 5.15(2H, s), 7.21(2H, d, J=8.6 Hz), 7.33(1H, t, J=7.8 Hz), 7.40(2H, t, J=7.8 Hz), 7.48(2H, d, J=7.8 Hz), 7.62(1H, d, J=7.5 Hz), 8.10(2H, d, J=8.6 Hz | — |
| | A-304 | — | — |
| | A-305 | — | — |
| | A-306 | — | — |
| | A-307 | — | — |

TABLE 1-continued

| Chemical Formula | Compound No. | NMR | m. p. (° C.) |
|---|---|---|---|
| | A-308 | — | — |
| | A-309 | — | — |
| | A-310 | — | — |
| | A-311 | 1H-NMR(CDCl3) δ : 4.89(2H, d, J=6.0 Hz), 5.13(2H, s), 6.99(1H, dd, J=4.8, 3.6 Hz), 7.06–7.11(3H, m), 7.26(1H, dd, J=4.8, 1.5 Hz), 7.32–7.49(5H, m), 7.73(1H, d, J=7.4 Hz), 7.86(2H, d, J=8.9 Hz), 8.15(1H, br. t, J=6.0 Hz), 8.43(1H, s), 8.79(1H, d, J=7.4 Hz). | — |
| | A-312 | — | — |

TABLE 1-continued
| Chemical Formula | Compound No. | NMR | m. p. (° C.) |
|---|---|---|---|
| 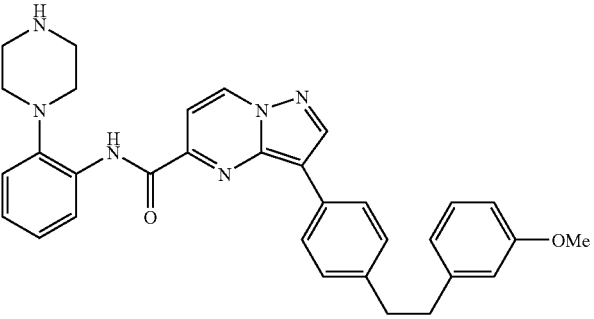 | A-313 | — | — |
| 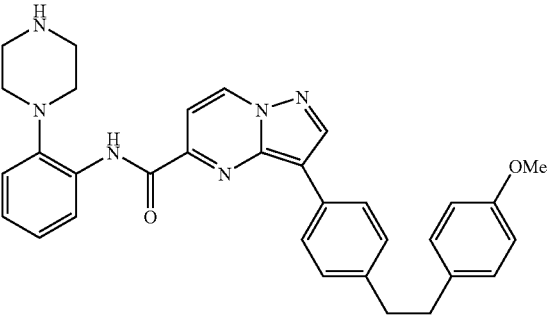 | A-314 | 1H-NMR(CDCl3) δ : 2.86(8H, s), 2.89–3.00(4H, m), 3.79(3H, s), 6.84(2H, d, J=8.4 Hz), 7.10–7.36(7H, m), 7.87(1H, d, J=7.2 Hz), 7.91(2H, d, J=8.4 Hz), 8.48(1H, s), 8.47–8.53(1H, m), 8.86(1H, d, J=7.2 Hz), 10.51–10.56(1H, br). | — |
| 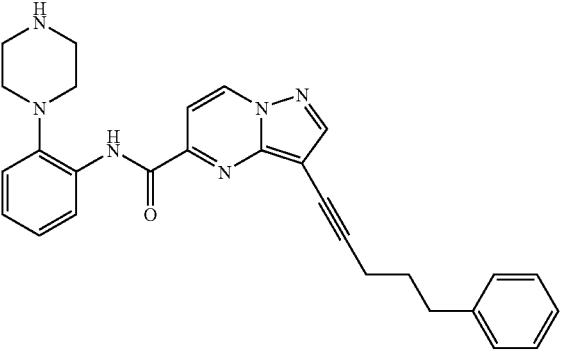 | A-315 | 1H-NMR(CDCl3) δ : 2.03(2H, quint, J=7.2 Hz), 2.58(2H, t, J=7.2 Hz), 2.83(2H, t, J=7.2 Hz), 2.87–2.93(4H, m), 3.10–3.18(4H, m), 7.11–7.34(8H, m), 7.85(1H, d, J=7.2 Hz), 8.31(1H, s), 8.54–8.60(1H, m), 8.80(1H, d, J=7.2 Hz), 10.97–11.04(1H, br). | — |
| 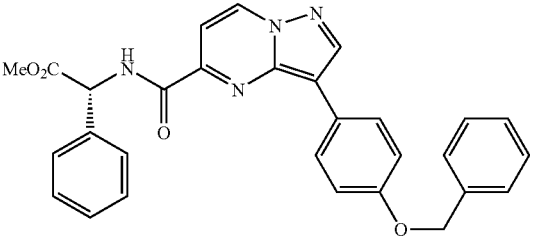 | A-316 | 1H-NMR(CDCl3) δ : 3.80(3H, s), 5.15(2H, s), 5.73(1H, d, J=7.2 Hz), 7.33–7.45(6H, m), 7.47–7.51(4H, m), 7.65(1H, d, J=7.1 Hz), 7.98(2H, d, J=9.0 Hz), 8.47(1H, s), 8.77(1H, d, J=7.1 Hz), 8.86(1H, br. d, J=7.2 Hz). | — |
| 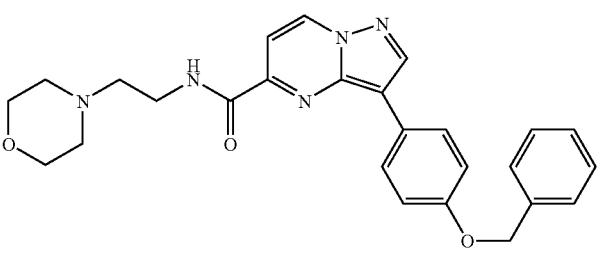 | A-317 | — | — |

TABLE 1-continued

| Chemical Formula | Compound No. | NMR | m. p. (° C.) |
|---|---|---|---|
| | A-318 | — | — |
| | A-319 | — | — |
| | A-320 | — | — |
| | A-321 | — | — |
| | A-322 | 1H-NMR(d6-DMSO) δ : 2.84–2.89(4H, m), 3.06–3.09(4H, m), 5.18(2H, s), 6.75(1H, m), 7.14(2H, d, J=8.9 Hz), 7.22–7.24(2H, m), 7.33(1H, t, J=7.5 Hz), 7.41(2H, t, J=7.5 Hz), 7.58(1H, d, J=7.2 Hz), 8.20(2H, d, J=8.9 Hz), 8.84(1H, s), 9.30(1H, d, J=7.2 Hz), 10.37(1H, s | — |

TABLE 1-continued

| Chemical Formula | Compound No. | NMR | m. p. (° C.) |
|---|---|---|---|
| | A-323 | — | — |
| | A-324 | 1H-NMR(CDCl3) δ : 0.91(6H, 7.25(3H, m), 7.33–7.45(2H, m), 7.79–7.85(2H, m), 7.92(1H, d, J=7.2 Hz), 8.42(1H, s), 8.48–8.53(1H, m), 8.89(1H, d, J=7.2 Hz), 10.56–10.63(1H, br). | — |
| | A-325 | 1H-NMR(d6-DMSO) δ : 2.89 (4H, s), 5.14(2H, s), 7.13(2H, d, J=8.7 Hz), 7.16–7.27(2H, m), 7.29–7.37(2H, m), 7.42(2H, t, J=7.2 Hz), 7.50–7.54(2H, m), 7.74(1H, d, J=7.4 Hz), 7.94(2H, d, J=8.7 Hz), 8.41(1H, dd, J=7.5, 1.8 Hz), 8.76(1H, s), 9.37(1H, d, J=7.4 Hz). | — |
| | A-326 | — | — |
| | A-327 | 1H-NMR(CDCl3) δ : 2.91–3.22(8H, m), 4.68–4.79(2H, m), 5.07–5.13(2H, m), 6.99–7.34(11H, m), 7.68–7.82(3H, m), 8.35–8.59(2H, m), 8.75–8.81(1H, m). | — |

TABLE 1-continued

| Chemical Formula | Compound No. | NMR | m. p. (° C.) |
|---|---|---|---|
| | A-328 | 1H-NMR(CDCl3) δ : 3.24–3.87(4H, m), 5.15(2H, s), 5.78–5.86(1H, m), 7.14–7.17(2H, m), 7.30–7.63(11H, m), 7.99–8.02(2H, m), 8.44(1H, s), 8.73(1H, m), 9.23–9.29(1H, m). | — |
| | A-329 | — | — |
| | A-330 | 1H-NMR(CDCl3) δ : 2.80–2.82(4H, br), 2.86–2.88(4H, br), 7.15–7.23(3H, m), 7.55(2H, d, J=8.7 Hz), 7.94(1H, d, J=7.2 Hz), 8.23(2H, d, J=8.7 Hz), 9.01(1H, s), 9.11(1H, d, J=2.1 Hz), 9.70(1H, d, J=1.8 Hz), 9.82(1H, s). | 264–266(d) |
| | A-331 | 1H-NMR(CDCl3) δ : 2.81(4H, br. d, J=4.8 Hz), 2.87(4H, br. d, J=5.4 Hz), 7.12–7.22(3H, m), 7.33–7.37(1H, m), 7.52(1H, t, J=7.8 Hz), 7.94(1H, d, J=7.2 Hz), 8.17(1H, dd, J=7.8, 1.2 Hz), 8.30(1H, t, J=1.8 Hz), 9.06(1H, s), 9.14(1H, d, J=2.1 Hz), 9.70(1H, s), 9.82(1H, s | 230–232 |

TABLE 1-continued

| Chemical Formula | Compound No. | NMR | m. p. (° C.) |
|---|---|---|---|
| (structure with piperazine, benzyl-NH-C(O)-pyrazolopyrimidine-4-chlorophenyl) | A-332 | 1H-NMR(CDCl3) δ : 2.81(4H, s), 2.85–2.87(4H, br. d, J=4.8 Hz), 4.64(2H, d, J=5.4 Hz), 7.07(1H, t, J=7.2 Hz), 7.13(1H, d, J=7.8 Hz), 7.26(1H, t, J=7.5 Hz), 7.35(1H, d, J=7.5 Hz), 7.54(2H, d, J=8.4 Hz), 8.21(2H, d, J=8.7 Hz), 8.95–8.97(1H, m), 9.08–9.09(1H, m), 9.19( | 210–212 |
| (structure with piperazine, benzyl-NH-C(O)-pyrazolopyrimidine-3-chlorophenyl) | A-333 | 1H-NMR(CDCl3) δ : 2.81(4H, s), 2.85–2.87(4H, m), 4.65(2H, d, J=5.7 Hz), 7.07(1H, t, J=7.2 Hz), 7.13(1H, d, J=7.8 Hz), 7.26(1H, t, J=7.8 Hz), 7.32–7.37(2H, m), 7.50(1H, t, J=8.1 Hz), 8.15(1H, dd, J=7.8, 0.9 Hz), 9.01–9.03(1H, m), 9.12(1H, t, J=2.1 Hz), 9.20(1H, br | 185–188 |
| (structure with aminoethyl-piperazine-phenyl-NH-C(O)-pyrazolopyrimidine-3-chlorophenyl) | A-334 | 1H-NMR(CDCl3) δ : 1.89(2H, t, J=6.2 Hz), 2.24–2.50(4H, br), 2.60(2H, t, J=6.2 Hz), 2.90(4H, t, J=4.5 Hz), 7.13–7.28(3H, m), 7.31(1H, ddd, J=8.1, 2.1, 1.2 Hz), 7.44(1H, t, J=7.8 Hz), 7.85–7.91(1H, m), 7.89(1H, d, J=7.2 Hz), 8.48(1H, m), | — |
| (structure with HO-CH2-CH(phenyl)-NH-C(O)-pyrazolopyrimidine-4-benzyloxyphenyl) | A-335 | — | — |

TABLE 1-continued

| Chemical Formula | Compound No. | NMR | m. p. (° C.) |
|---|---|---|---|
| | A-336 | — | — |
| | A-337 | — | — |
| | A-338 | — | — |
| | A-339 | 1H-NMR(CDCl3) δ : 1.05–1.31(3H, m),1.57–1.68(2H, m), 2.00(2H, d, J=6.3 Hz), 2.57–2.69(2H, m), 3.02–3.11(2H, m), 7.14–7.35(4H, m), 7.44(1H, t, J=8.0 Hz), 7.89(1H, d, J=7.2 Hz), 7.87–7.93(1H, m), 7.95(1H, t, J=1.8 Hz), 8.40–8.45(1H, m), 8.49(1H, s), 8.88(1H, d, | — |
| | A-340 | — | — |

TABLE 1-continued

| Chemical Formula | Compound No. | NMR | m. p. (° C.) |
|---|---|---|---|
| | A-341 | — | — |
| | A-342 | — | — |
| | A-343 | — | — |
| | A-344 | — | — |
| | A-345 | — | — |

TABLE 1-continued

| Chemical Formula | Compound No. | NMR | m. p. (° C.) |
|---|---|---|---|
| (structure) | A-346 | — | — |
| (structure) | A-347 | — | — |
| (structure) | A-348 | 1H-NMR(CDCl3) δ : 0.99(3H, J=7.2 Hz), 1.14–1.30(2H, m), 1.80–1.91(2H, m), 2.31–2.49(1H, m), 2.45(2H, q, J=7.2 Hz), 2.60–2.71(2H, m), 3.02–3.11(2H, m), 7.11–7.28(3H, m), 7.31–7.37(1H, m), 7.45–7.52(1H, m), 7.88–7.96(3H, m), 8.43–8.48(1H, m), 8.49(1H, s), 8 | — |
| (structure) | A-349 | — | — |

TABLE 1-continued

| Chemical Formula | Compound No. | NMR | m. p. (° C.) |
|---|---|---|---|
| | A-350 | — | — |
| | A-351 | — | — |
| | A-352 | — | — |
| | A-353 | — | — |
| | A-354 | — | — |

TABLE 1-continued

| Chemical Formula | Compound No. | NMR | m. p. (° C.) |
|---|---|---|---|
| (sec-butyl)NH-C(=N-[3-(3-chlorophenyl)pyrazolo[1,5-a]pyrimidin-5-yl])-OH | A-355 | — | — |
| (R)-(1-phenylethyl)NH-C(=N-[3-(3-chlorophenyl)pyrazolo[1,5-a]pyrimidin-5-yl])-OH | A-356 | — | — |
| ethyl 7-chloro-2-phenylpyrazolo[1,5-a]pyrimidine-5-carboxylate | A-357 | — | — |
| ethyl 2-phenylpyrazolo[1,5-a]pyrimidine-5-carboxylate | A-358 | — | — |
| 2-(pyridin-2-yl)pyrazolo[1,5-a]pyrimidine-5-carboxylic acid | A-359 | — | — |
| ethyl 3-[4-(benzyloxy)phenyl]pyrazolo[1,5-a]pyrimidine-5-carboxylate | A-360 | — | — |

TABLE 1-continued

| Chemical Formula | Compound No. | NMR | m. p. (° C.) |
|---|---|---|---|
| | A-361 | — | — |
| | A-362 | — | — |
| | A-363 | — | — |
| | A-364 | — | — |

TABLE 2

| Chemical Formula | Compound No. | NMR | m.p. (° C.) |
|---|---|---|---|
| (3-chlorophenyl-pyrazolo[1,5-a]pyrimidine-carboxamide with 2-(4-oxopiperidin-1-yl)phenyl) | B-1 | — | 212—212 |
| (3-(3-chlorophenyl)-pyrazolo[1,5-a]pyrimidine-carboxamide with biphenyl) | B-2 | — | — |
| (3-(3-chlorophenyl)-pyrazolo[1,5-a]pyrimidine-carboxamide with 2-(4-(methylamino)piperidin-1-yl)phenyl) | B-3 | — | 215–217 |

TABLE 2-continued
| Compound No. | Chemical Formula | NMR | m.p. (° C.) |
|---|---|---|---|
| B-4 | 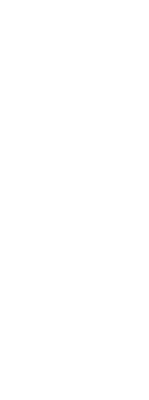 | — | — |
| B-5 | 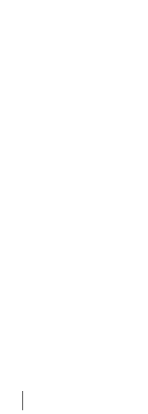 | — | 193–195 |
| B-6 |  | — | 187–189 |
| B-7 |  | — | — |

TABLE 2-continued
| Chemical Formula | Compound No. | NMR | m.p. (° C.) |
|---|---|---|---|
| 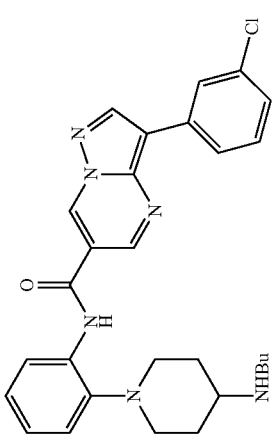 | B-8 | — | 191-192 |
| 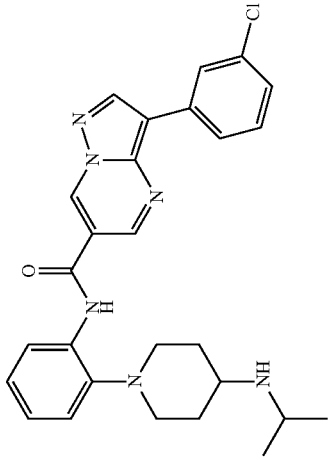 | B-9 | — | 206-208 |
| 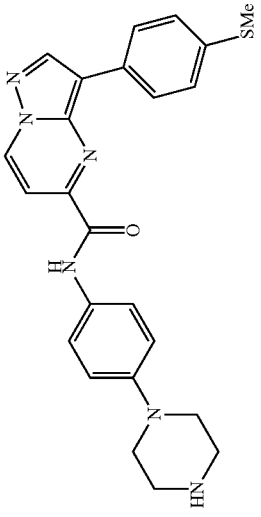 | B-10 | — | — |

TABLE 2-continued
| Compound No. | Chemical Formula | NMR | m.p. (° C.) |
|---|---|---|---|
| B-11 | 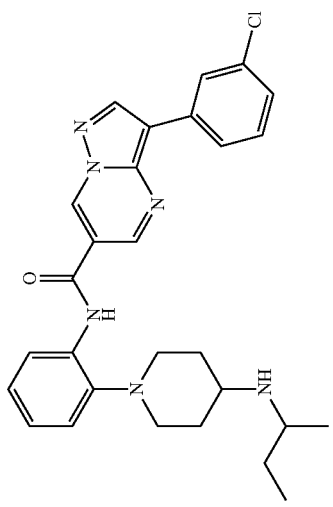 | — | 202–204 |
| B-12 | 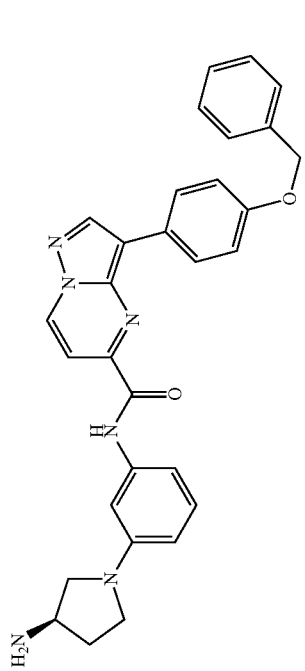 | — | — |
| B-13 | 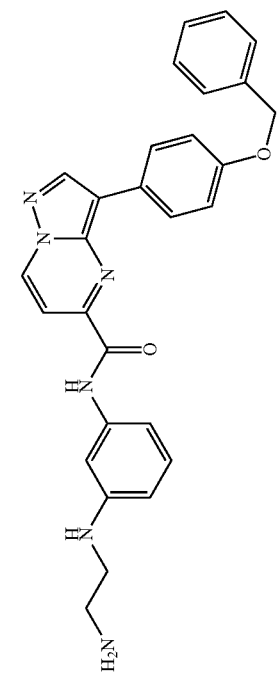 | — | — |

TABLE 2-continued

| Compound No. | Chemical Formula | NMR | m.p. (° C.) |
|---|---|---|---|
| B-14 | | — | — |
| B-15 | | — | — |
| B-16 | | — | 226–228 |

TABLE 2-continued
| Compound No. | Chemical Formula | NMR | m.p. (° C.) |
|---|---|---|---|
| B-17 | 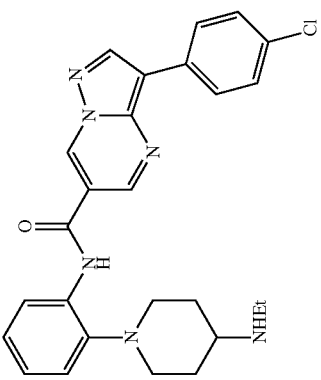 | — | 234–236 |
| B-18 | 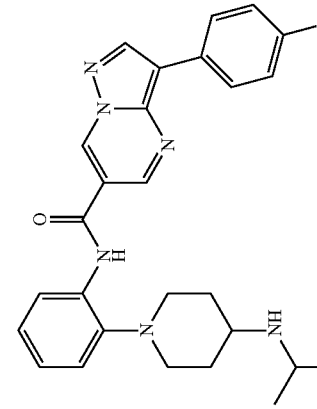 | — | 246–247 |
| B-19 | 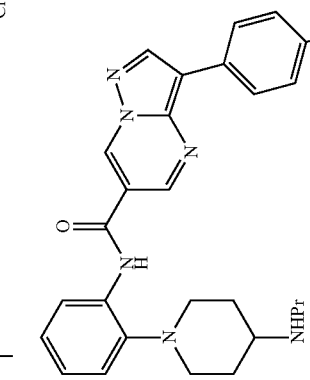 | — | 235–237 |

TABLE 2-continued

| Chemical Formula | Compound No. | NMR | m.p. (° C.) |
|---|---|---|---|
| (structure) | B-20 | — | 229–230 |
| (structure) | B-21 | — | — |
| (structure) | B-22 | — | — |

TABLE 2-continued
| Compound No. | NMR | m.p. (° C.) | Chemical Formula |
|---|---|---|---|
| B-23 | — | 222–224 | 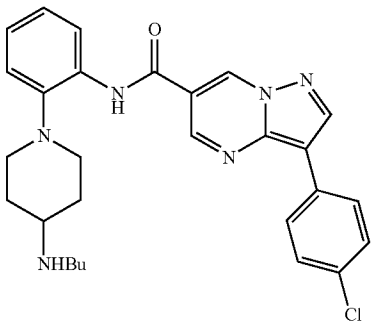 |
| B-24 | — | 256–261 | 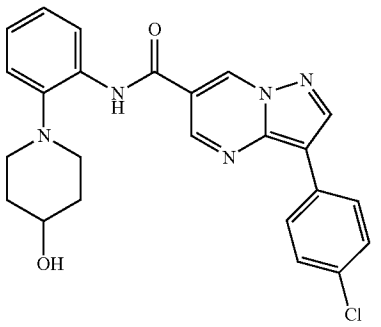 |
| B-25 | — | 134–136 | 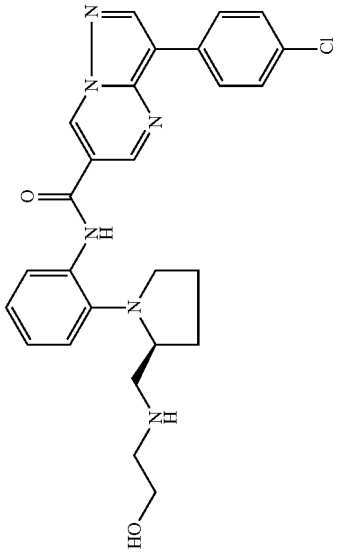 |

TABLE 2-continued

| Chemical Formula | Compound No. | NMR | m.p. (° C.) |
|---|---|---|---|
| (structure) | B-26 | 1H-NMR(CDCl3)δ: 2.03(2H, m), 2.57(2H, t, J=6.9Hz), 2.91(2H, t, J=7.5Hz), 6.74(2H, m), 7.02(2H, m), 7.20–7.31(6H, m), 7.57(1H, m), 7.82(1H, d, J=7.2Hz), 8.29(1H, s), 8.81(1H, d, J=7.2Hz), 9.71(1H, br-s). | — |
| (structure) | B-27 | 1H-NMR(d6-DMSO)δ: 5.18(2H, s), 7.15(2H, d, J=9.0Hz), 7.30–7.43(3H, m), 7.47–7.50(2H, m), 7.56–7.65(3H, m), 7.72(2H, m), 7.96(1H, m), 8.23(2H, d, J=9.0Hz), 8.32(1H, m), 8.69(2H, m), 8.86(1H, s), 9.33(1H, d, J=7.2Hz), 10.72(1H, s). | — |
| (structure) | B-28 | — | 184-186 |

TABLE 2-continued

| Chemical Formula | Compound No. | NMR | m.p. (° C.) |
|---|---|---|---|
| (structure) | B-29 | 1H-NMR(CDCl3)δ: 3.01(4H, s), 3.03–3.10(4H, m), 3.19–3.27(4H, m), 6.74–6.81(1H, m), 6.95–7.02(1H, m), 7.18–7.38(8H, m), 7.67(1H, t, J=2.1Hz), 7.80(1H, d, J=7.5Hz), 7.92(2H, dt, J=8.4, 1.8Hz), 8.52(1H, s), 8.85(1H, d, J=7.2Hz), 9.64–9.70(1H, br-s). | — |
| (structure) | B-30 | — | 203–204 |
| (structure) | B-31 | 1H-NMR(d6-DMSO)δ: 1.34(6H, t, J=6.9Hz), 2.73(8H, br), 3.97(4H, q, J=6.9Hz), 6.93(1H, s), 7.14–7.34(4H, m), 7.51(1H, t, J=7.8Hz), 8.16(1H, s), 8.25(1H, d, J=7.8Hz), 8.29–8.32(1H, m), 8.82(1H, s), 10.39(1H, br-s). | — |

TABLE 2-continued
| Compound No. | Chemical Formula | NMR | m.p. (° C.) |
|---|---|---|---|
| B-32 | 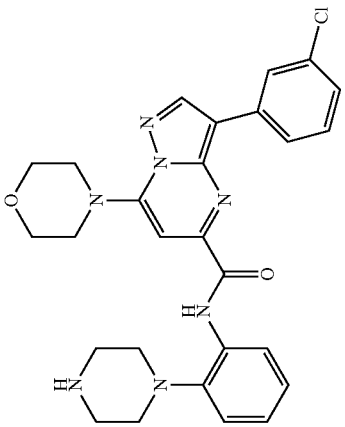 | — | — |
| B-33 | 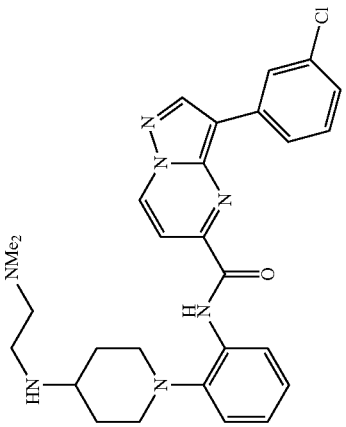 | 1H-NMR(CDCl3)δ: 1.22–1.38(2H, m), 1.80–1.91(2H, m), 2.18(6H, s), 2.28(2H, t, J=6.6Hz), 2.33–2.46(1H, m), 2.51(2H, t, J=6.6Hz), 2.60–2.74(1H, m), 3.02–3.13(2H, m), 7.11–7.27(3H, m), 7.29–7.35(1H, m), 7.48(1H, t, J=7.8Hz), 7.87–8.00(3H, m), 8.41–8.47(1H, m), 8.49(1H, s), 8.88(1H, d, J=7.2Hz), 10.45–10.51(1H, br-s). | — |
| B-34 | 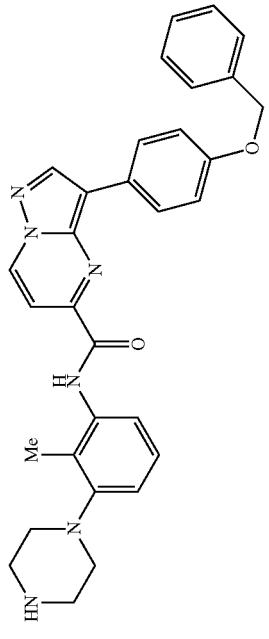 | — | — |

TABLE 2-continued

| Chemical Formula | Compound No. | NMR | m.p. (° C.) |
|---|---|---|---|
| (structure: 3-(naphthalen-2-yl)pyrazolo[1,5-a]pyrimidine-5-carboxamide, N-(4-(piperazin-1-yl)phenyl)) | B-35 | 1H-NMR(CDCl3)δ: 3.02–3.21(8H, m), 7.00(2H, dt, J=9.0, 2.1Hz), 7.47–7.59(2H, m), 7.69(2H, dt, J=9.0, 2.1Hz), 7.82–8.03(4H, m), 8.14(1H, dd, J=8.4, 1.5Hz), 8.50(1H, br-s), 8.66(1H, s), 8.88(1H, d, J=6.9Hz), 9.64–9.72(1H, br-s). | — |
| (structure: 3-(4-chlorophenyl)pyrazolopyridine urea with 2-(4-(methylamino)piperidin-1-yl)phenyl, i-PrOH) | B-36 | — | 137–140 |
| (structure: 3-(3-methoxyphenyl)pyrazolo[1,5-a]pyrimidine-5-carboxamide, N-(4-(piperazin-1-yl)phenyl)) | B-37 | — | — |

TABLE 2-continued

| Chemical Formula | Compound No. | NMR | m.p. (° C.) |
|---|---|---|---|
| | B-38 | — | 155–157 |
| | B-39 | — | — |

TABLE 2-continued
| Compound No. | NMR | m.p. (° C.) |
|---|---|---|
| B-40 | — | 196–197 |
| B-41 | — | 151–153 |
| B-42 | — | — |
Chemical Formula

TABLE 2-continued

| Chemical Formula | Compound No. | NMR | m.p. (° C.) |
|---|---|---|---|
| (structure) | B-43 | — | 152–153 |
| (structure) | B-44 | — | — |

TABLE 2-continued

| Compound No. | NMR | m.p. (° C.) |
|---|---|---|
| B-45 | — | — |
| B-46 | — | — |
| B-47 | — | — |

Chemical Formula: (structures not transcribed)

TABLE 2-continued
| Compound No. | Chemical Formula | NMR | m.p. (° C.) |
|---|---|---|---|
| B-48 | 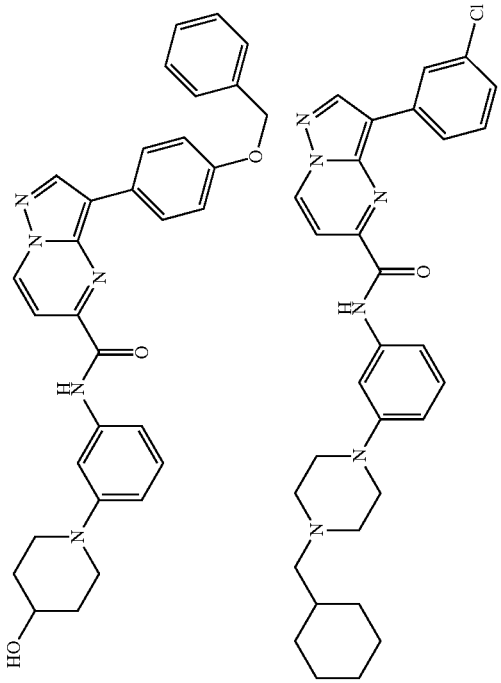 | — | — |
| B-49 | 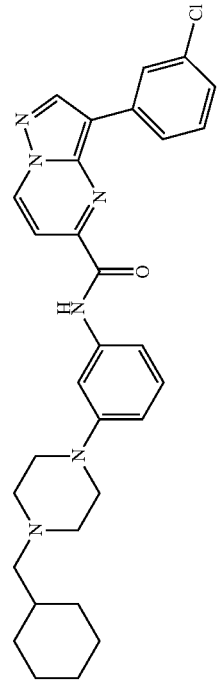 | — | — |
| B-50 | 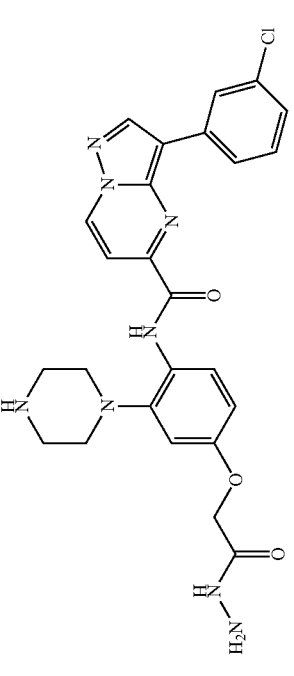 | — | — |

TABLE 2-continued

| Compound No. | NMR | m.p. (° C.) |
|---|---|---|
| B-51 | — | — |
| B-52 | 1H-NMR(CDCl3)δ: 1.13–1.29(2H, m), 1.53–1.63(2H, m), 1.72–2.00(2H, m), 2.36–2.50(1H, m), 2.60–2.72(2H, m), 2.58–2.71(4H, m), 2.99–3.11(2H, m), 3.76(2H, br-t, J=5.3Hz), 7.12–7.27(3H, m), 7.33–7.39(1H, m), 7.48(1H, t, J=7.8Hz), 7.88–7.95(3H, m), 8.44(1H, br-d, J=7.8Hz), 8.48(1H, s), 8.90(1H, d, J=7.2Hz), 10.48–10.56(1H, br-s). | — |
| B-53 | — | — |

TABLE 2-continued

| Chemical Formula | Compound No. | NMR | m.p. (° C.) |
|---|---|---|---|
| (structure) | B-54 | 1H-NMR(CDCl3)δ: 1.16(3H, t, J=7.2Hz), 1.88(1H, m), 2.27(1H, m), 2.74(2H, dq, J=7.2, 1.5Hz), 3.12(1H, m), 3.34(1H, m), 3.43-3.58(3H, m), 6.60(2H, d, J=9.0Hz), 7.32(1H, ddd, J=8.4, 2.1, 0.9Hz), 7.44(1H, t, J=7.8Hz), 7.65(2H, d, J=9.0Hz), 7.85(1H, dt, J=0.9, 8.4Hz), 7.86(1H, d, J=7.2Hz), 8.16(1H, t, J=1.8Hz), 8.53(1H, s), 8.85(1H, d, J=7.2Hz), 9.56(1H, s). | — |
| (structure) i-PrOH H₂O | B-55 | — | 117–128(d) |
| (structure) | B-56 | — | — |

TABLE 2-continued

| Compound No. | Chemical Formula | NMR | m.p. (° C.) |
|---|---|---|---|
| B-57 | (3-(3,5-difluorophenyl)pyrazolo[1,5-a]pyrimidine-5-carboxamide with 4-(piperazin-1-yl)aniline) | — | — |
| B-58 | (N-(3-(3-chlorophenyl)pyrazolo[1,5-a]pyrimidin-6-yl)-N'-(2-(4-(ethylamino)piperidin-1-yl)phenyl)urea); i-PrOH | — | 157–159(d) |

TABLE 2-continued
| Compound No. | Chemical Formula | NMR | m.p. (° C.) |
|---|---|---|---|
| B-59 | 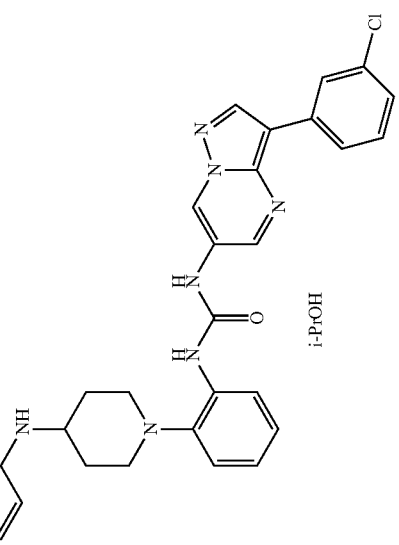 i-PrOH | — | 150-154(d) |
| B-60 | 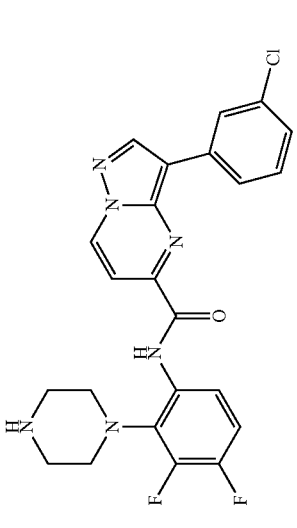 | — | — |
| B-61 | 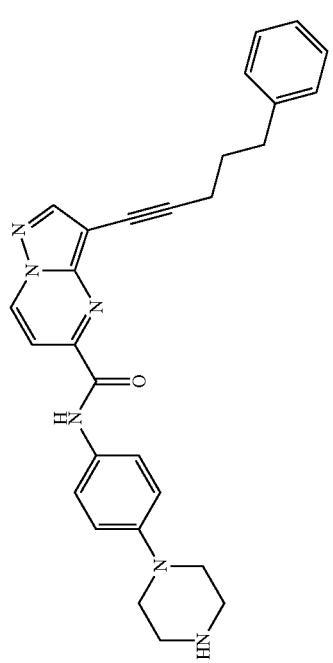 | — | — |

TABLE 2-continued

| Chemical Formula | Compound No. | NMR | m.p. (° C.) |
|---|---|---|---|
| (structure) | B-62 | — | — |
| (structure) | B-63 | 1H-NMR(CDCl3)δ: 1.20–1.37(2H, m), 1.78–1.90(2H, m), 2.36–2.50(1H, m), 2.55(2H, br-t, J=5.3Hz), 2.60–2.72(2H, m), 3.02–3.13(2H, m), 3.49(2H, br-t, J=5.3Hz), 7.13–7.28(3H, m), 7.31–7.36(1H, m), 7.47(1H, t, J=7.8Hz), 7.88–7.96(3H, m), 8.44(1H, br-d, J=7.5Hz),8.49(1H, s), 8.90(1H, d, J=7.5Hz), 10.48–10.55(1H, br-s). | — |
| (structure) | B-64 | 1H-NMR(CDCl3)δ: 3.03–3.07(4H, m), 3.20–3.24(4H, m), 4.23(1H, br), 4.43(2H, br), 6.74–6.83(3H, m), 6.99(1H, m), 7.26–7.45(6H, m), 7.63(1H, t, J=2.1Hz), 7.74(1H, d, J=7.5Hz), 7.82(2H, d, J=8.4Hz), 8.42(1H, s), 8.80(1H, d, J=7.5Hz), 9.66(1H, s). | — |

TABLE 2-continued

| Chemical Formula | Compound No. | NMR | m.p. (° C.) |
|---|---|---|---|
| (3-chlorophenyl-pyrazolopyridine carboxamide with 2-(4-isobutylaminopiperidin-1-yl)phenyl) | B-65 | 1H-NMR(CDCl3)δ: 0.88(6H, d, J=6.6Hz), 1.19–1.35(2H, m), 1.45–1.65(1H, m), 1.80–1.91(2H, m), 2.24(2H, d, J=6.6Hz), 2.29–2.43(1H, m), 2.61–2.73(2H, m), 3.02–3.13(2H, m), 7.11–7.34(4H, m), 7.48(1H, t, J=7.8Hz), 7.87–8.00(3H, m), 8.41–8.47(1H, m), 8.50(1H,s), 8.88(1H, d, J=7.2Hz), 10.45–10.52(1H, br-s). | — |
| (3-chlorophenyl-pyrazolopyridine carboxamide with 2-(piperazin-1-yl)-5-fluorophenyl) | B-66 | 1H-NMR(d6-DMSO)δ: 2.74(8H, br), 7.02(1H, td, J=8.4, 3.0Hz), 7.33–7.41(2H, m), 7.57(1H, t, J=8.1Hz), 7.76(1H, d, J=7.5Hz), 8.11(1H, s), 8.20–8.24(2H, m), 9.00(1H, s), 9.42(1H, d, J=7.5Hz), 10.48(1H, br-s). | — |
| (3-chlorophenyl-pyrazolopyridine carboxamide with 2-(piperazin-1-yl)-4-(carboxymethoxy)phenyl)·HCl | B-67 | — | — |

TABLE 2-continued
| Chemical Formula | Compound No. | NMR | m.p. (° C.) |
|---|---|---|---|
|  | B-68 | — | — |
|  | B-69 | — | — |
|  | B-70 | — | — |

TABLE 2-continued

| Compound No. | Chemical Formula | NMR | m.p. (° C.) |
|---|---|---|---|
| B-71 | 3-(3-chlorophenyl)-N-methyl-N-[4-(piperazin-1-yl)phenyl]pyrazolo[1,5-a]pyrimidine-5-carboxamide | — | — |
| B-72 | 3-{4-[(cyclohexylmethyl)amino]phenyl}-N-{3-[4-(2-hydroxyethyl)piperazin-1-yl]phenyl}pyrazolo[1,5-a]pyrimidine-5-carboxamide | — | — |
| B-73 | 3-(3-chlorophenyl)-N-[5-(carbamoylamino)-2-(piperazin-1-yl)phenyl]pyrazolo[1,5-a]pyrimidine-5-carboxamide | — | — |

TABLE 2-continued

| Compound No. | Chemical Formula | NMR | m.p. (° C.) |
|---|---|---|---|
| B-74 | | — | — |
| B-75 | | — | — |
| B-76 | | — | — |

TABLE 2-continued

| Chemical Formula | Compound No. | NMR | m.p. (° C.) |
|---|---|---|---|
| (structure) | B-77 | 1H-NMR(CDCl3)δ: 1.02(2H, m), 1.22–1.32(3H, m), 1.59–1.90(5H, m), 3.03–3.07(6H, m), 3.22(4H, m), 6.74–6.78(3H, m), 7.02(1H, dd,J=7.8, 1.8Hz), 7.29(1H, t, J=7.8Hz), 7.63(1H, t, J=2.1Hz), 7.74(1H, d, J=7.5Hz),7.80(2H, d, J=9.0Hz), 8.42(1H, s), 8.80(1H, d, J=7.5Hz), 9.68(1H, s). | — |
| (structure) | B-78 | — | — |
| (structure) | B-79 | — | — |

TABLE 2-continued

| Compound No. | Chemical Formula | NMR | m.p. (° C.) |
|---|---|---|---|
| B-80 | 3-(3,5-dichlorophenyl)-N-(4-cyanophenyl)pyrazolo[1,5-a]pyrimidine-5-carboxamide | — | — |
| B-81 | 3-(3-chlorophenyl)-N-[3-(4-ethylaminopiperidin-1-yl)phenyl]pyrazolo[1,5-a]pyrimidine-5-carboxamide | — | — |
| B-82 | 3-(3-chlorophenyl)-N-[4-methyl-2-(piperazin-1-yl)phenyl]pyrazolo[1,5-a]pyrimidine-5-carboxamide | — | — |

TABLE 2-continued

| Compound No. | Chemical Formula | NMR | m.p. (° C.) |
|---|---|---|---|
| B-83 | (structure) | 1H-NMR(CDCl3)δ: 3.07(4H, m), 3.16(4H, m), 6.99(2H, d, J=9.0Hz), 7.45(1H, t, J=7.8Hz), 7.69(2H, d, J=9.0Hz), 7.73(1H, m), 7.84(1H, m), 7.88(1H, d, J=7.2Hz), 8.17(1H, t, J=1.8Hz), 8.54(1H, s), 8.87(1H, d, J=7.2Hz), 9.63(1H, s). | — |
| B-84 | (structure) | — | — |
| B-85 | (structure) | 1H-NMR(d6-DMSO)δ: 2.76(8H, br), 6.90(1H, s), 7.12–7.62(9H, m), 8.21(1H, s), 8.24–8.34(2H, m), 9.00(1H, s), 10.43(1H, br-s). | — |

TABLE 2-continued

| Chemical Formula | Compound No. | NMR | m.p. (° C.) |
|---|---|---|---|
| (structure) | B-86 | — | — |
| (structure) | B-87 | 1H-NMR(CDCl3)δ: 3.04(4H, m), 3.12(3H, s), 3.22(4H, m), 4.63(2H, s), 6.75(1H, m), 6.90(2H, d, J=9.0Hz), 6.98(1H, m), 7.24–7.37(6H, m), 7.63(1H, t, J=2.1Hz), 7.73(1H, d, J=7.5Hz), 7.85(2H, d, J=9.0Hz), 8.43(1H, s), 8.78(1H, d, J=7.5Hz), 9.66(1H, br-s). | — |
| (structure) | B-88 | — | — |

TABLE 2-continued

| Compound No. | Chemical Formula | NMR | m.p. (° C.) |
|---|---|---|---|
| B-89 | | — | — |
| B-90 | | — | — |
| B-91 | | 1H-NMR(CDCl3)δ: 1.08–1.25(2H, m), 1.30–1.71(3H, m), 1.88(2H, d, J=6.9Hz), 2.56–2.68(4H, m), 3.01–3.11(2H, m), 3.51–3.58(2H, m), 7.13–7.34(4H, m), 7.43(1H, t, J=7.8Hz),7.89–7.97(2H, m), 7.90(1H, d, J=7.2Hz), 8.40–8.45(1H, m), 8.49(1H, s), 8.88(1H, d, J=7.2Hz), 10.50–10.57(1H, br-s). | — |

TABLE 2-continued

| Chemical Formula | Compound No. | NMR | m.p. (° C.) |
|---|---|---|---|
| | B-92 | — | — |
| | B-93 | — | — |

TABLE 2-continued

| Compound No. | Chemical Formula | NMR | m.p. (° C.) |
|---|---|---|---|
| B-94 | (structure) | — | — |
| B-95 | (structure) | — | — |
| B-96 | (structure) | — | — |

TABLE 2-continued

| Compound No. | Chemical Formula | NMR | m.p. (° C.) |
|---|---|---|---|
| B-97 | | — | — |
| B-98 | | — | — |
| B-99 | | — | — |

TABLE 2-continued

| Chemical Formula | Compound No. | NMR | m.p. (° C.) |
|---|---|---|---|
| (structure) | B-100 | — | — |
| (structure) | B-101 | — | — |

TABLE 2-continued
| Chemical Formula | Compound No. | NMR | m.p. (° C.) |
|---|---|---|---|
| 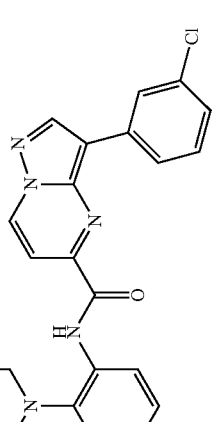 | B-102 | — | — |
| 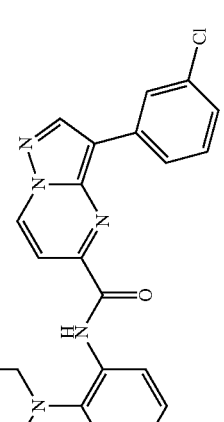 | B-103 | — | — |

TABLE 2-continued

| Chemical Formula | Compound No. | NMR | m.p. (° C.) |
|---|---|---|---|
| | B-104 | — | — |
| | B-105 | — | — |
| | B-106 | — | — |

TABLE 2-continued

| Chemical Formula | Compound No. | NMR | m.p. (° C.) |
|---|---|---|---|
| (structure) | B-107 | — | — |
| (structure) | B-108 | — | — |
| (structure) | B-109 | — | — |

TABLE 2-continued

| Chemical Formula | Compound No. | NMR | m.p. (° C.) |
|---|---|---|---|
| (structure) | B-110 | 1H-NMR(CDCl3)δ: 1.28(6H, d, J=6.6Hz), 3.05(4H, m), 3.21(4H, m), 4.38(1H, sept, J=6.6Hz), 4.51(2H, s), 6.75(1H, m), 6.87(2H, d, J=9.0Hz), 6.97(1H, m), 7.24–7.34(6H, m), 7.61(1H, m), 7.72(1H, d, J=7.2Hz), 7.79(2H, d, J=9.0Hz), 8.40(1H, s), 8.78(1H, d, J=7.2Hz), 9.64(1H, s). | — |
| (structure) | B-111 | — | — |
| (structure) | B-112 | — | — |

TABLE 2-continued

| Compound No. | Chemical Formula | NMR | m.p. (° C.) |
|---|---|---|---|
| B-113 | (ethyl 4-(4-(2-((3-(3-chlorophenyl)pyrazolo[1,5-a]pyrimidine-5-carboxamido)phenyl)piperazin-1-yl)butanoate) | — | — |
| B-114 | (2-(4-(4-(2-((3-(3-chlorophenyl)pyrazolo[1,5-a]pyrimidine-5-carboxamido)phenyl)piperazin-1-yl)acetic acid) | — | — |

TABLE 2-continued
| Compound No. | Chemical Formula | NMR | m.p. (° C.) |
|---|---|---|---|
| B-115 | 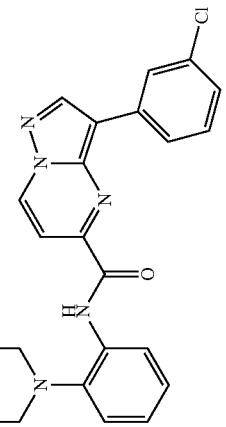 | — | — |
| B-116 | 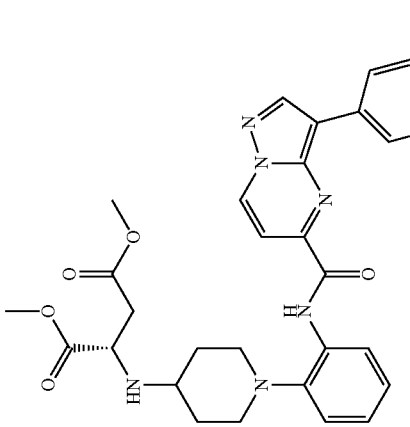 | — | — |

TABLE 2-continued

| Compound No. | NMR | m.p. (° C.) |
|---|---|---|
| B-117 | — | — |
| B-118 | — | — |
| B-119 | — | — |

TABLE 2-continued

| Compound No. | Chemical Formula | NMR | m.p. (° C.) |
|---|---|---|---|
| B-120 | | — | — |
| B-121 | | — | — |
| B-122 | | — | — |

TABLE 2-continued
| Compound No. | Chemical Formula | NMR | m.p. (° C.) |
|---|---|---|---|
| B-123 | 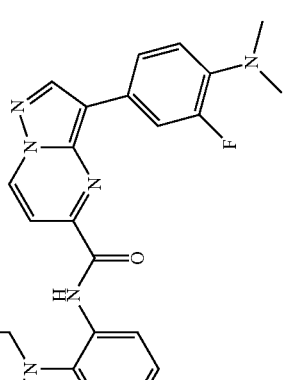 | — | — |
| B-124 | 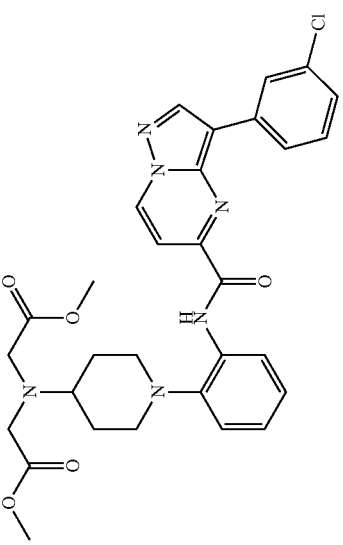 | — | — |

TABLE 2-continued

| Compound No. | Chemical Formula | NMR | m.p. (° C.) |
|---|---|---|---|
| B-125 | (structure) | — | — |
| B-126 | (structure) | — | — |
| B-127 | (structure) | 1H-NMR(CDCl3)δ: 0.99(2H, m), 1.12–1.31(3H, m), 1.64–1.86(6H, m), 3.04–3.07(7H, m), 3.21–3.25(6H, m), 6.76(1H, m), 6.82(2H, d, J=8.7Hz), 7.04(1H, m), 7.29(1H, t, J=7.2Hz), 7.62(1H, t, J=2.1Hz), 7.73(1H, d, J=7.2Hz), 7.85(2H, d, J=8.7Hz), 8.43(1H, s), 8.80(1H, d, J=7.2Hz), 9.68(1H, s). | — |

TABLE 2-continued

| Chemical Formula | Compound No. | NMR | m.p. (° C.) |
|---|---|---|---|
| [structure] | B-128 | — | — |
| [structure] | B-129 | — | — |
| [structure] | B-130 | — | — |

TABLE 2-continued

| Chemical Formula | Compound No. | NMR | m.p. (° C.) |
|---|---|---|---|
| (structure) | B-131 | 1H-NMR(CDCl3)δ: 2.81–2.88(8H, m), 5.15(2H, s), 7.13(2H, d, J=9.0Hz), 7.23(1H, d, J=7.5Hz), 7.32–7.48(6H, m), 7.83–7.88(3H, m), 8.43(1H, s), 8.85–8.88(2H, m), 10.46(1H, s). | — |
| (structure) | B-132 | — | — |
| (structure) | B-133 | 1H-NMR(CDCl3)δ: 2.01(2H, br-t, J=5.4Hz), 2.29–2.54(4H, br), 2.90(4H, t, J=4.7Hz), 3.45(2H, t, J=5.4Hz), 7.13–7.33(4H, m), 7.43(1H, t, J=8.1Hz), 7.85(1H, dt, J=7.5, 1.4Hz), 7.89(1H, d, J=7.2Hz), 7.94(1H, t, J=1.8Hz), 8.45(1H, br-d, J=7.5Hz), 8.48(1H, s), 8.89(1H, d, J=7.2Hz), 10.51–10.58(1H, br-s). | — |

TABLE 2-continued

| Compound No. | Chemical Formula | NMR | m.p. (° C.) |
|---|---|---|---|
| B-134 | 3-(3-chlorophenyl)-N-(2-(4-(2-(2-hydroxyethoxy)ethyl)piperazin-1-yl)phenyl)pyrazolo[1,5-a]pyrimidine-6-carboxamide | — | — |
| B-135 | sodium 2-((1-(2-(3-(3-chlorophenyl)pyrazolo[1,5-a]pyrimidine-6-carboxamido)phenyl)piperidin-4-yl)amino)acetate | — | — |
| B-136 | 3-(3-chlorophenyl)-7-(cyclopropylamino)-N-(3-(piperazin-1-yl)phenyl)pyrazolo[1,5-a]pyrimidine-5-carboxamide | — | — |

TABLE 2-continued
| Chemical Formula | Compound No. | NMR | m.p. (° C.) |
|---|---|---|---|
| 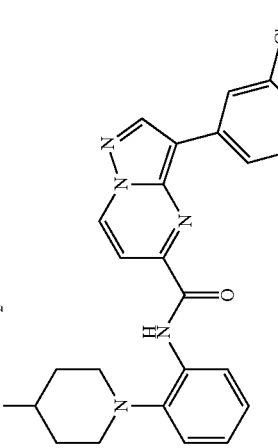 | B-137 | — | — |
| 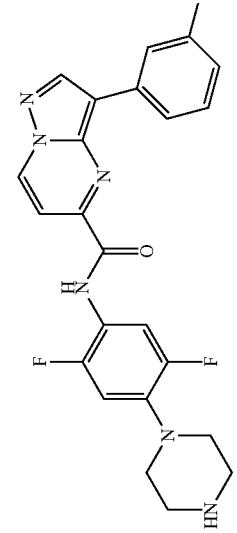 | B-138 | — | — |
| 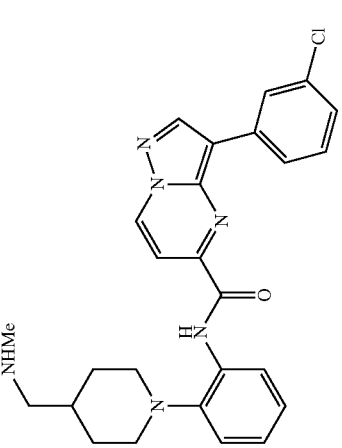 | B-139 | 1H-NMR(CDCl3)δ: 1.08–1.25(2H, m), 1.30–1.67(3H, m), 1.84(2H, d, J=6.6Hz), 2.30(3H, s), 2.56–2.68(2H, m), 3.01–3.10(2H, m), 7.13–7.34(4H, m), 7.44(1H, t, J=8.1Hz), 7.89(1H, d, J=7.2Hz), 7.91–7.97(2H, m), 8.42(1H, br-d, J=7.2Hz), 8.49(1H, s), 8.88(1H, d, J=7.2Hz), 10.50–10.57(1H, br-s). | — |

TABLE 2-continued

| Compound No. | Chemical Formula | NMR | m.p. (° C.) |
|---|---|---|---|
| B-140 | | — | — |
| B-141 | | — | — |
| B-142 | | 1H-NMR(d6-DMSO)δ: 0.80–2.00(11H, m), 2.91(2H, t, J=6.0Hz), 3.28(8H, m), 5.76(1H, br), 6.68(2H, d, J=9.0Hz), 7.06(2H, d, J=9.3Hz), 7.51(1H, d, J=7.2Hz), 7.75(2H, d, J=9.3Hz), 7.97(2H, d, J=9.0Hz), 8.70(1H, s), 8.87(2H, br), 9.23(1H, s), 10.37(1H, s), J=7.2Hz). | — |

TABLE 2-continued
| Chemical Formula | Compound No. | NMR | m.p. (° C.) |
|---|---|---|---|
| 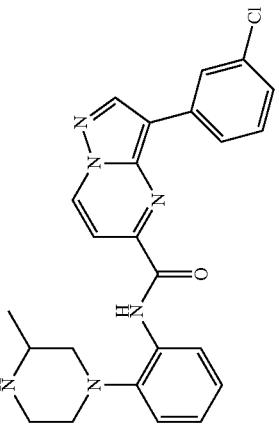 | B-143 | — | — |
| 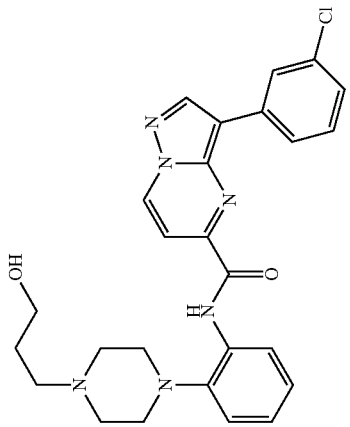 | B-144 | — | — |
| 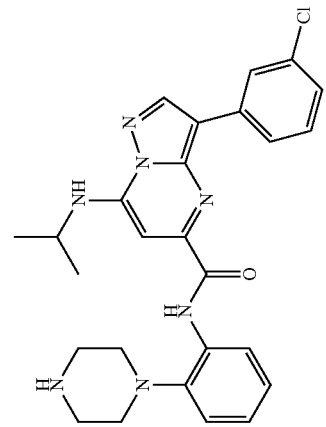 | B-145 | — | — |

TABLE 2-continued

| Chemical Formula | Compound No. | NMR | m.p. (° C.) |
|---|---|---|---|
| (structure with 3-chlorophenyl pyrazolopyridine carboxamide, piperidine, and 1,3-dihydroxypropan-2-ylamino group) | B-146 | 1H-NMR(CDCl3)δ: 1.24–1.41(2H, m), 1.74–1.86(2H, m), 2.40–2.52(1H, m), 2.60–2.73(3H, m), 3.02–3.13(2H, m), 3.42(1H, dd, J=10.7, 4.8Hz), 3.53(1H, dd, J=10.7, 4.8Hz), 7.13–7.28(3H, m), 7.31–7.37(1H, m), 7.47(1H, t, J=8.1Hz), 7.90(1H, d, J=7.2Hz), 7.92–7.98(2H, m), 8.44(1H, br-d, J=7.8Hz), 8.50(1H, s), 8.89(1H, d, J=7.2Hz), 10.47–10.54(1H, br-s). | — |
| (structure with 3-chlorophenyl pyrazolopyridine carboxamide, piperazine, and propyl-NHSO2Me group) | B-147 | 1H-NMR(d6-DMSO)δ: 1.40(2H, m), 1.78(2H, t, J=6.9Hz), 2.30(4H, br), 2.78–2.87(6H, m), 2.85(3H, s), 6.89(1H, t, J=5.4Hz), 7.15–7.30(3H, m), 7.37–7.42(1H, m), 7.57(1H, t, J=8.1Hz), 7.75(1H, d, J=7.2Hz), 8.06–8.11(2H, m), 8.29–8.32(1H, m), 8.93(1H, s), 9.42(1H, d, J=7.2Hz), 10.40(1H, br-s). | — |

TABLE 2-continued

| Compound No. | Chemical Formula | NMR | m.p. (° C.) |
|---|---|---|---|
| B-148 | | — | — |
| B-149 | | — | — |
| B-150 | | — | — |

TABLE 2-continued

| Compound No. | Chemical Formula | NMR | m.p. (° C.) |
|---|---|---|---|
| B-151 | | — | — |
| B-152 | | — | — |
| B-153 | | — | — |

TABLE 2-continued
| Compound No. | Chemical Formula | NMR | m.p. (° C.) |
|---|---|---|---|
| B-154 | 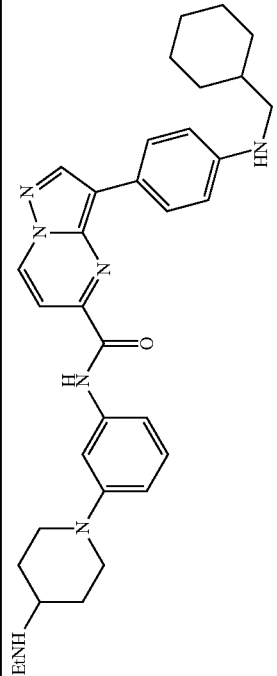 | — | — |
| B-155 | 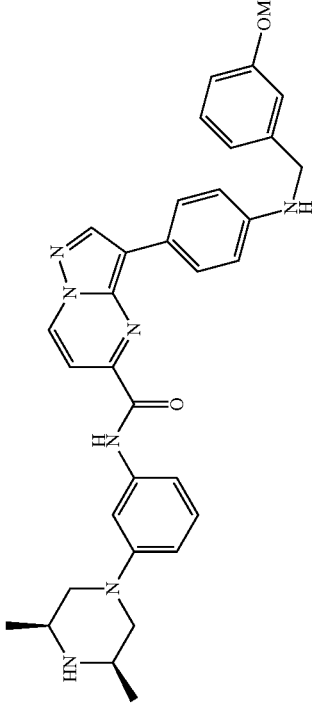 | — | — |
| B-156 | 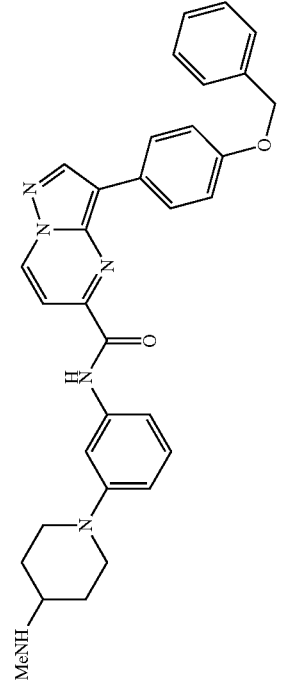 | — | — |

TABLE 2-continued

| Compound No. | Chemical Formula | NMR | m.p. (° C.) |
|---|---|---|---|
| B-157 | 3-(3-chlorophenyl)-N-(2-(4-phenylpiperazin-1-yl)phenyl)pyrazolo[1,5-a]pyrimidine-6-carboxamide | — | — |
| B-158 | 3-(3-chlorophenyl)-N-(2-hydroxyphenyl)pyrazolo[1,5-a]pyrimidine-6-carboxamide | — | — |
| B-159 | N-(2-(4-phenylpiperazin-1-yl)phenyl)pyrazolo[1,5-a]pyrimidine-6-carboxamide | — | — |

TABLE 2-continued
| Chemical Formula | Compound No. | NMR | m.p. (° C.) |
|---|---|---|---|
| 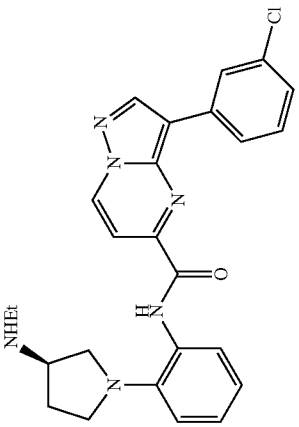 | B-160 | 1H-NMR(CDCl3)δ: 0.89(3H, d, J=7.2Hz), 1.49–1.64(1H, m), 2.03–2.17(1H, m), 2.30–2.50(2H, m), 2.86–2.96(1H, m), 3.11–3.33(4H, m), 7.11–7.21(3H, m), 7.29–7.35(1H, m), 7.44(1H, t, J=7.8Hz), 7.87–7.94(2H, m), 7.98(1H, t, J=1.8Hz), 8.33–8.41(1H, m), 8.52(1H, s), 8.88(1H, d, J=6.9Hz), 10.30–10.38(1H, br-s). | — |
| 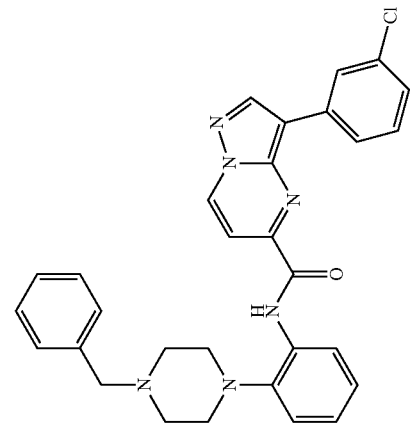 | B-161 | — | — |
| 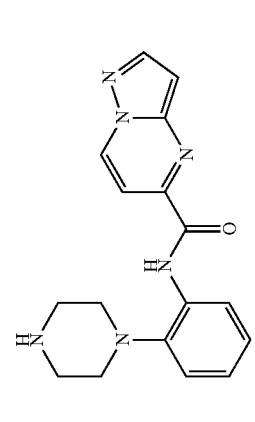 | B-162 | — | — |

TABLE 2-continued

| Compound No. | Chemical Formula | NMR | m.p. (° C.) |
|---|---|---|---|
| B-163 | | — | — |
| B-164 | (2HCl) | — | — |
| B-165 | | — | 269–271 |

TABLE 2-continued

| Chemical Formula | Compound No. | NMR | m.p. (° C.) |
|---|---|---|---|
| | B-166 | 1H-NMR(CDCl3)δ: 0.83(2H, q, J=7.2Hz), 1.08–1.35(3H, m), 1.53–1.63(2H, m), 2.33–2.40(2H, m), 2.37(3H, s), 2.55–2.67(2H, m), 2.98–3.07(2H, m), 7.13–7.32(4H, m), 7.43(1H, t, J=7.8Hz),7.87–7.97(3H, m), 8.39–8.45(1H, m), 8.49(1H, s), 8.88(1H, d, J=7.2Hz), 10.51–10.57(1H, br-s). | — |
| | B-167 | — | — |

TABLE 2-continued
| Chemical Formula | Compound No. | NMR | m.p. (° C.) |
|---|---|---|---|
| 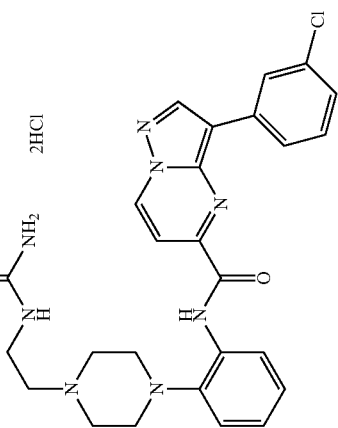 | B-168 | — | — |
| 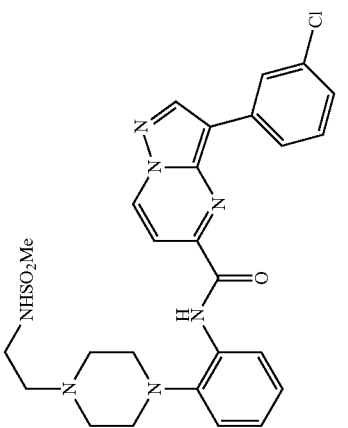 | B-169 | — | — |

TABLE 2-continued

| Chemical Formula | Compound No. | NMR | m.p. (° C.) |
|---|---|---|---|
| (structure with pyrazolo-pyridine, 3-chlorophenyl, pyrrolidine-NH-CH2CH2OH, and phenyl carboxamide) | B-170 | 1H-NMR(CDCl3)δ: 1.53–1.63(1H, m), 2.05–2.16(1H, m), 2.42–2.56(2H, m), 2.90–2.97(1H, m), 3.16–3.28(4H, m), 3.37–3.41(2H, m), 7.14–7.18(3H, m), 7.31–7.35(1H, m), 7.44(1H, t, J=7.8Hz), 7.85–7.89(1H, J=7.2Hz), 7.98(1H, t, J=1.8Hz), 8.36–8.39(1H, m), 8.51(1H, s), 8.89(1H, d, J=7.2Hz), 10.35(1H, br-s). | 125–127 |
| (structure with pyrazolo-pyridine, 3-chlorophenyl, pyrrolidine-NH-CH2CH2OH, and phenyl carboxamide) | B-171 | — | 124–125 |

TABLE 2-continued
| Chemical Formula | Compound No. | NMR | m.p. (° C.) |
|---|---|---|---|
| 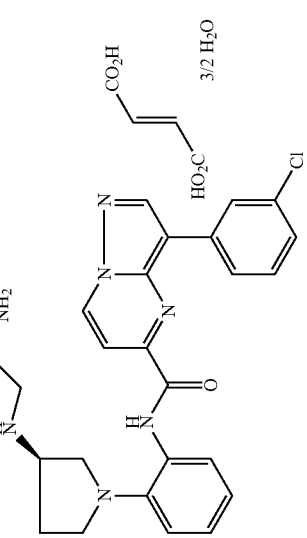 | B-172 | 1H-NMR(CDCl3)δ: 1.58–1.66(1H, m), 1.92–1.99(1H, m), 2.57–2.61(1H, m), 2.68–2.72(1H, m), 2.87–2.91(2H, m), 3.17–3.25(2H, m), 3.31–3.37(2H, m), 3.44–3.51(1H, m),6.40(2H, s), 7.01(1H, t, J=6.9Hz), 7.10–7.19(2H, m), 7.39(1H, d, J=7.8Hz), 7.53(1H, t, J=7.8Hz), 7.72(1H, dd, J=7.2, 2.1Hz), 7.92(1H, d, J=7.8Hz), 8.18(1H, d, J=1.5Hz), 8.24(1H, d, J=7.2Hz), 9.00(1H, d, J=1.8Hz), 9.40(1H, dd, J=7.2, 2.1Hz), 10.33(1H, s). | 151–152 |
| 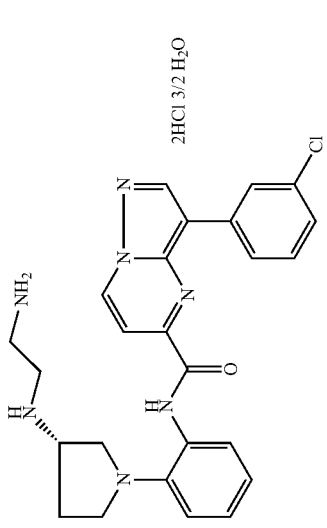 | B-173 | — | 160–162 |

TABLE 2-continued
| Chemical Formula | Compound No. | NMR | m.p. (° C.) |
|---|---|---|---|
| 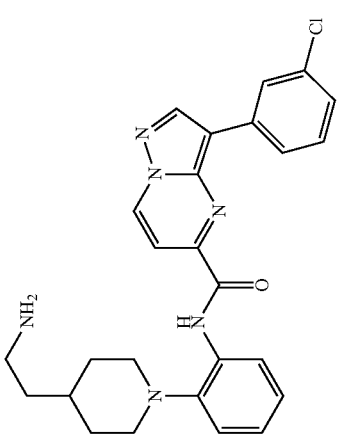 | B-174 | 1H-NMR(CDCl3)δ: 0.77(2H, q, J=7.2Hz), 1.07–1.37(3H, m), 1.50–1.61(2H, m), 2.48(2H, t, J=7.4Hz), 2.55–2.66(2H, m), 2.98–3.07(2H, m), 7.13–7.33(4H, m), 7.43(1H, t, J=7.8Hz), 7.83–7.96(3H, m), 8.40–8.45(1H, m), 8.49(1H, s), 8.88(1H, d, J=7.2Hz), 10.51–10.57(1H, br-s). | — |
| 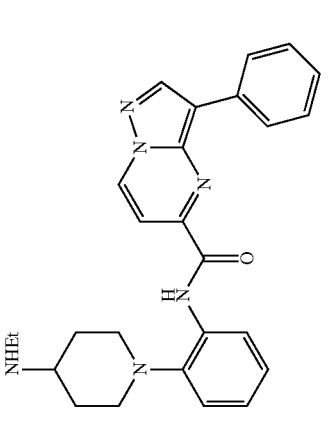 | B-175 | — | — |
| 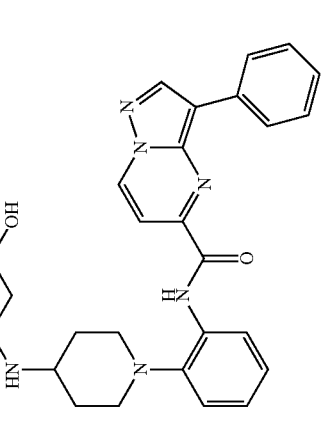 | B-176 | — | — |

TABLE 2-continued

| Compound No. | Chemical Formula | NMR | m.p. (° C.) |
|---|---|---|---|
| B-177 | (structure with HCl salt) | — | — |
| B-178 | (structure) | 1H-NMR(CDCl3)δ: 0.80–0.97(1H, m), 1.23–1.65(4H, m), 2.28–2.58(4H, m), 2.95–3.16(2H, m), 7.10–7.27(3H, m), 7.30–7.36(1H, m), 7.40–7.48(1H, m), 7.82–7.87(2H, m), 7.91(1H, d, J=7.2Hz), 8.44(1H, s), 8.47–8.53(1H, m), 8.88(1H, d,J=7.2Hz), 10.47–10.54(1H, br-s). | — |
| B-179 | (structure) | — | — |

TABLE 2-continued
| Compound No. | NMR | m.p. (° C.) |
|---|---|---|
| B-180 | — | — |
| B-181 | — | — |
Chemical Formula:
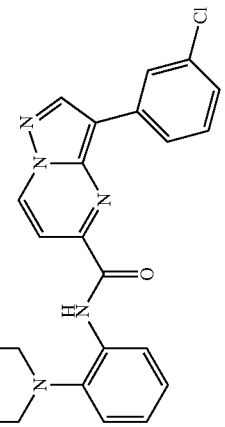
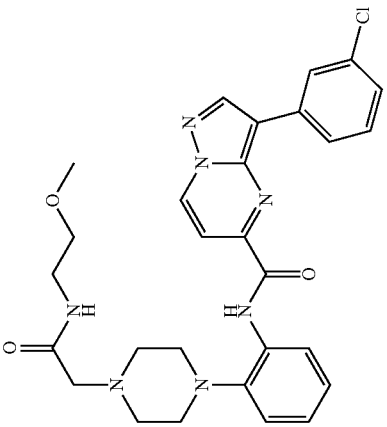

TABLE 2-continued
| Chemical Formula | Compound No. | NMR | m.p. (° C.) |
|---|---|---|---|
| 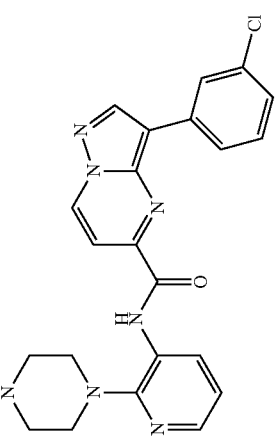 | B-182 | — | — |
| 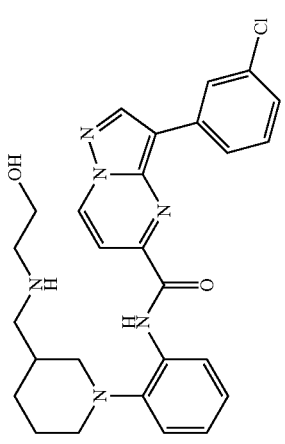 | B-183 | — | — |
| 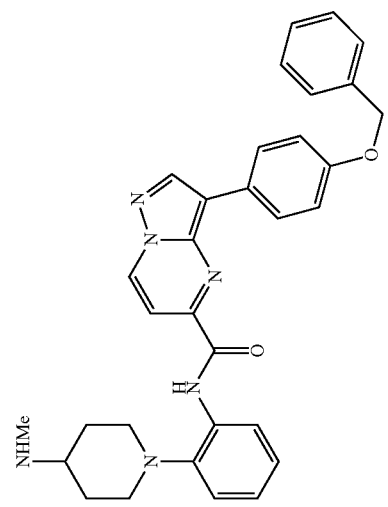 | B-184 | 1H-NMR(CDCl3)δ: 1.17–1.35(2H, m), 1.79–1.91(2H, m), 2.19–2.32(1H, m), 2.25(3H, s), 2.58–2.71(2H, m), 3.00–3.12(2H, m), 5.13(2H, s), 7.11–7.23(5H, m), 7.31–7.51(5H, m), 7.85(1H, d, J=7.2Hz), 7.90(2H, dt, J=9.0, 2.1Hz), 8.41(1H, s),8.44(1H, br-d, J=7.5Hz), 8.84(1H, d, J=7.2Hz), 10.44–10.51(1H, br-s). | — |

TABLE 2-continued

| Chemical Formula | Compound No. | NMR | m.p. (° C.) |
|---|---|---|---|
| | B-185 | — | — |
| | B-186 | — | — |
| | B-187 | — | — |

| Chemical Formula | Compound No. | NMR | m.p. (° C.) |
|---|---|---|---|
| (structure with NHMe-piperidine, phenylamide, pyrazolopyridine, phenyl-NH-benzyl) | B-188 | 1H-NMR(CDCl3)δ: 1.21–1.38(2H, m), 1.80–1.92(2H, m), 2.21–2.38(1H, m), 2.26(3H, s), 2.57–2.70(2H, m), 3.01–3.11(2H, m), 4.39(2H, s), 6.80(2H, dt, J=8.7, 2.1Hz), 7.10–7.45(8H, m), 7.77(2H, dt, J=8.7, 2.1Hz), 7.81(1H, d, J=7.2Hz), 8.37(1H,s), 8.44(1H, br-d, J=7.5Hz), 8.81(1H, d, J=7.2Hz), 10.44–10.51(1H, br-s). | |
| (structure with NHMe-piperidine, phenylamide, pyrazolopyridine, phenyl-CH2CH2-phenyl) | B-189 | 1H-NMR(CDCl3)δ: 1.16–1.35(2H, m), 1.79–1.91(2H, m), 2.16–2.33(1H, m), 2.21(3H, s), 2.58–2.71(2H, m), 2.94–3.13(6H, m), 7.11–7.40(10H, m), 7.87(1H, d, J=7.5Hz), 7.91(2H, br-d, J=8.4Hz), 8.44(1H, br-d, J=7.5Hz), 8.47(1H, s), 8.86(1H,d, J=7.5Hz), 10.45–10.53(1H, br-s). | — |

TABLE 2-continued

| Chemical Formula | Compound No. | NMR | m.p. (° C.) |
|---|---|---|---|
| [structure: pyrazolopyrimidine with 3-chlorophenyl, carboxamide to 2-(4-(methylamino)piperazin-1-yl)phenyl] | B-190 | — | — |
| [structure: pyrazolopyrimidine with 4-styrylphenyl, carboxamide to 2-(4-(methylamino)piperidin-1-yl)phenyl] | B-191 | 1H-NMR(CDCl3)δ: 1.15–1.32(2H, m), 1.79–1.91(2H, m), 2.18–2.34(1H, m), 2.23(3H, s), 2.58–2.70(2H, m), 2.99–3.10(2H, m), 6.61(1H, d, J=12.2Hz), 6.67(1H, d, J=12.2Hz), 7.11–7.39(10H, m), 7.42(2H, d, J=8.4Hz), 7.87(1H, d,J=7.2Hz), 7.86(2H, dt, J=8.4, 1.8Hz), 8.41–8.47(1H, m), 8.47(1H, s), 8.85(1H, d, J=7.2Hz), 10.40–10.48(1H, br-s). | — |

TABLE 2-continued

| Chemical Formula | Compound No. | NMR | m.p. (° C.) |
|---|---|---|---|
| (structure with NHMe-piperidine, pyrazolopyridine carboxamide, and stilbene) | B-192 | 1H-NMR(CDCl3)δ: 1.19–1.36(2H, m), 1.81–1.92(2H, m), 2.14–2.32(1H, m), 2.18(3H, s), 2.59–2.71(2H, m), 3.02–3.14(2H, m), 7.12–7.32(7H, m), 7.34–7.42(1H, m), 7.51–7.58(2H, m), 7.69(2H, d, J=8.4Hz), 7.89(1H, d, J=7.5Hz), 7.98(2H,d, J=8.4Hz), 8.45–8.50(1H, m), 8.44(1H, s), 8.87(1H, d, J=7.5Hz), 10.48–10.54(1H, br-s). | — |
| (structure with isopropyl-piperazine, pyrazolopyridine carboxamide, and 3-chlorophenyl) | B-193 | 1H-NMR(CDCl3)δ: 0.74(6H, d, J=6.6Hz), 2.14(1H, quint, J=6.6Hz), 2.36–2.54(1H, br), 2.92(4H, br-t, J=4.8Hz), 7.13–7.33(4H, m), 7.41(1H, t, J=7.8Hz), 7.85–7.93(2H, m), 8.01(1H, t, J=1.8Hz), 8.40–8.46(1H, m), 8.51(1H, s), 8.88(1H,d, J=7.2Hz), 10.42–10.59(1H, br-s). | — |

TABLE 2-continued

| Compound No. | Chemical Formula | NMR | m.p. (° C.) |
|---|---|---|---|
| B-194 | | — | — |
| B-195 | | 1H-NMR(CDCl3)δ: 0.91(6H, d, J=6.0Hz), 1.12–1.30(2H, m), 1.79–1.91(2H, m), 2.39–2.54(1H, m), 2.60–2.82(3H, m), 3.02–3.12(2H, m), 7.13–7.36(4H, m), 7.48(1H, t, J=7.8Hz), 7.88–7.99(3H, m), 8.42–8.47(1H, m), 8.49(1H, s), 8.89(1H, d, J=7.2Hz),10.48–10.54(1H, br-s). | — |
| B-196 | | 1H-NMR(CDCl3)δ: 1.57–1.66(1H, m), 1.70–1.87(2H, m), 2.02–2.13(1H, m), 2.54–2.61(2H, m), 2.64–2.70(1H, m), 2.81–2.89(1H, m), 3.41–3.50(2H, m), 7.13–7.23(2H, m), 7.27–7.35(2H, m), 7.42–7.47(1H, m), 7.80(1H, t, J=1.8Hz),7.89(1H, d, J=7.5Hz), 7.81–7.93(1H, s), 8.46(1H, s), 8.51(1H, dd, J=7.5, 1.8Hz), 8.87(1H, d, J=7.2Hz), 10.66(1H, s). | 168–170 |

TABLE 2-continued

| Chemical Formula | Compound No. | NMR | m.p. (° C.) |
|---|---|---|---|
| [structure with pyrazolopyrimidine, phenyl, piperazine, amide] | B-197 | — | — |
| [structure with pyrazolopyrimidine, chlorophenyl, pyrrolidine, ethanol]·HCl CH$_3$OH | B-198 | 1H-NMR(CDCl3)δ: 1.72–1.84(2H, m), 2.15–2.24(1H, m), 2.78–2.95(5H, m), 3.52–3.63(3H, m), 3.91–4.00(1H, m), 5.14–5.20(1H, m), 7.15–7.25(2H, m), 7.40(1H, d, J=7.2Hz), 7.58(1H, t, J=7.8Hz), 7.74(1H, d, J=7.2Hz), 8.10(1H, s),8.16–8.22(2H, m), 8.58(1H, br-s), 8.73(1H, br-s), 8.99(1H, s), 9.42(1H, d, J=7.2Hz), 10.39(1H, s) | 118–121 |

TABLE 2-continued

| Chemical Formula | Compound No. | NMR | m.p. (° C.) |
|---|---|---|---|
| [structure] | B-199 | — | 152–155 |
| i-PrOH [structure] | B-200 | — | — |

TABLE 2-continued

| Chemical Formula | Compound No. | NMR | m.p. (° C.) |
|---|---|---|---|
| (structure with 3-chlorophenyl pyrazolopyridine, carboxamide to 2-(3-methylpiperazin-1-yl)phenyl) | B-201 | 1H-NMR(CDCl3)δ: 0.93(3H, d, J=6.0Hz), 2.39–2.48(1H, m), 2.62–2.94(6H, m), 7.11–7.28(3H, m), 7.31–7.37(1H, m), 7.43(1H, t, J=8.1Hz), 7.84–7.93(3H, m), 8.46(1H, s), 8.47–8.53(1H, m), 8.88(1H, d, J=7.5Hz), 10.54–10.62(1H, br-s). | — |
| (structure with 4-[(3-methoxybenzyl)amino]phenyl pyrazolopyridine, carboxamide to 3-(piperazin-1-yl)phenyl) | B-202 | — | — |

TABLE 2-continued

| Chemical Formula | Compound No. | NMR | m.p. (° C.) |
|---|---|---|---|
| (structure) | B-203 | — | >300 |
| (structure) | B-204 | — | — |

TABLE 2-continued
| Chemical Formula | Compound No. | NMR | m.p. (° C.) |
|---|---|---|---|
| 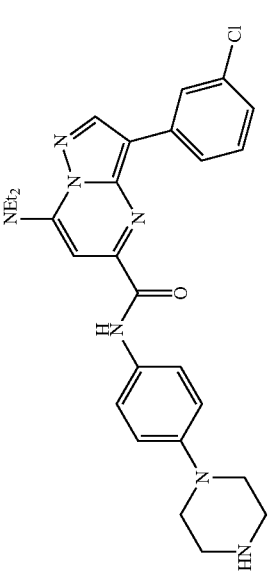 | B-205 | — | — |
| 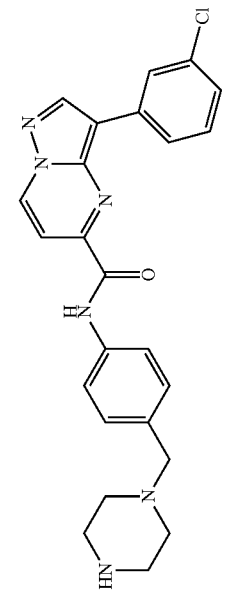 | B-206 | — | — |
| 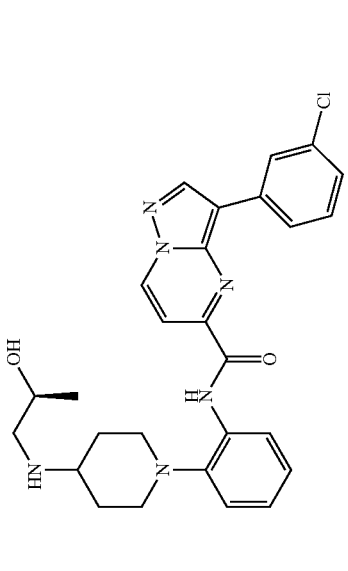 | B-207 | 1H-NMR(CDCl3)δ: 1.09(3H, d, J=6.3Hz), 1.15–1.32(2H, m), 1.75–1.87(2H, m), 2.07(1H, dd, J=11.7, 9.6Hz), 2.26–2.39(1H, m), 2.55–2.70(3H, m), 3.00–3.11(2H, m), 3.46–3.59(1H, m), 7.13–7.27(3H, m), 7.30–7.36(1H, m), 7.46(1H, t,J=7.8Hz), 7.87–7.95(3H, m), 8.44(1H, br-d, J=7.5Hz), 8.48(1H, s), 8.89(1H, d, J=7.5Hz), 10.49–10.56(1H, br-s). | — |

TABLE 2-continued

| Chemical Formula | Compound No. | NMR | m.p. (°C.) |
|---|---|---|---|
| (structure) | B-208 | 1H-NMR(CDCl3)δ: 0.91(3H, d, J=6.3Hz), 1.20–1.37(2H, m), 1.71–1.86(2H, m), 2.37–2.50(1H, m), 2.60–2.72(3H, m), 2.99–3.12(3H, m), 3.41(1H, dd, J=10.2, 4.2Hz), 7.13–7.27(3H, m), 7.30–7.36(1H, m), 7.47(1H, t, J=8.1Hz),7.88–7.97(3H, m), 8.44(1H, br-d, J=7.5Hz), 8.49(1H, s), 8.89(1H, d, J=7.2Hz), 10.47–10.54(1H, br-s). | — |
| (structure) | B-209 | — | — |
| (structure) | B-210 | — | — |

TABLE 2-continued
| Chemical Formula | Compound No. | NMR | m.p. (° C.) |
|---|---|---|---|
|  | B-211 | — | — |
|  | B-212 | — | — |
|  0.3 THF | B-213 | — | 507–509 |

TABLE 2-continued

| Chemical Formula | Compound No. | NMR | m.p. (° C.) |
|---|---|---|---|
| (structure) | B-214 | 1H-NMR(CDCl3)δ: 0.91(3H, d, J=6.3Hz), 1.20–1.37(2H, m), 1.71–1.86(2H, m), 2.37–2.50(1H, m), 2.60–2.72(3H, m), 2.99–3.12(3H, m), 3.41(1H, dd, J=10.2, 4.2Hz), 7.13–7.27(3H, m), 7.30–7.36(1H, m), 7.47(1H, t, J=8.1Hz), 7.88–7.97(3H, m), 8.44(1H, br-d, J=7.5Hz), 8.49(1H, s), 8.89(1H, d, J=7.2Hz), 10.47–10.54(1H, br-s). | — |
| (structure) | B-215 | — | 97–98 |
| (structure) | B-216 | — | — |

TABLE 2-continued

| Chemical Formula | Compound No. | NMR | m.p. (° C.) |
|---|---|---|---|
| (structure shown) | B-217 | 1H-NMR(CDCl3)δ: 1.15(3H, t, J=7.2Hz), 1.53(2H, m), 2.03(2H, m), 2.65(1H, m), 2.73(2H, q, J=7.2Hz), 2.84(2H, m), 3.76(2H, m), 5.16(1H, s), 6.78(1H, m), 6.96(1H, m), 7.15(2H, d, J=9.0Hz), 7.27(1H, t, J=8.1Hz), 7.33–7.45(3H, m), 7.49(2H, m), 7.63(1H, t, J=2.1Hz), 7.78(1H, d, J=7.5Hz), 7.92(2H, d, J=9.0Hz), 8.46(1H, s), 8.83(1H, d, J=7.5Hz), 9.63(1H, s). | — |
| (structure shown) 3/10 | B-218 | — | 183–184 |

TABLE 2-continued
| Chemical Formula | Compound No. | NMR | m.p. (° C.) |
|---|---|---|---|
| 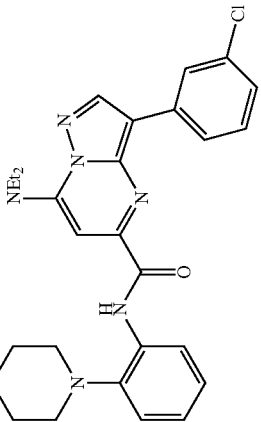 | B-219 | — | — |
| 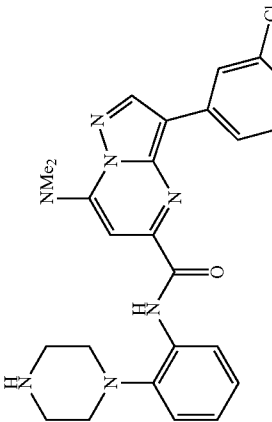 | B-220 | — | — |
| 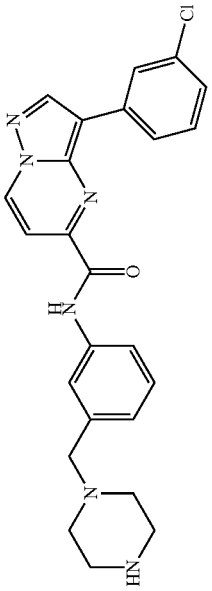 | B-221 | — | — |

TABLE 2-continued

| Chemical Formula | Compound No. | NMR | m.p. (° C.) |
|---|---|---|---|
|  | B-222 | — | — |
|  | B-223 | — | — |
|  | B-224 | — | — |

TABLE 2-continued
| Compound No. | Chemical Formula | NMR | m.p. (° C.) |
|---|---|---|---|
| B-225 | 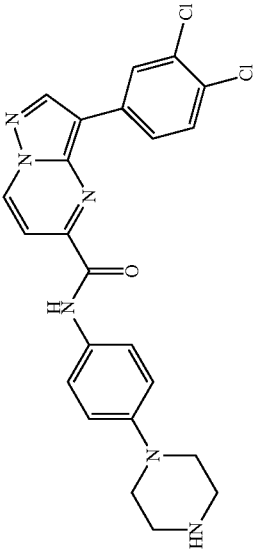 | — | — |
| B-226 | 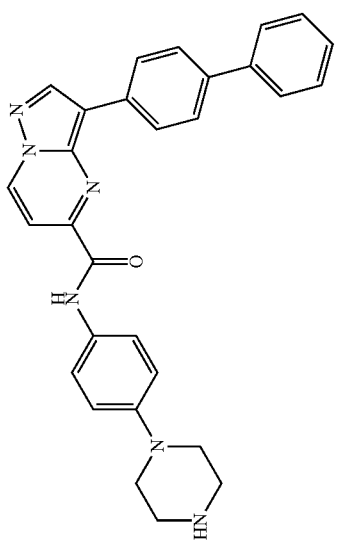 | — | — |
| B-227 | 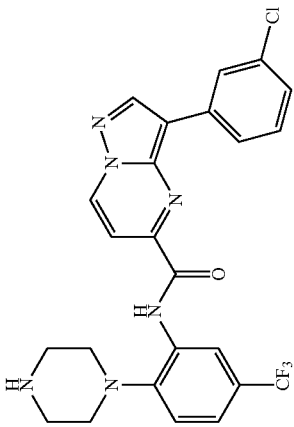 | 1H-NMR(d6-DMSO)δ: 2.78(4H, br), 2.82(4H, br), 7.38–7.41(1H, m), 7.46(1H, d, J=8.7Hz), 7.54–7.59(2H, m), 7.77(1H, d, J=7.2Hz), 8.13(1H, s), 8.25(1H, d, J=7.8Hz), 8.68(1H, s), 9.01(1H, s), 9.43(1H, d, J=7.2Hz), 10.31(1H, br-s). | — |

TABLE 2-continued

| Chemical Formula | Compound No. | NMR | m.p. (° C.) |
|---|---|---|---|
| (structure) | B-228 | — | — |
| (structure) | B-229 | — | — |
| (structure) | B-230 | — | — |

TABLE 2-continued

| Chemical Formula | Compound No. | NMR | m.p. (°C.) |
|---|---|---|---|
| (structure) | B-231 | 1H-NMR(CDCl3)δ: 1.09(3H, d, J=6.3Hz), 1.15–1.32(2H, m), 1.75–1.87(2H, m), 2.07(1H, dd, J=11.7, 9.6Hz), 2.26–2.39(1H, m), 2.55–2.70(3H, m), 3.00–3.11(2H, m), 3.46–3.59(1H, m),7.13–7.27(3H, m), 7.30–7.36(1H, m), 7.46(1H, t, J=7.8Hz), 7.87–7.95(3H, m), 8.44(1H, br-d, J=7.5Hz), 8.48(1H, s), 8.89(1H, d, J=7.5Hz), 10.49–10.56(1H, br-s). | — |
| (structure) | B-232 | — | — |
| (structure) | B-233 | — | — |

TABLE 2-continued

| Compound No. | Chemical Formula | NMR | m.p. (° C.) |
|---|---|---|---|
| B-234 | 3-(3-chlorophenyl)-N-[2-(4-butylaminopiperidin-1-yl)phenyl]pyrazolo[1,5-a]pyrimidine-5-carboxamide | — | — |
| B-235 | 3-(3-chlorophenyl)-N-[2-(4-pentylaminopiperidin-1-yl)phenyl]pyrazolo[1,5-a]pyrimidine-5-carboxamide | — | — |
| B-236 | 3-(3-methylphenyl)-N-[4-(piperazin-1-yl)phenyl]pyrazolo[1,5-a]pyrimidine-6-carboxamide | — | — |

TABLE 2-continued
| Chemical Formula | Compound No. | NMR | m.p. (° C.) |
|---|---|---|---|
| 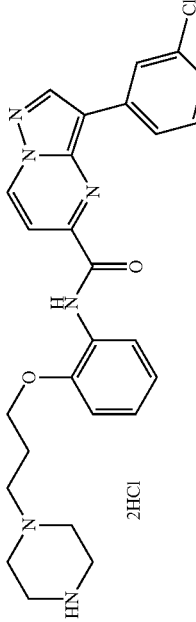 2HCl | B-237 | — | — |
| 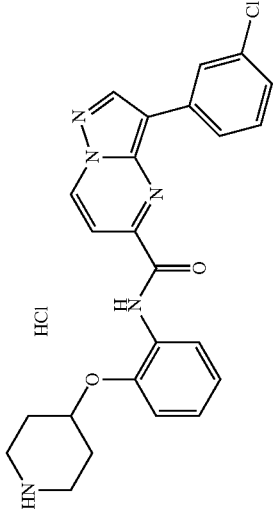 HCl | B-238 | 1H-NMR(d6-DMSO+CD3OD) δ: 1.78–1.94(2H, m), 2.07–2.20(2H, m), 3.06–3.16(2H, m), 3.23–3.34(2H, m), 4.62–4.72(1H, m), 7.10(2H, d, J=8.7Hz), 7.37(1H, d, J=9.0Hz), 7.54(1H, t, J=7.5Hz), 7.67(1H, d, J=7.5Hz), 7.77(2H, d, J=8.7Hz), 8.27(1H, d, J=9.0Hz), 8.35(1H, s), 8.96(1H, s), 9.31(1H, d, J=7.5Hz). | — |
| 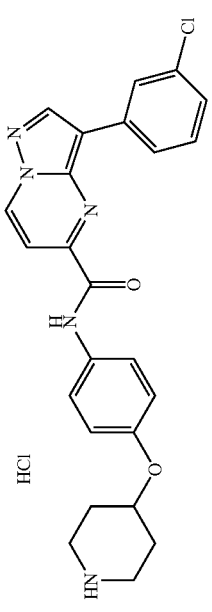 HCl | B-239 | 1H-NMR(d6-DMSO)δ: 1.71–1.90(2H, m), 2.07–2.19(2H, m), 2.77–2.87(2H, m), 3.01–3.10(2H, m), 4.76–4.85(1H, m), 7.08(1H, t, J=7.8Hz), 7.20(1H, t, J=7.8Hz), 7.26(1H, d, J=7.8Hz),7.40(1H, d, J=7.8Hz), 7.59(1H, t, J=7.8Hz), 7.76(1H, d, J=7.2Hz), 8.11(1H, s), 8.19(1H, d, J=7.8Hz), 8.31(1H, d, J=7.8Hz), 8.60(2H, br), 9.01(1H, s), 9.44(1H, d, J=7.2Hz), 10.18(1H, br-s). | |

TABLE 2-continued

| Chemical Formula | Compound No. | NMR | m.p. (° C.) |
|---|---|---|---|
| (structure) | B-240 | 1H-NMR(CDCl3)δ: 2.77–2.90(8H, m), 7.14–7.30(3H, m), 7.34(1H, t, J=1.8Hz), 7.85–7.94(3H, m), 8.42–8.48(1H, m), 8.48(1H, s), 8.90(1H, d, J=7.2Hz), 10.52–10.60(1H, br-s). | — |
| (structure) | B-241 | 1H-NMR(CDCl3)δ: 3.02–3.21(8H, m), 7.00(2H, d, J=8.7Hz), 7.34(1H, t, J=1.8Hz), 7.71(2H, d, J=8.7Hz), 7.89(1H, d, J=7.2Hz), 7.99(2H, d, J=1.8Hz), 8.54(1H, s), 8.88(1H, d, J=7.2Hz), 9.59–9.66(1H, br-s). | — |
| (structure) | B-242 | 1H-NMR(CDCl3)δ: 2.84(8H, s), 4.18–4.32(1H, br), 4.35–4.42(2H, br-s), 6.62–6.69(1H, m), 7.06–7.41(11H, m), 7.85(1H, d, J=7.2Hz), 8.39(1H, s), 8.50(1H, br-d, J=7.2Hz), 8.84(1H, d, J=7.2Hz),10.54–10.62(1H, br-s). | — |

TABLE 2-continued
| Chemical Formula | Compound No. | NMR | m.p. (° C.) |
|---|---|---|---|
| 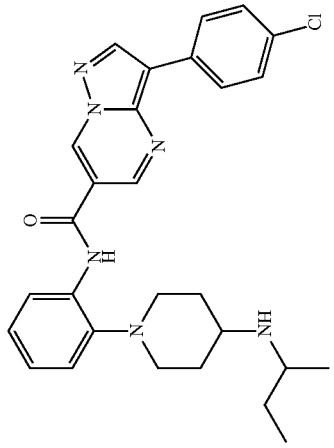 | B-243 | — | 229–231 |
| 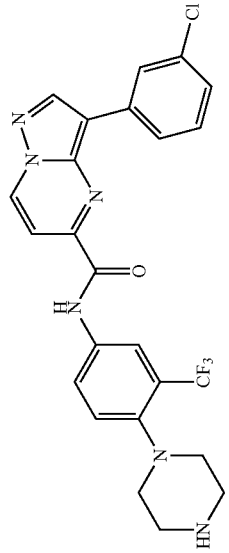 | B-244 | 1H-NMR(d6-DMSO)δ: 2.79(4H, br), 2.81(4H, br), 7.35(1H, d, J=8.1Hz), 7.52(1H, t, J=8.1Hz), 7.59(1H, d, J=8.4Hz), 7.65(1H, d, J=6.9Hz), 8.11(1H, d, J=8.4Hz), 8.25(1H, s), 8.32(1H, d, J=8.1Hz), 8.36(1H, s),9.03(1H, s), 9.38(1H, d, J=6.9Hz), 10.89(1H, br-s). | — |
| 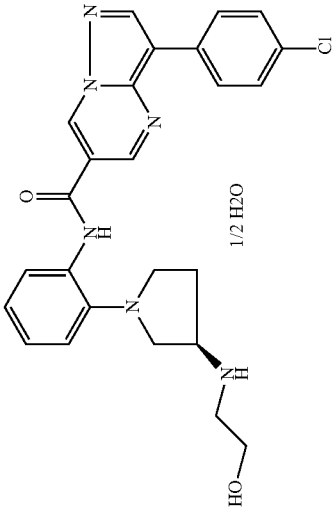 | B-245 | — | 164–165 |

TABLE 2-continued

| Chemical Formula | Compound No. | NMR | m.p. (° C.) |
|---|---|---|---|
| (structure) | B-246 | 1H-NMR(CDCl3)δ: 0.99(3H, t, J=7.2Hz), 1.14–1.30(2H, m), 1.80–1.91(2H, m), 2.31–2.49(1H, m), 2.45(2H, q, J=7.2Hz), 2.60–2.71(2H, m), 3.02–3.11(2H, m), 7.11–7.28(3H, m), 7.31–7.37(1H, m), 7.45–7.52(1H, m), 7.88–7.96(3H, m), 8.43–8.48(1H, m), 8.49(1H, s), 8.89(1H, d, J=7.2Hz), 10.49–10.55(1H, br). | — |
| (structure) | B-247 | — | — |
| (structure) | B-248 | — | — |

TABLE 2-continued

| Chemical Formula | Compound No. | NMR | m.p. (° C.) |
|---|---|---|---|
| [structure with 3-chlorophenyl pyrazolopyridine, urea linker, piperazinyl-phenyl] | B-249 | — | 120–140 |
| [structure with 4-fluorophenyl pyrazolopyrimidine carboxamide, piperazinyl-phenyl] · 4/5 tetrahydrofuran | B-250 | — | — |
| [structure with 3-chlorophenyl pyrazolopyridine carboxamide, propylamino-piperidinyl-phenyl] | B-251 | 1H-NMR(CDCl3)δ: 0.85(3H, t, J=7.4Hz), 1.17–1.44(4H, m), 1.81–1.92(2H, m), 2.33–2.42(3H, m), 2.60–2.72(2H, m), 3.02–3.12(2H, m), 7.13–7.35(4H, m), 7.48(1H, t, J=7.8Hz), 7.88–7.97(3H, m), 8.42–8.47(1H, m), 8.49(1H, s), 8.88(1H, d, J=7.2Hz), 10.47–10.53(1H, br-s). | — |

TABLE 2-continued
| Chemical Formula | Compound No. | NMR | m.p. (° C.) |
|---|---|---|---|
| 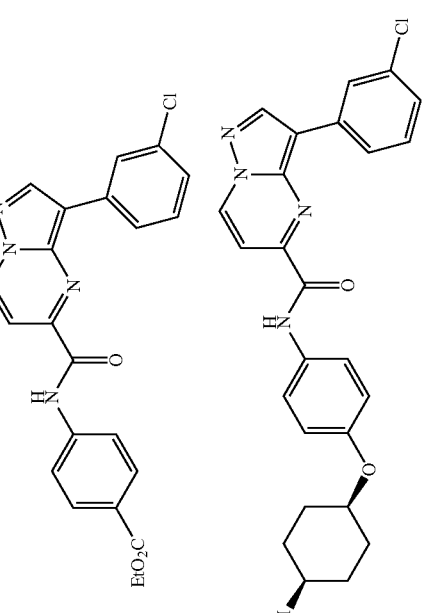 | B-252 | — | — |
| 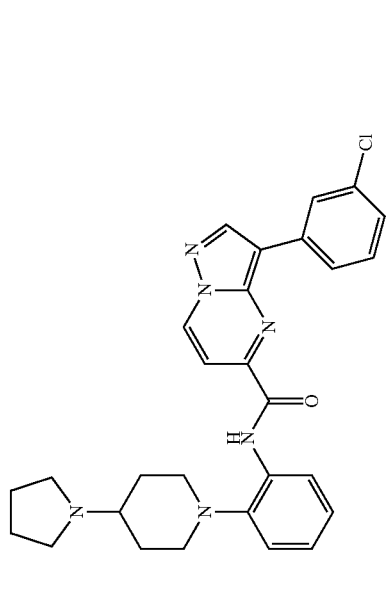 | B-253 | — | — |
| 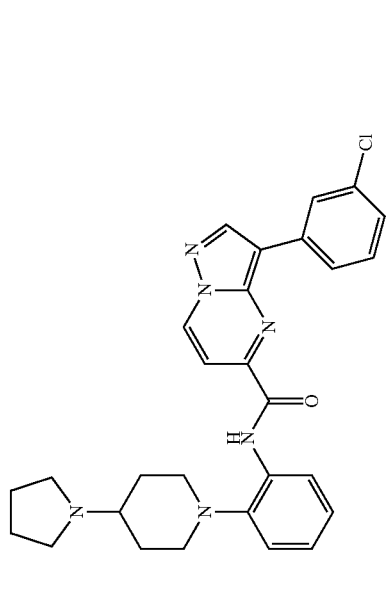 | B-254 | — | — |

TABLE 2-continued

| Compound No. | Chemical Formula | NMR | m.p. (° C.) |
|---|---|---|---|
| B-255 | (3-(3-chlorophenyl)pyrazolo[1,5-a]pyrimidine-5-carboxylic acid (3-ethoxycarbonylphenyl)amide) | — | — |
| B-256 | (3-(3-chlorophenyl)pyrazolo[1,5-a]pyrimidine-5-carboxylic acid (2-(4-oxopiperidin-1-yl)phenyl)amide) | — | — |
| B-257 | (3-(3-aminophenyl)pyrazolo[1,5-a]pyrimidine-5-carboxylic acid (4-(piperazin-1-yl)phenyl)amide) | — | — |

TABLE 2-continued

| Compound No. | Chemical Formula | NMR | m.p. (° C.) |
|---|---|---|---|
| B-258 | 3-(3-chlorophenyl)pyrazolo[1,5-a]pyrimidine-5-carboxamide with N-[2-(4-propylpiperazin-1-yl)phenyl] | — | — |
| B-259 | 3-(3-chlorophenyl)pyrazolo[1,5-a]pyrimidine-5-carboxamide with N-(4-cyanophenyl) | 1H-NMR(CDCl3)δ: 7.36(1H, ddd, J=7.2, 2.1, 1.2Hz), 7.47(1H, t, J=7.8Hz), 7.74(2H, d, J=9.0Hz), 7.80(1H, dt, J=7.8, 1.2Hz), 7.85(1H, d, J=7.2Hz), 7.92(2H, d, J=9.0Hz), 8.17(1H, t, J=2.1Hz), 8.92(1H, d, J=7.2Hz), 9.93(1H, s). | — |
| B-260 | 3-(3-chlorophenyl)-7-(NEt2)pyrazolo[1,5-a]pyrimidine-5-carboxamide with N-[2-(piperazin-1-yl)-5-(trifluoromethyl)phenyl] | — | — |

TABLE 2-continued

| Compound No. | Chemical Formula | NMR | m.p. (° C.) |
|---|---|---|---|
| B-261 | (structure) | — | — |
| B-262 | (structure) | 1H-NMR(d6-DMSO)δ: 3.26(4H, m), 4.40(2H, d, J=5.7Hz), 6.29(1H, t, J=6.0Hz), 6.55(1H, dd, J=8.4, 1.5Hz), 7.01(2H, d, J=9.0Hz), 7.15(1H, t, J=7.8Hz), 7.22(1H, d, J=6.9Hz), 7.27–7.41(4H, m), 7.59(1H, d, J=7.2Hz), 7.65(1H, m), 7.76(2H, d, J=9.0Hz), 8.72(2H, br), 8.77(1H, s), 9.31(1H, d, J=7.2Hz), 10.41(1H, s). | — |
| B-263 | (structure) | — | 185–187 |

TABLE 2-continued

| Compound No. | Chemical Formula | NMR | m.p. (° C.) |
|---|---|---|---|
| B-264 | (3-(piperazin-1-yl)phenyl)amide of 3-(3-benzyloxyphenyl)pyrazolo[1,5-a]pyrimidine-6-carboxylic acid | — | — |
| B-265 | (4-(4-methylpiperazin-1-ylamino)phenyl)amide of 3-(3-chlorophenyl)pyrazolo[1,5-a]pyrimidine-5-carboxylic acid | — | — |
| B-266 | (4-(piperazin-1-yl)phenyl)amide of 3-(3-benzyloxyphenyl)pyrazolo[1,5-a]pyrimidine-6-carboxylic acid | — | — |
| B-267 | (4-(2-morpholinoethoxy)-2-(piperazin-1-yl)phenyl)amide of 3-(3-chlorophenyl)pyrazolo[1,5-a]pyrimidine-5-carboxylic acid · 1.9HCl | — | — |

TABLE 2-continued

| Compound No. | NMR | m.p. (° C.) |
|---|---|---|
| B-268 | — | — |
| B-269 | — | — |
| B-270 | — | — |

TABLE 2-continued

| Compound No. | Chemical Formula | NMR | m.p. (° C.) |
|---|---|---|---|
| B-271 | (structure) | — | — |
| B-272 | (structure) | — | — |
| B-273 | (structure) | — | — |

TABLE 2-continued

| Compound No. | NMR | m.p. (° C.) |
|---|---|---|
| B-274 | — | — |
| B-275 | — | — |
| B-276 | 1H-NMR(d6-DMSO)δ: 2.79(4H, br), 3.39(4H, br), 6.88(1H, d, J=8.7Hz), 7.35(1H, d, J=8.1Hz), 7.52(1H, t, J=8.1Hz), 7.64(1H, d, J=7.2Hz), 7.98(1H, d, J=8.7Hz), 8.33(1H, s), 8.35(1H, d, J=8.1Hz), 8.55(1H,s), 9.02(1H, s), 9.35(1H, d, J=7.2Hz), 10.57(1H, br-s). | — |

TABLE 2-continued
| Compound No. | NMR | m.p. (° C.) |
|---|---|---|
| B-277 | — | 236-238 |
| B-278 | — | — |
| B-279 | — | — |
Chemical Formula
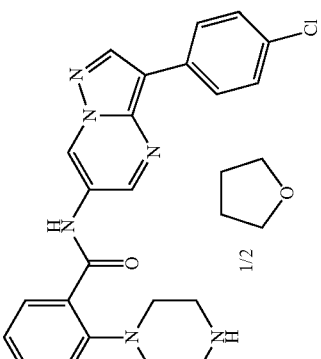
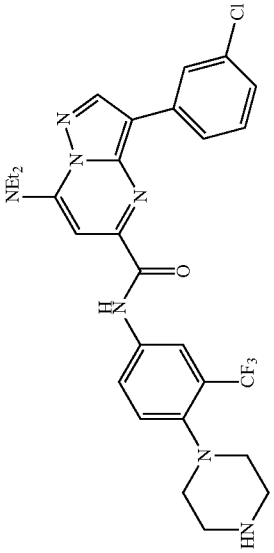
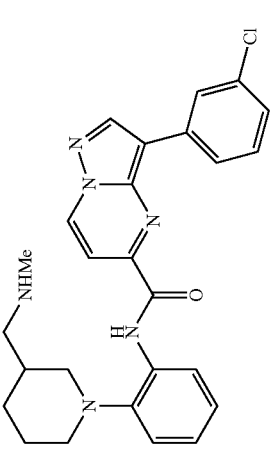

TABLE 2-continued
| Compound No. | Chemical Formula | NMR | m.p. (° C.) |
|---|---|---|---|
| B-280 | 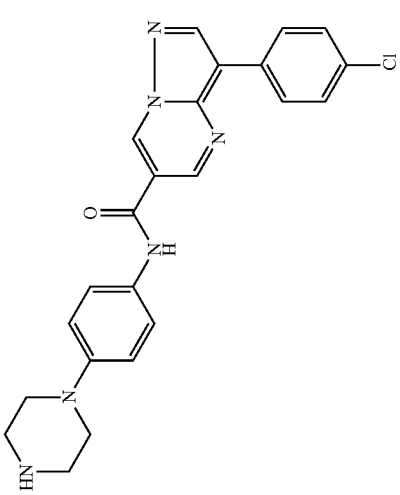 | — | 267–269(d) |
| B-281 | 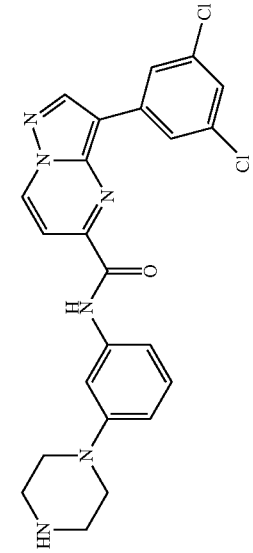 | — | — |
| B-282 | | — | — |

TABLE 2-continued
| Compound No. | Chemical Formula | NMR | m.p. (° C.) |
|---|---|---|---|
| B-283 | 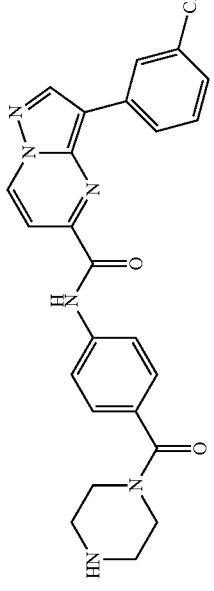 | — | — |
| B-284 | 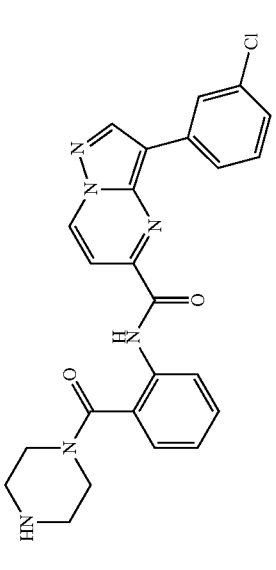 | — | — |
| B-285 | 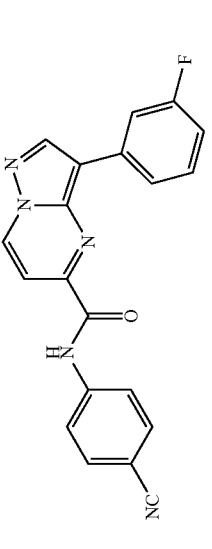 | — | — |
| B-286 | 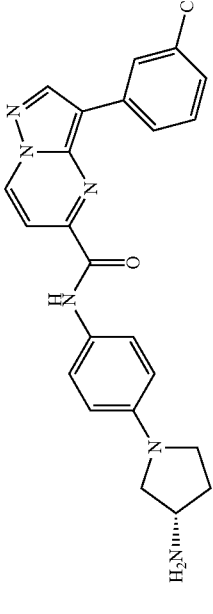 | 1H-NMR(CDCl3)δ: 1.35(2H, br), 1.83(1H, m), 2.25(1H, m), 3.06(1H, dd, J=9.3, 4.5Hz), 3.37(1H, m), 3.49-3.58(2H, m), 3.74(1H, m), 6.60(2H, d, J=9.0Hz), 7.32(1H, m), 7.44(1H, t, J=7.8Hz), 7.65(2H, d, J=9.0Hz), 7.85(1H, m), 7.86(1H, d, J=7.5Hz), 8.16(1H, t, J=1.8Hz), 8.53(1H, s), 8.86(1H, d, J=7.5Hz), 9.57(1H, s). | — |

TABLE 2-continued

| Chemical Formula | Compound No. | NMR | m.p. (° C.) |
|---|---|---|---|
|  | B-287 | — | — |
|  | B-288 | — | — |
|  | B-289 | — | — |

TABLE 2-continued

| Chemical Formula | Compound No. | NMR | m.p. (° C.) |
|---|---|---|---|
| (structure) | B-290 | 1H-NMR(CDCl3)δ: 2.42(4H, br), 2.90(4H, t, J=4.8Hz), 3.50(2H, s), 4.24(1H, t, J=5.1Hz), 4.44(2H, d, J=5.1Hz), 6.81(2H, d, J=8.4Hz), 7.26–7.44(7H, m), 7.69(2H, d, J=8.4Hz), 7.75(1H, d, J=7.5Hz), 7.81(2H, d, J=8.4Hz), 8.43(1H, s), 8.80(1H, d, J=7.5Hz), 9.69(1H, s). | — |
| (structure) | B-291 | — | — |
| (structure) | B-292 | — | 190–191 |

TABLE 2-continued
| Chemical Formula | Compound No. | NMR | m.p. (° C.) |
|---|---|---|---|
| 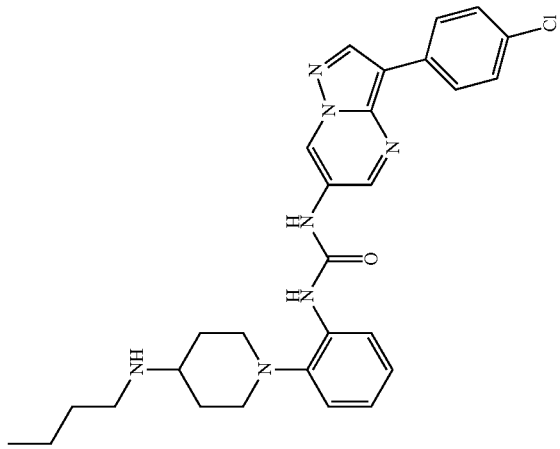 | B-293 | — | 138–143 |
| 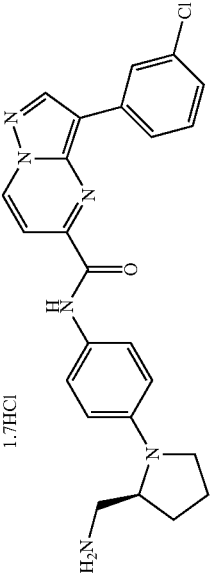 1.7HCl | B-294 | 1H-NMR(d6-DMSO+CD3OD)δ: 1.90–2.16(4H, m), 2.71–2.83(1H, m), 2.88–2.97(1H, m), 3.00–3.24(1H, m), 3.44–3.53(1H, m), 3.92–4.01(1H, m), 6.77(2H, d, J=9.3Hz), 7.35(1H, d, J=7.8Hz), 7.52(1H, t, J=7.8Hz), 7.66(1H, d, J=7.2Hz), 7.72(2H, d, J=9.3Hz), 8.30(1H, d, J=7.8Hz), 8.37(1H, s), 8.99(1H, s), 9.34(1H, d, J=7.2Hz). | |

TABLE 2-continued

| Chemical Formula | Compound No. | NMR | m.p. (° C.) |
|---|---|---|---|
| (3-chlorophenyl-pyrazolopyridine carboxamide with N-((S)-1-hydroxy-3-phenylpropan-2-yl)) | B-295 | — | — |
| (3-chlorophenyl-pyrazolopyridine carboxamide with 4-(4-methylpiperazin-1-yl)phenyl) | B-296 | — | — |
| (3-trifluoromethylphenyl-pyrazolopyridine carboxamide with 4-(piperazin-1-yl)phenyl) | B-297 | — | — |
| (3-trifluoromethoxyphenyl-pyrazolopyridine carboxamide with 4-(piperazin-1-yl)phenyl) | B-298 | 1H-NMR(CDCl3)δ: 3.02–3.21(8H, m), 6.99(2H, d, J=8.7Hz), 7.16–7.24(1H, m), 7.53(1H, t, J=8.1Hz), 7.67(2H, d, J=8.7Hz), 7.80–7.86(1H, m), 7.88(1H, d, J=7.2Hz), 8.06–8.11(1H, m), 8.55(1H, s), 8.88(1H, d, J=7.2Hz), 9.50–9.58(1H, br-s). | — |

TABLE 2-continued

| Compound No. | NMR | m.p. (° C.) |
|---|---|---|
| B-299 | — | — |
| B-300 | — | — |
| B-301 | 1H-NMR(CDCl3)δ: 3.36-3.41(4H, m), 4.04(2H, m), 4.14(2H, m), 6.93(1H, t, J=7.2Hz), 7.00(2H, m), 7.25-7.41(5H, m), 7.85(1H, m), 8.16(1H, t, J=1.8Hz), 8.52(1H, s), 8.79(1H, d, J=7.5Hz), | — |

TABLE 2-continued
| Chemical Formula | Compound No. | NMR | m.p. (° C.) |
|---|---|---|---|
| 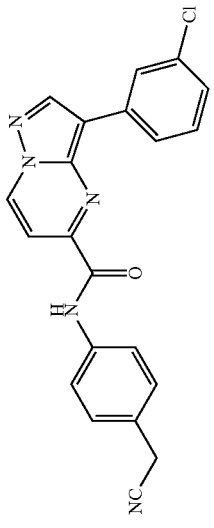 | B-302 | — | — |
| 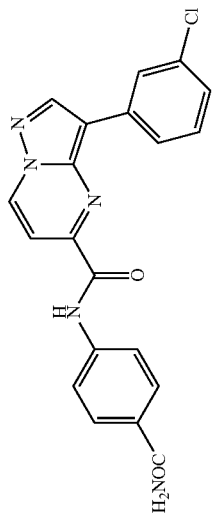 | B-303 | — | — |
| 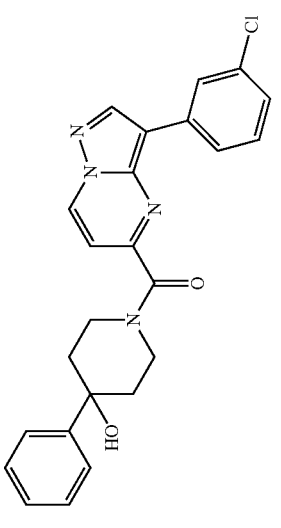 | B-304 | — | — |
| 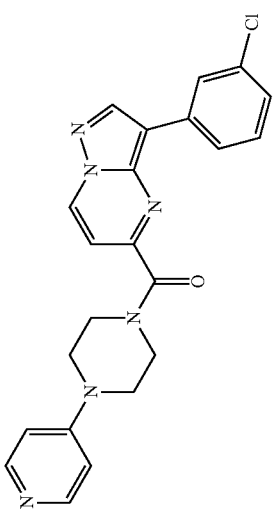 | B-305 | — | — |

TABLE 2-continued

| Compound No. | Chemical Formula | NMR | m.p. (° C.) |
|---|---|---|---|
| B-306 | (structure: 3-(3-chlorophenyl)pyrazolo[1,5-a]pyrimidine with carbonyl linked to 4-phenyl-4-cyanopiperidine) | — | — |
| B-307 | (structure: 3-(3-chlorophenyl)pyrazolo[1,5-a]pyrimidine-carboxamide with 4-(3-aminopyrrolidin-1-yl)phenyl) | — | — |
| B-308 | (structure: 3-(3-chlorophenyl)pyrazolo[1,5-a]pyrimidine-carboxamide with 4-(pyrrolidin-3-yloxy)phenyl) | 1H-NMR(d6-DMSO)δ: 1.71–1.82(1H, m), 1.96–2.08(1H, m), 2.73–3.09(4H, m), 4.82–4.89(1H, m), 6.97(1H, d, J=9.0Hz), 7.35(1H, d, J=8.1Hz), 7.52(1H, t, J=8.1Hz), 7.64(1H, d, J=7.2Hz), 7.76(2H, d, J=9.0Hz), 8.31–8.37(2H, m), 9.02(1H, s), 9.36(1H, d, J=7.2Hz), 10.56(1H, br-s). | — |

TABLE 2-continued

| Chemical Formula | Compound No. | NMR | m.p. (° C.) |
|---|---|---|---|
| | B-309 | — | — |
| | B-310 | — | — |
| | B-311 | 1H-NMR(CDCl3)δ: 1.69(2H, m), 2.04(2H, m), 2.75(2H, m), 3.16(2H, m), 4.23(1H, br), 4.39(2H, m), 4.44(2H, d, J=5.1Hz), 6.80(2H, d, J=8.7Hz), 6.96(2H, d, J=8.7Hz), 7.28–7.44(5H, m), 7.64(2H, d, J=8.7Hz), 7.75(1H, d, J=7.5Hz), 7.80(2H, d, J=8.7Hz), 8.42(1H, s), 8.79(1H, d, J=7.5Hz), 9.60(1H, s). | — |

TABLE 2-continued

| Compound No. | Chemical Formula | NMR | m.p. (° C.) |
|---|---|---|---|
| B-312 | (structure) | — | — |
| B-313 | (structure) · CO₂H-CH=CH-CO₂H | — | 211–212 |
| B-314 | (structure) · 1/2 H₂O · iPrOH | — | 100–102(d) |

TABLE 2-continued

| Chemical Formula | Compound No. | NMR | m.p. (° C.) |
|---|---|---|---|
| (structure with ClH, piperazine-NH, phenyl-NHSO₂Me, pyrazolopyrimidine, 3-chlorophenyl) | B-315 | — | — |
| (structure with aminomethyl-piperidine, phenyl, amide, pyrazolopyrimidine, 3-chlorophenyl) | B-316 | — | 159–160 |
| (structure with piperazine, methoxyphenyl, amide, pyrazolopyrimidine, 4-chlorophenyl) | B-317 | — | 210–212 |

TABLE 2-continued

| Compound No. | Chemical Formula | NMR | m.p. (° C.) |
|---|---|---|---|
| B-318 | | — | 186–188 |
| B-319 | 1/2 H₂O | — | 216–217 |
| B-320 | | — | — |

TABLE 2-continued

| Chemical Formula | Compound No. | NMR | m.p. (° C.) |
|---|---|---|---|
| | B-321 | — | — |
| | B-322 | — | — |
| | B-323 | — | — |

TABLE 2-continued

| Chemical Formula | Compound No. | NMR | m.p. (° C.) |
|---|---|---|---|
| (structure) | B-324 | 1H-NMR(d6-DMSO)δ: 1.01(3H, t, J=7.2), 1.11–1.23(2H, m), 1.32–1.44(2H, m), 1.86–1.97(2H, m), 2.00–2.11(2H, m), 2.39–2.51(1H, m), 2.55(2H, q, J=7.2Hz), 4.21–4.32(1H, m), 6.99(2H, d, J=9.0Hz), 7.35(1H, d, J=7.8Hz),7.52(1H, t, J=7.8Hz), 7.64(1H, d, J=7.2Hz), 7.74(2H, d, J=9.0Hz), 8.33(1H, d, J=7.8Hz), 8.34(1H, s), 9.01(1H, s), 9.36(1H, d, J=7.2Hz), 10.54(1H, br-s). | — |
| (structure) | B-325 | — | — |
| (structure) | B-326 | — | — |

TABLE 2-continued

| Chemical Formula | Compound No. | NMR | m.p. (° C.) |
|---|---|---|---|
| (structure with pyrazolopyridine, 3,5-bis(trifluoromethyl)phenyl, and 4-piperazinylphenyl amide) | B-327 | 1H-NMR(CDCl3)δ: 3.02–3.21(8H, m), 7.00(2H, d, J=9.0Hz), 7.69(2H, d, J=9.0Hz), 7.83(1H, br-s), 7.95(1H, d, J=7.2Hz), 8.56(2H, br-s), 8.66(1H, s), 8.93(1H, d, J=7.2Hz), 9.55–9.62(1H, br-s). | — |
| (structure with pyrazolopyridine, 3-chlorophenyl, and 3-chloro-4-(piperidin-4-yloxy)phenyl amide) | B-328 | — | — |
| (structure with pyrazolopyridine, 3-chlorophenyl, and N-(furan-2-ylmethyl)-N-(piperidin-4-yl) amide) | B-329 | — | — |

TABLE 2-continued

| Chemical Formula | Compound No. | NMR | m.p. (° C.) |
|---|---|---|---|
| (structure) | B-330 | 1H-NMR(CDCl3)δ: 0.93(3H, d, J=6.0Hz), 2.39–2.48(1H, m), 2.62–2.94(6H, m), 7.11–7.28(3H, m), 7.31–7.37(1H, m), 7.43(1H, t, J=8.1Hz), 7.84–7.93(3H, m), 8.46(1H, s), 8.47–8.53(1H, m), 8.88(1H, d, J=7.2Hz),10.54–10.62(1H, br-s). | — |
| (structure) | B-331 | — | — |
| (structure) | B-332 | 1H-NMR(CDCl3)δ: 1.10–1.30(2H, m), 1.56–1.76(3H, m), 2.50–2.63(4H, m), 3.02–3.13(2H, m), 7.21(2H, d, J=8.7Hz), 7.34(1H, ddd, J=7.8, 1.8, 1.2Hz), 7.44(1H, t, J=7.8Hz), 7.70(2H, dt, J=8.7, 2.1Hz), 7.83(1H, dt, J=7.8, 1.5Hz), 7.86(1H, d, J=7.2Hz), 8.17(1H, t, J=1.8Hz), 8.55(1H, s), 8.88(1H, d, J=7.2Hz), 9.66–9.73(1H, br-s). | — |

TABLE 2-continued
| Compound No. | Chemical Formula | NMR | m.p. (° C.) |
|---|---|---|---|
| B-333 | 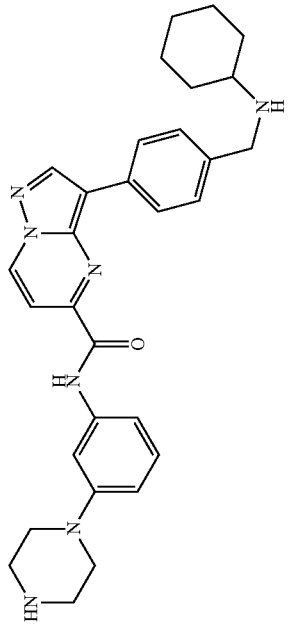 | — | — |
| B-334 | 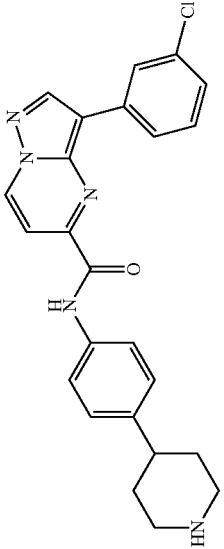 | 1H-NMR(CDCl3)δ: 1.65(2H, qd, J=12.2, 3.9Hz), 1.80–1.91(2H, m), 2.65(1H, tt, J=12.2, 3.6Hz), 2.76(2H, td, J=12.2, 2.4Hz), 3.16–3.26(2H, m), 7.24–7.37(3H, m), 7.45(1H, t, J=7.8Hz), 7.72(2H, dt, J=8.4,1.8Hz), 7.84(1H, dt, J=7.8, 1.5Hz), 7.86(1H, d, J=7.2Hz), 8.16(1H, t, J=1.8Hz), 8.55(1H, s), 8.88(1H, d, J=7.2Hz), 9.62–9.71(1H, br-s). | — |

TABLE 2-continued

| Chemical Formula | Compound No. | NMR | m.p. (° C.) |
|---|---|---|---|
| (3-chlorophenyl-pyrazolo[1,5-a]pyrimidine with N-benzyl-N-(4-methylamino-piperidinyl) carboxamide) | B-335 | — | — |
| (4-chlorophenyl-pyrazolo[1,5-a]pyrimidine-urea linked to 2-(4-(sec-butylamino)piperidin-1-yl)phenyl) | B-336 | — | >300 |

Example 21

In Vitro Test on the Compound of the Present Invention

By the following methods, the inhibition activity of a representative compound of the present invention on NAD(P)H oxidase activity, was investigated in vitro.

1. Adjustment of Bovine Aortic Membrane Fraction

Bovine aortic membrane fraction was used as enzyme preparation. Sectioned bovine aortic smooth muscle layer was pulverized with an iron mill, homogenized in 10-times the amount of homogenization buffer (pH 7.4; 20 mM MOPS, 250 mM Scrose), the fractional centrifuged supernatants of 1,000 g (15 minutes, 4° C.), 10,800 g (15 minutes, 4° C.) and 29,000 g (15 minutes, 4° C.) and pellet of 100,000 g centrifuged for 60 minutes were resuspended in MOPS Buffer (pH 7.4). These were stored as stocks of enzyme preparation at −80° C.

2. Measurement of NADH/NADPH Oxidase Inhibition Activity

For NADH/NADPH oxidase activity and compound inhibition activity, $O_2^-$ produced in NADH/NADPH oxidase reaction was calculated by determining chemical luminescence with lucigenin using an improved version of the method by Griendling et al. (Griendling K, Ollerenshaw J D, Minieri C A, Alexander R W (1994) Angiotensin II stimulates NADH and NADPH oxidase activity in cultured vascular smooth muscle cells. Circ. Res. 74; 1141-1148). In other words, a NADH/NADPH oxidase enzyme preparation and the compound of the present invention, which was dissolved in dimethyl sulfoxide, were added to 20 mM MOPS buffer (pH 7.4) containing 5 μM lucigenin and 100 μM NADH, followed by reaction at 37° C. Chemical luminescence produced by excitation of lucigenin by $O_2^-$ released by the enzyme reaction was detected with a luminescence reader and determined as enzyme activity.

3. Results

For the following exemplified compounds of the present invention, the values of 1 μM or lower are given as IC50 values:

A50, A55, A78, A79, A97, A99, A114, A117, A119, A123, A134, A139, A164, A198, A212, A215, A222, A227, A231, A234, A243, A247, A252, A253, A255, A259, A262, A268, A277, A293, A299, A302, A303, A309, A311, A316, A318, A326, A335.

B2-B9, B11, B13, B15-B20, B22, B23, B26, B27, B29, B31-B33, B35-B43, B45-B47, B50-B61, B63-B66, B68, B72, B74, B75, B77, B79, B81-B92, B96, B102, B109-B111, B113, B123, B124, B127, B129-B132, B136-B144, B146-B148, B150, B151, B153-B156, B160, B164-B166, B168, B170-B175, B177, B178, B182, B189, B191-B193, B195-B196, B198-B203, B205-B212, B214-B218, B220-B222, B224, B225, B227-B229, B231-B244, B246, B248, B249, B251, B253, B254, B258, B263-B270, B272-B277, B279, B281, B282, B286, B290-B294, B296-B298, B300, B307, B308, B310-B314, B316-B318, B320-B322, B324-B328, B330-B334.

Example 22

In Vivo Test on the Compound of the Present Invention

The inhibitory of NAD(P)H oxidase activity by a representative compound of the present invention was investigated in vivo. As a result, it became clear that the compounds of the present invention show the inhibitory activity of NAD(P)H oxidase in neutrophils and blood vessels and treat various circulatory diseases (such as diseases due to inflammation, circulatory disorders, enhanced proliferation activities, and the like, i.e., hypertension, diabetes, diabetic complications, arteriosclerosis, coronary artery disorders, strokes, ischemic heart disease, neurodegenerative diseases, pulmonary circulation disorders, cerebral circulation disorders, nephritis, arthritis, inflammatory diseases, cancers), and gastric mucosa disorders (such as gastric ulcer).

INDUSTRIAL APPLICABILITY

According to the present invention, novel pyrazolo[1,5-a] pyrimidine derivative and analog are afforded, which have inhibitory activity of NAD(P)H oxidase in neutrophils and blood vessels. Various circulatory diseases (such as diseases due to inflammation, circulatory disorders, enhanced proliferation activities, and the like, i.e., hypertension, diabetes, diabetic complications, arteriosclerosis, coronary artery disorders, strokes, ischemic heart disease, neurodegenerative diseases, pulmonary circulation disorders, cerebral circulation disorders, nephritis, arthritis, inflammatory diseases, cancers), and gastric mucosa disorders (such as gastric ulcer) can be treated by the above inhibitory action.

What is claimed is:

1. A compound represented by the formula:

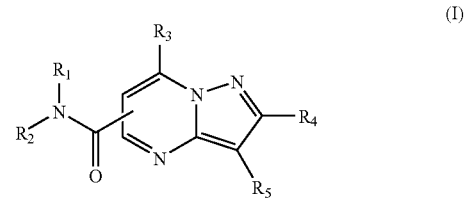

(I)

or a pharmaceutically acceptable salt or solvate thereof, wherein, in the formula (I), $R_1$ is hydrogen, lower alkyl, amino, substituted amino, aryl lower alkyl, or substituted aryl lower alkyl; and $R_2$ is hydrogen, lower alkyl, substituted lower alkyl, cycloalkyl, substituted cycloalkyl, cycloalkyl lower alkyl, substituted cycloalkyl lower alkyl, lower alkoxy, substituted lower alkoxy, aryl, substituted aryl, aryl lower alkyl, substituted aryl lower alkyl, aryloxy lower alkyl, substituted aryloxy lower alkyl, lower alkylsulfonyl, substituted lower alkylsulfonyl, arylsulfonyl, substituted arylsulfonyl, heterocyclic group lower alkyl, substituted heterocyclic group lower alkyl, amino, or substituted amino; or $R_1$ and $R_2$ together with the adjacent N atom may form a heterocyclic group or substituted heterocyclic group;

$R_3$ is hydrogen, hydroxy, lower alkoxy, halogen, amino, di-lower alkyl amino, lower alkyl carbonyl amino, lower alkoxy carbonyl lower alkyl amino, hydroxy lower alkyl amino, carbamoyl amino, lower alkoxy lower alkyl amino, lower alkyl sulfonyl amino, or cycloalkyl amino, wherein said substituent may together with the N-atom of the amino form a heterocyclic group;

$R_4$ is hydrogen, lower alkyl, aryl, or substituted aryl; and $R_5$ is hydroxy, lower alkyl, substituted lower alkyl, aryl, substituted aryl, aryl lower alkyl, substituted aryl lower alkyl, cycloalkyl lower alkyl, substituted cycloalkyl lower alkyl, aryl lower alkenyl, substituted aryl lower alkenyl, cycloalkyl lower alkenyl, substituted cycloalkyl lower alkenyl, aryl lower alkynyl, substituted aryl lower alkynyl, cycloalkyl lower alkynyl, substituted cycloalkyl lower alkynyl, aryl carbonyl, substituted aryl carbonyl, aryl lower alkyl carbonyl, substituted aryl lower alkyl carbonyl, heterocyclic group, substituted heterocyclic group, halogen, CHO, amino, substituted amino, imino, or substituted imino;

wherein the heterocyclic groups contain at least one hetero atom selected from the group consisting of oxygen, sulfur, and nitrogen, wherein the heterocyclic groups are monocyclic, bicyclic, or tricyclic, wherein the heterocyclic groups are aromatic or non-aromatic, and wherein the heterocyclic groups have 5-7 members;

wherein the substituted alkyl, alkoxy, alkenyl, alkynyl and amino groups are substituted with one or more substituents selected from the group consisting of: halogen; hydroxy; lower alkoxy; substituted lower alkoxy; aryloxy, $R_9C(O)O$—, wherein $R_9$ is a hydrocarbon group or a heterocyclic group; $R_{10}OC(O)$—, wherein $R_{10}$ is a hydrocarbon group or a heterocyclic group; carbamoyl; diazo; cyano; amino, substituted amino; imino; amidino; azido; nitro; nitroso; mercapto; $R_{17}S$—, wherein $R_{17}$ is a hydrocarbon group or a heterocyclic group; $R_{18}SO$—, wherein $R_{18}$ is a hydrocarbon group or a heterocyclic group; $R_{20}S(O)$—, wherein $R_{20}$ is a hydrocarbon group or a heterocyclic group; $R_{19}S(O)_2$—, wherein $R_{19}$ is a hydrocarbon group or a heterocyclic group; sulfo; an alicyclic hydrocarbon group; aryl; substituted aryl; a heterocyclic group; a substituted heterocyclic group; heterocyclic oxy; acyl; trialkyl silyl; monoalkyl diaryl silyl and dialkyl monoaryl silyl; and wherein the substituted aryl, heterocyclic and cycloalkyl groups are substituted with one or more substituents selected from the group consisting of: lower alkyl; substituted lower alkyl; lower alkenyl; substituted lower alkenyl; lower alkynyl; substituted lower alkynyl; halogen; hydroxy; lower alkoxy; substituted lower alkoxy; aryloxy; $R_9C(O)O$—, wherein $R_9$ is a hydrocarbon group or a heterocyclic group; $R_{10}OC(O)$—, wherein $R_{10}$ is a hydrocarbon group or a heterocyclic group; carbamoyl; diazo; cyano; amino; substituted amino; imino; amidino; azido, nitro, nitroso, mercapto; $R_{17}S$—, wherein $R_{17}$ is a hydrocarbon group or a heterocyclic group; $R_{18}SO$—, wherein $R_{18}$ is a hydrocarbon group or a heterocyclic group; $R_{20}S(O)$—, wherein $R_{20}$ is a hydrocarbon group or a heterocyclic group; $R_{19}S(O)_2$—, wherein $R_{19}$ is a hydrocarbon group or a heterocyclic group; sulfo; an alicyclic hydrocarbon group; aryl; substituted aryl; a heterocyclic group; a substituted heterocyclic group; heterocyclic oxy; acyl; trialkyl silyl; monoalkyl diaryl silyl and dialkyl monoaryl silyl; and wherein the substituted imino group is substituted with one or more substituents selected from the group consisting of: hydroxy, alkoxy, alkyl, aralkyl, acyl, aryl sulfonyl, alkyl sulfonyl, and carbamoyl;

provided that a compound represented by the following formula is excluded:

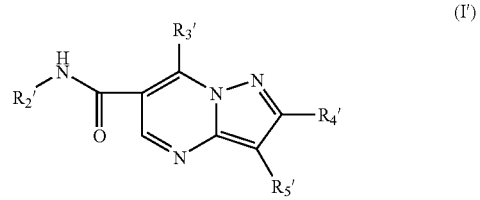

wherein, in the formula (I'),
$R_2'$ is hydrogen, phenyl or phenyl substituted with lower alkyl or halogen; $R_3'$ is hydrogen or hydroxy; $R_4'$ is hydrogen or lower alkyl; and $R_5'$ is phenyl having an unsubstituted phenylthio group or a phenylthio group substituted with lower alkyl or lower alkoxy.

2. The compound of claim 1, represented by the formula:

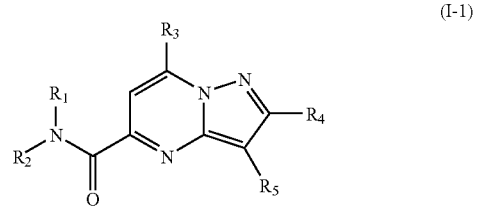

or a pharmaceutically acceptable salt or solvate thereof,
wherein, in the formula (I-1), each substituent is as defined in claim 1.

3. The compound of claim 1 or 2, or, a pharmaceutically acceptable salt or solvate thereof, wherein $R_1$ is hydrogen; and $R_2$ is aryl or substituted aryl.

4. The compound of claim 1 or 2, or a pharmaceutically acceptable salt or solvate thereof, wherein $R_3$ is hydrogen, amino, di-lower alkyl amino, lower alkyl carbonyl amino, lower alkoxy carbonyl lower alkyl amino, hydroxy lower alkyl amino, carbamoyl amino, lower alkoxy lower alkyl amino, lower alkyl sulfonyl amino, or cycloalkyl amino, wherein said substituent may together with the N-atom of the amino form a heterocyclic group.

5. The compound of claim 1 or 2, or a pharmaceutically acceptable salt or solvate thereof, wherein $R_4$ is hydrogen.

6. The compound of claim 1 or 2, or a pharmaceutically acceptable salt or solvate thereof wherein $R_5$ is aryl or substituted aryl.

7. The compound of claim 1 or 2, or a pharmaceutically acceptable salt or solvate thereof, wherein $R_1$ is hydrogen; $R_2$ is phenyl or substituted phenyl; $R_3$ is hydrogen, amino, or substituted amino; $R_4$ is hydrogen; and $R_5$ is phenyl or substituted phenyl.

8. The compound of claim 7, or a pharmaceutically acceptable salt or solvate thereof wherein the substituent on the phenyl in $R_2$ is one or more selected from the group consisting of heterocyclic group, substituted heterocyclic group, lower alkyl carbonyl, cycloalkyl, lower alkyl, amino, substituted amino, halogen, halogenated lower alkyl, lower alkoxy, carboxy lower alkyloxy, heterocyclic group lower alkyloxy, amino lower alkyl, hydroxy, cyano, carbamoyl-heterocyclic group-oxy, cyano lower alkyl, and phenyl.

9. The compound of claim 8, or a pharmaceutically acceptable salt or solvate thereof wherein $R_2$ is heterocyclic group or substituted heterocyclic group phenyl.

10. The compound of claim 8, or a, pharmaceutically acceptable salt or solvate thereof, wherein $R_2$ is piperazino phenyl, substituted piperazino phenyl, piperizino phenyl, substituted piperizino phenyl, pyrrolidino phenyl, or substituted pyrrolidino phenyl.

11. The compound of claim 7, or a pharmaceutically acceptable salt or solvate thereof, wherein the substituent on the phenyl in $R_5$ is one or more selected from the group consisting of halogen, halogenated lower alkyl, aryl lower alkyloxy, lower alkyl, lower alkoxy, hydroxy, lower alkylthio, phenyl, phenyloxy, phenyl lower alkyl, phenyl lower alkylamino, phenyl lower alkylthio, phenyl lower alkenyl, phenyl carbamoyl, amino, and cycloalkyl lower alkyloxy.

12. A pharmaceutical composition, comprising the compound of any one of claims 1-11 and a physiologically acceptable carrier.

\* \* \* \* \*